(12) United States Patent
Elizarov et al.

(10) Patent No.: US 10,309,947 B2
(45) Date of Patent: Jun. 4, 2019

(54) SYSTEM AND METHOD FOR RADIOSYNTHESIS, QUALITY CONTROL AND DOSE DISPENSING

(71) Applicant: Trace-Ability, Inc., Van Nuys, CA (US)

(72) Inventors: Arkadij Elizarov, Woodland Hills, CA (US); Artem Lebedev, Santa Monica, CA (US)

(73) Assignee: Trace-Ability, Inc., Van Nuys, CA (US)

( * ) Notice: Subject to any disclaimer, the term of this patent is extended or adjusted under 35 U.S.C. 154(b) by 146 days.

(21) Appl. No.: 14/191,293

(22) Filed: Feb. 26, 2014

(65) Prior Publication Data

US 2016/0003791 A1   Jan. 7, 2016

Related U.S. Application Data

(60) Provisional application No. 61/888,477, filed on Oct. 8, 2013, provisional application No. 61/886,607, filed
(Continued)

(51) Int. Cl.
*G01N 35/00* (2006.01)
*G01N 33/15* (2006.01)
*G01N 33/00* (2006.01)

(52) U.S. Cl.
CPC ..... *G01N 33/15* (2013.01); *G01N 2033/0093* (2013.01)

(58) Field of Classification Search
CPC .... B01J 19/00; B01J 19/0046; B01J 19/0093; B01J 19/08; B01J 19/081;
(Continued)

(56) References Cited

U.S. PATENT DOCUMENTS

| 5,310,657 A | 5/1994 | Berzofsky |
| 7,329,538 B2 | 2/2008 | Wainwright et al. |

(Continued)

FOREIGN PATENT DOCUMENTS

| CN | 1036078 A | 10/1989 |
| CN | 2898829 Y | 5/2007 |

(Continued)

OTHER PUBLICATIONS

PCT Search Report & Written Opinion dated Jan. 26, 2016 for PCT/US2015/052448 entitled Palette-Based Systems for Analyte Characterization filed on Sep. 25, 2015 (Applicant—Trace—ability, Inc.); 18 pages.

(Continued)

*Primary Examiner* — Jill A Warden
*Assistant Examiner* — Dwayne K Handy
(74) *Attorney, Agent, or Firm* — Harness, Dickey & Pierce, P.L.C.

(57) ABSTRACT

A system and method for performing radiochemical synthesis, analysis and/or dispensing of radiopharmaceuticals using specially designed disposable components: palettes and caddies, the palette being an assembly of containers not connected with each other for direct material transfer; the caddy being a disposable component used to transfer material between containers on the palettes and/or other locations.

16 Claims, 26 Drawing Sheets

Related U.S. Application Data on Oct. 3, 2013, provisional application No. 61/769,750, filed on Feb. 27, 2013, provisional application No. 61/834,354, filed on Jun. 12, 2013.

(58) Field of Classification Search
CPC . G01N 2033/0093; G01N 2035/00673; G01N 2035/0452; G01N 35/00029; G01N 35/00613; G01N 35/00663
USPC .......... 422/129, 130, 501, 509, 510
See application file for complete search history.

(56) References Cited

U.S. PATENT DOCUMENTS

| | | | |
|---|---|---|---|
| 8,021,611 | B2 | 9/2011 | Roach et al. |
| 8,980,184 | B2* | 3/2015 | Mueller et al. ............... 422/130 |
| 2002/0142301 | A1 | 10/2002 | Hovig et al. |
| 2004/0022696 | A1* | 2/2004 | Zigler et al. .................. 422/159 |
| 2004/0086437 | A1* | 5/2004 | Jackson ........................ 422/903 |
| 2004/0126279 | A1 | 7/2004 | Renzi et al. |
| 2006/0245980 | A1* | 11/2006 | Kiselev ..................... A61J 3/00 422/130 |
| 2009/0087924 | A1 | 4/2009 | Bynum et al. |
| 2010/0019157 | A1 | 1/2010 | Furlan et al. |
| 2010/0145630 | A1 | 6/2010 | Ball et al. |
| 2011/0070158 | A1 | 3/2011 | Nutt et al. |
| 2011/0070458 | A1 | 3/2011 | Quan et al. |
| 2012/0077429 | A1* | 3/2012 | Wernimont et al. .......... 454/187 |

FOREIGN PATENT DOCUMENTS

| | | |
|---|---|---|
| CN | 101000344 A | 7/2007 |
| CN | 101013137 A | 8/2007 |
| CN | 201935917 U | 8/2011 |
| CN | 102576007 A | 7/2012 |
| CN | 103344464 A | 10/2013 |
| EP | 1940543 A2 | 7/2008 |
| WO | 2000062931 A1 | 10/2000 |
| WO | 2009153163 A1 | 12/2009 |

OTHER PUBLICATIONS

1st Office Action in related CNSN 2015800599311 dated Apr. 27, 2018.

European Search Report and Opinion in corresponding EPSN 15845167.4 dated Mar. 26, 2018.

* cited by examiner

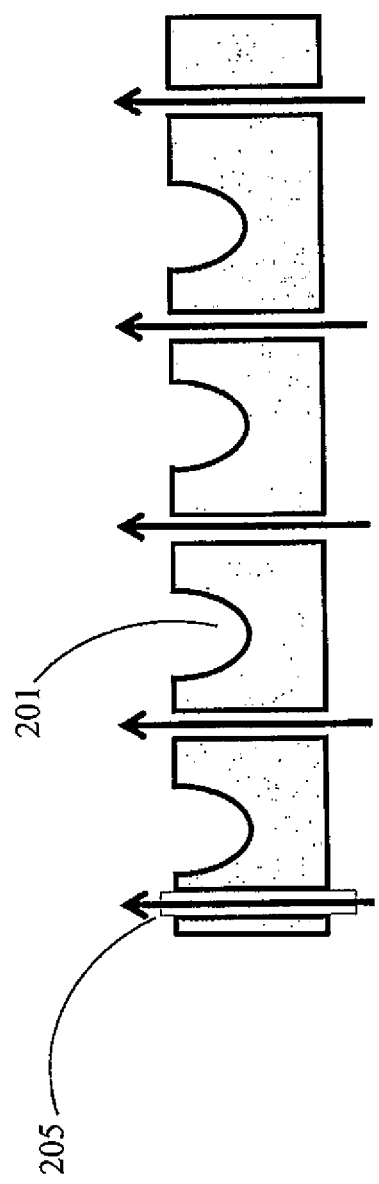

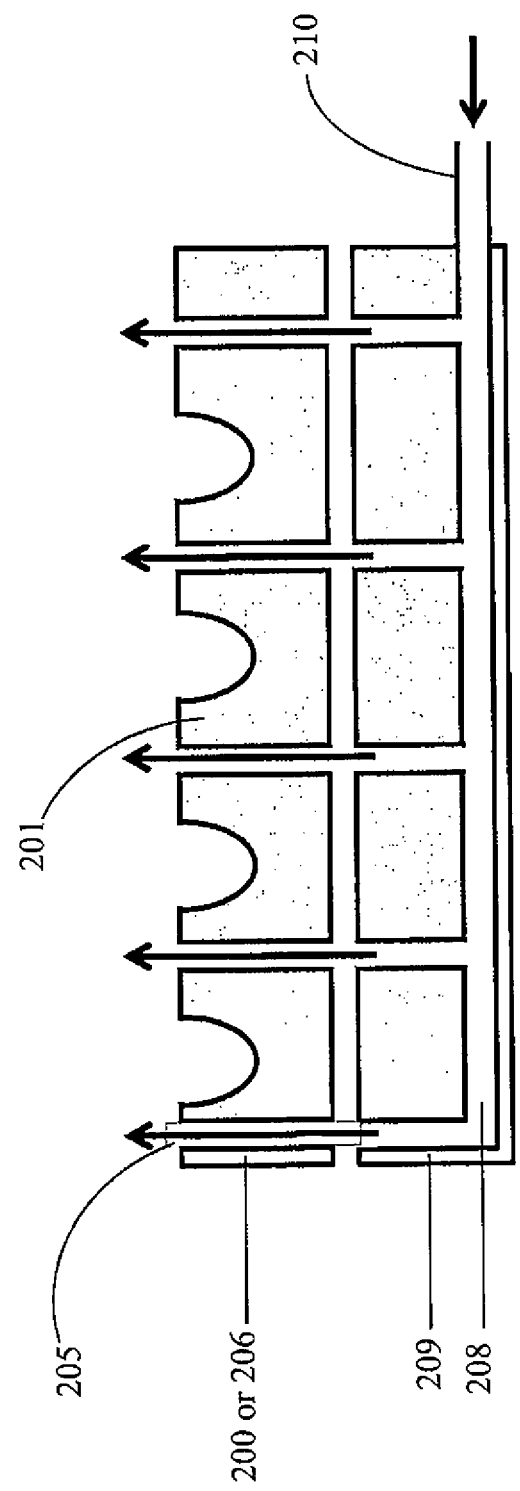

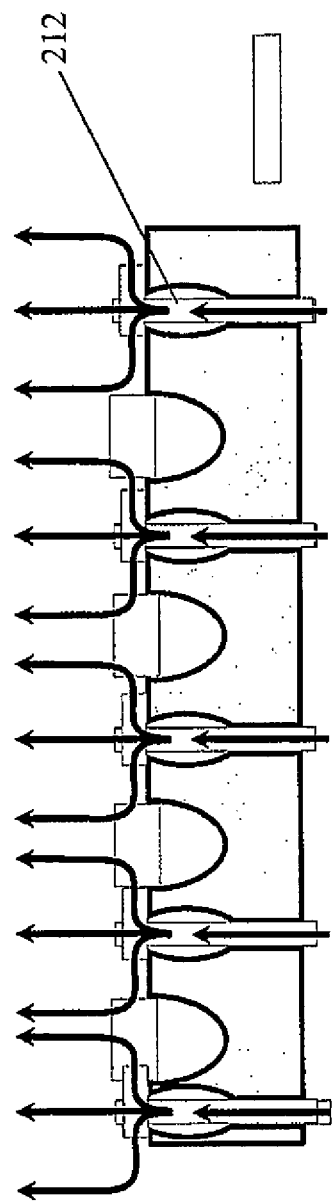

Series of absorption spectra of ($Ba^{2+}$/Xylenol orange) mixture in the presence of various concentrations of $K_{222}$, from 0 mg/ml to 1000 mg/ml

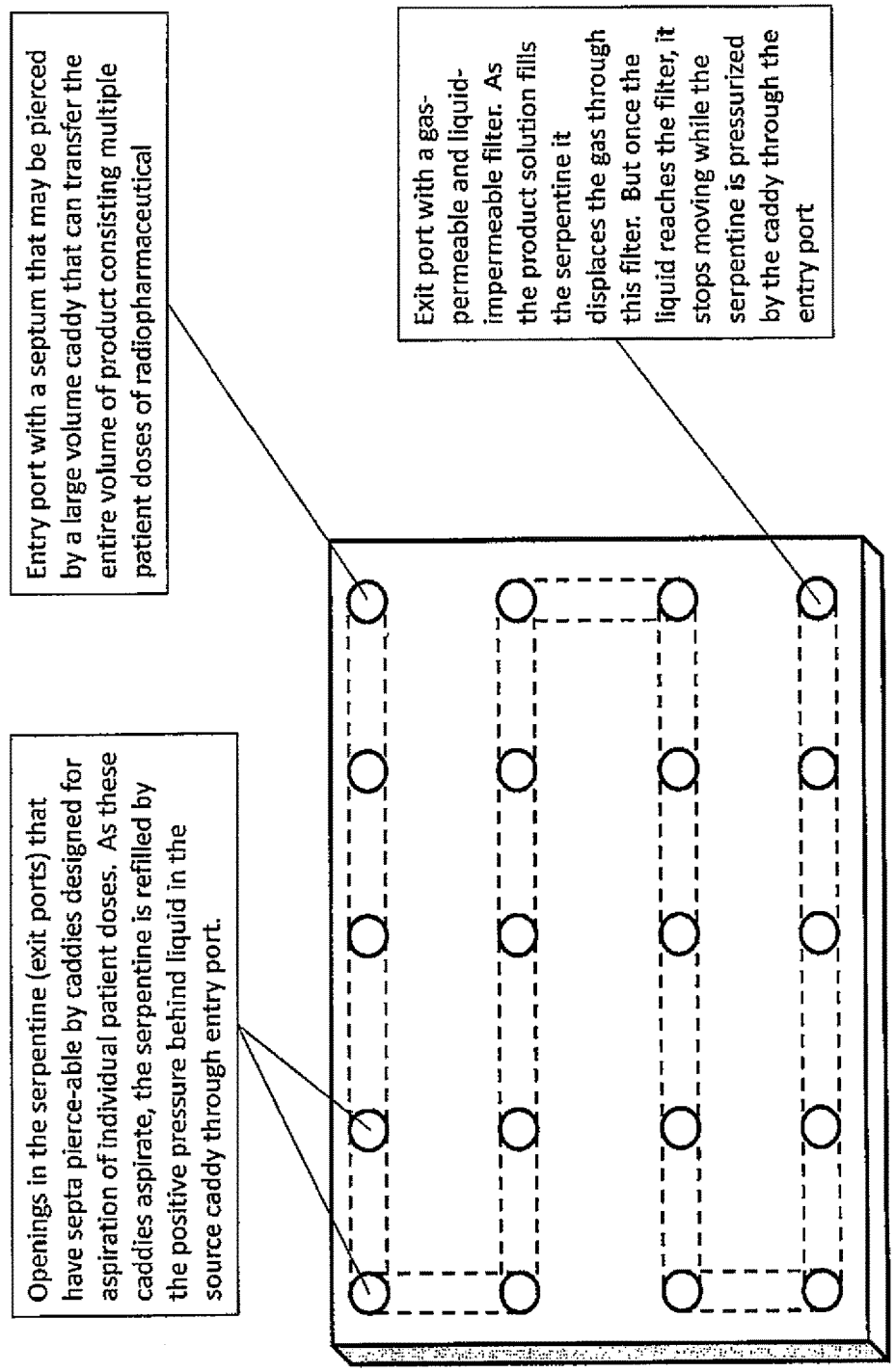
FIG. 14 Palette with a serpentine for patient dose aspiration

SYSTEM AND METHOD FOR RADIOSYNTHESIS, QUALITY CONTROL AND DOSE DISPENSING

CROSS-REFERENCE TO RELATED APPLICATIONS

This application claims the priority to and the benefit of U.S. Provisional Patent Application No. 61/769,750, filed on Feb. 27, 2013, in the United States Patent and Trademark Office, and titled VALVELESS TUBELESS RADIOSYNTHESIS AND/OR QUALITY CONTROL INSTRUMENTS; U.S. Provisional Patent Application No. 61/834,354, filed on Jun. 12, 2013, in the United States Patent and Trademark Office, and titled INSTRUMENTATION FOR SEPARATING PET TRACER PRODUCTION FROM RADIO-PHARMACY; U.S. Provisional Patent Application No. 61/886,607, filed on Oct. 4, 2013, in the United States Patent and Trademark Office, and titled DEVICES AND METHODS FOR NON-CONTACT ASSESSMENT OF PRODUCT QUALITY; U.S. Provisional Patent Application No. 61/888,477, filed on Oct. 8, 2013, in the United States Patent and Trademark Office and titled DISPOSABLE DEVICES AND METHODS FOR NON-CONTACT ASSESSMENT OF PRODUCT QUALITY; the entire contents of all of the four applications are incorporated herein by reference in their entireties.

TECHNICAL FIELD

The following description relates to systems and devices for chemical synthesis and/or analysis, and methods of using the same. The systems and devices may include apparatuses for transferring liquids, gases, solids, semi-solids, etc. Such transfers may be a part of a chemical process including (but not limited to) radio-chemical synthesis, analysis and dose dispensing. The chemicals produced or analyzed by such systems and devices may be used for medical purposes, including (but not limited to) medical imaging such as Positron Emission Tomography (PET), or Single-Photon Emission Computed Tomography (SPECT); and/or therapy with radioactive compounds such as radioactive nuclides.

BACKGROUND

The chemical transformations needed for production and analysis of radioactive medical materials are preferably done using automated modules. These modules provide for automatic handling of radioactive materials in a reproducible manner, thus reducing personnel exposure to radiation and improving reliability of production and analysis.

In known chemical synthesis/analysis systems, materials such as liquids and gases are transferred from one location to another via valves and tubes (also referred to as "plumbing", network of channels, lines) and require a "motive force" (e.g., provided by vacuum, pumping or the like). The plumbing can be installed at the time of the system manufacturing and only replaced during regular maintenance ("permanent" or "cleanable" plumbing), or it can be incorporated into a cartridge meant to be used only for one production/analysis run (disposable plumbing). Initially, this basic feature greatly simplified the design of the machines and allowed fast introduction of these systems in response to growing production of PET and SPECT radiopharmaceuticals. However, several decades in the field practice revealed a number of drawbacks typical for these systems.

In many cases, transfer of the liquid material results in considerable losses of the liquid material in the tubes due to large quantities of small droplets left on the inner walls of the lines (tubes) (which is inevitable because of high surface-to-volume ratio of the tubes). This is a fundamental limitation precluding handling of small quantities of liquid. Synthesis of the radiopharmaceuticals is therefore limited to relatively diluted solutions, as milliliter scale volumes of solvents are needed for complete transfer of a certain amount of reagent. Analytical systems relying on the network of tubes for distribution of the samples have to use no less than hundreds of microliters of samples for reliable and quantitative transfer.

Additionally, lines and/or valves may clog, be pinched or leak. These operational problems are very hard to detect, as it is nearly impossible to inspect every inch of a complex plumbing.

Compared to conventional wet chemistry done in the flasks and beakers, such automated modules provide very little flexibility for chemists. The fixed plumbing schematic of the tubing-based instruments implies that all functions of the machine must be defined at the design stage. However, introduction of new tasks, or improvement of existing methods, often require changes in the fluid schematic. These changes may require (trigger) changes in the hardware, electrical and electronic components as well as in the software operating the module. Attempts to improve functionality have inevitably led to complicated schemes, as all functionality should be in place, whether it is needed or not for each particular synthesis. To perform new operations, the instrument has to be re-designed or modified. Therefore, most of the existing radiochemistry modules can only perform a limited number of predefined operations; i.e., they are not flexible.

The limited operational flexibility of these machines also allows little chance to recover after an error. Currently, if one operation within a run is not performed as expected, the entire run has to be abandoned and the machine has to be reinitialized either through, for example, a clean cycle or by inserting a new cassette. That is because all operations have to be envisioned prior to the start of the run, even more often they have to be integrated into the machine design. More so, most machines can only execute tasks in a pre-defined sequence with no options to repeat or skip steps or to change their order. As a result, current machines have only one chance to complete their task, with no option to recover from minor errors, such as incomplete liquid delivery.

Furthermore, instruments, which rely on plumbing and valves, require complex cleaning procedures after each transfer in order to prevent contaminants in the subsequent procedure. In the case of systems based on permanent plumbing, a complex cleaning/drying cycle is performed after each run to ensure that no contaminants are left in the lines and extensive cleaning validations are required. This problem was mitigated by the use of disposable cassettes where a new set of lines is used for each run. However, some lines in the cassette are often used for several consecutive transfers and the operation protocol has to incorporate interim cleaning steps.

A separate set of limitations of current radiochemistry machines is related to the measuring of fractions of a sample or reagent stock solution. The most common mode of transfer is the transfer of the entire volume of material premeasured in a container. Alternatively, a separate system of measuring out a fraction of the container content is constructed. Such system normally requires an excess of material to be transferred. For instance, if one milliliter of a solution needs to be transferred out of a 5 milliliter vial, some amount of this solution will inevitably be wasted to prime the lines coming in and out of the vial, the measuring device (syringe) and, potentially to wash the lines prior to transfer.

A large number of systems for radio-synthesis and/or analysis of radiopharmaceuticals have been reported and patented, which rely on plumbing and valves to route liquids. Those using disposable cassettes still contain plumbing (although disposable) and valves and movable components as well as a rigid inflexible schematic. In this case the complexity is increased by the mechanical interface between the valves and their actuators, and the electronic and liquid connections between the disposable and the permanent parts of the system.

SUMMARY

According to one or more embodiments of the present invention, a system is for performing a process selected from the group consisting of (a) radiopharmaceutical synthesis, (b) quality control tests of radiopharmaceuticals, (c) radiopharmaceutical dose dispensing, and (d) any combinations thereof, the system being configured to transfer a first quantity of one or more chemicals by picking up the first quantity of the one or more chemicals at a first location, transferring the first quantity of one or more chemicals to a second location and dropping off a second quantity of the one or more chemicals at a second location, wherein the first quantity is equal to or more than the second quantity. The system may not have a continuous or confined liquid path.

The system may be for performing quality control tests of a radio-pharmaceutical product, and the system may include: a holder having a plurality of containers, each configured to contain a reagent for performing a quality control test on the radio-pharmaceutical product, and in fluidic isolation from one another, wherein at least one of the plurality of containers contains a reagent different from another container.

The system may be for performing quality control tests of a radio-pharmaceutical product, and the system may include: a palette including a plurality of containers, each of the containers including a reagent configured for reacting with the radio-pharmaceutical product and generating an optically detectable signal indicating a result of one of a plurality of quality control tests; wherein the quality control tests include at least two selected from the group consisting of clarity, pH, a phase transfer reagent concentration, pyrogenicity, radio-isotope half-life, radioactivity concentration, radiochemical and chemical purity, radiochemical identity, organic solvent concentration, sterility, color and turbidity.

The quality control tests may include one or more tests including one or more radiation measurements on positron-emitting radionuclides of the radio-pharmaceutical product, the one or more measurements including luminescence measurement of a total light output from a location where a radioactive sample is interacting with a scintillating reagent.

The one or more of the plurality of quality control tests may be assessed from a single radiopharmaceutical sample received by the system.

The plurality of quality control tests may include a test on the phase transfer reagent concentration, the phase transfer reagent is Kryptofix, and the signal is an absorbance of light detected utilizing a spectrophotometer, wherein the reagent in the container includes a metal compound and a colorimetric indicator for measuring concentration of said metal compound.

The plurality of quality control tests may include a test that simultaneously determines both color and clarity of the radio-pharmaceutical product based on a measurement of light transmitted through the sample.

The system may be for performing radiopharmaceutical synthesis of a radio-pharmaceutical product, and the system may include: a holder having a plurality of containers, one or more of the plurality of containers are configured to contain a reagent for performing synthesis of the radio-pharmaceutical product, and in fluidic isolation from one another.

The system may be for radiopharmaceutical dose dispensing of individual patient doses, and the system may include: a holder having a plurality of receptacles; and a plurality of containers, each configured to receive an individual patient dose of a radio-pharmaceutical product, to fit in a receptacle and in fluidic isolation from one another.

The system may further include a palette including a final product reservoir configured to be accessible simultaneously by the plurality of containers.

The system may include a holder having a plurality of containers, wherein the holder is a palette.

The palette may be configured to carry a liquid and/or a solid.

The palette may include a permanent container, a removable container, or a combination thereof.

The palette may include: one or more containers configured to carry a chemical in solid form that is unstable in solution form; and one or more containers configured to carry a solvent, wherein the chemical in solid form and the solvent is configured to be mixed to make a solution form of the chemical during the process.

The system may be configured to entirely or partially perform any combination of radiopharmaceutical synthesis, radiopharmaceutical quality control and radiopharmaceutical dose packaging.

The system may include a caddy configured to pick up and drop off the one or more chemicals.

The system may include a plurality of caddies and at least one of the plurality of caddies is configured to carry out a first operation different from a second operation by another one of the plurality of caddies, wherein the first operation and the second operation are carried out simultaneously.

The first operation and the second operation may be distinct chemical processes.

According to another embodiment of the present invention, a system includes a palette having a gas flow path configured to allow gas flow through at least a portion of the palette, wherein the gas flow path is configured to assure biological safety on a surface of the palette.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 2(A) to 2(H) are various designs of a palette with gas flow capabilities;

FIG. 14 illustrates an example system for parallel multiple dose dispensing according to one embodiment of the present invention;

DETAILED DESCRIPTION

Figure 1:
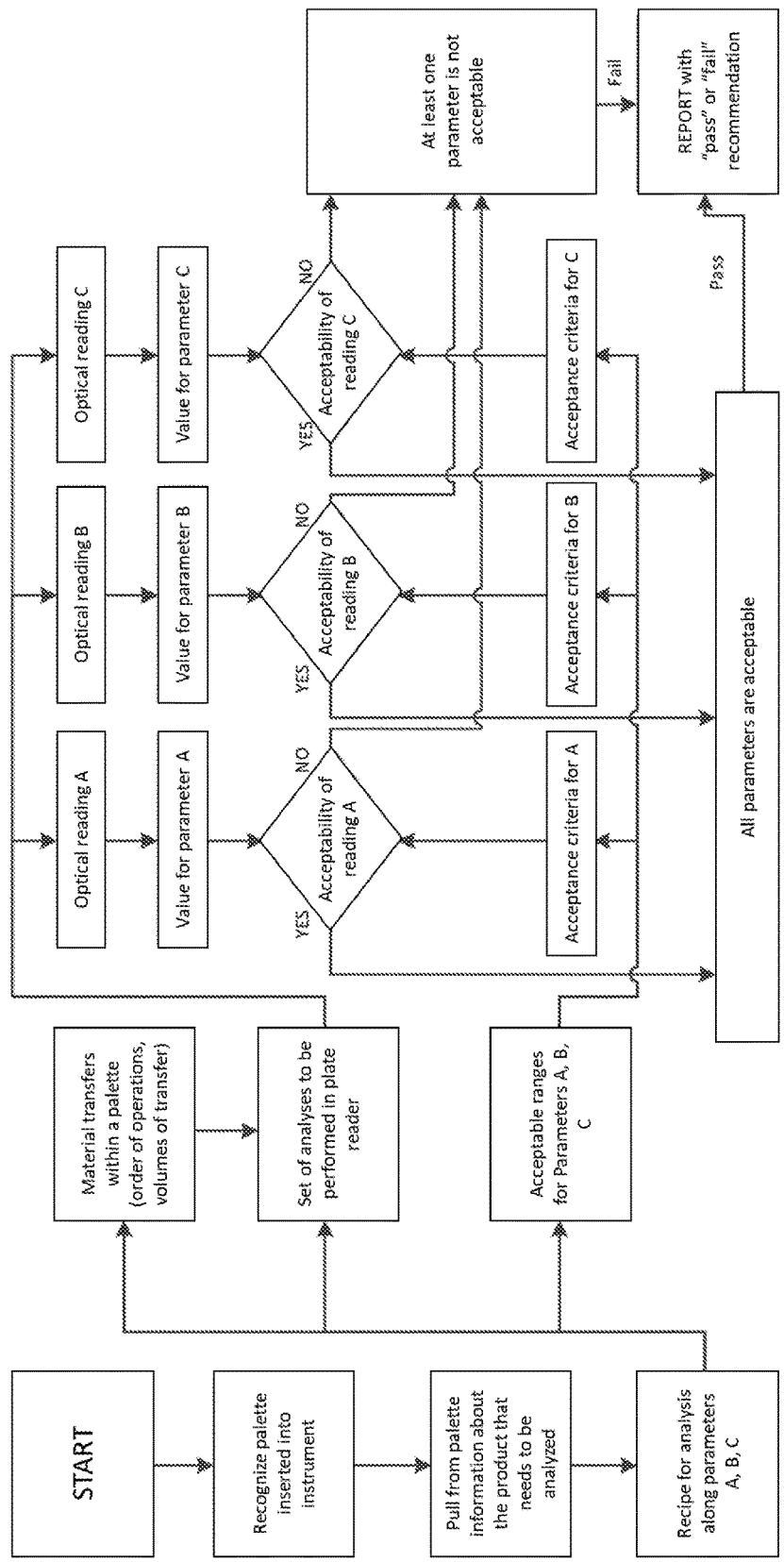
FIG. 1 is a flowchart of steps to implement an embodiment of the present invention.

Aspects according to one or more embodiments of the present invention are directed toward systems, devices, and methods for transferring materials including liquids, solids and gases, or a combination thereof. Such materials may be reagents for chemical reactions. The transfer may be used in systems and methods for carrying out chemical transformations, such as chemical reactions, synthesis, and/or analysis. One aspect according to one or more embodiments of the present invention is directed toward devices and methods utilizing one or more consumable/disposable components. Consumable or disposable means that the component, or module, may be disposed of, or recycled or refurbished following its role in the process. This recycling or refurbishing may occur at any time once the particular component has fulfilled its intended purpose. For example, one embodiment using consumable/disposable components includes a palette that carries everything needed for the analysis of the sample (except for the sample itself). The consumable can be discarded after the QC process is completed. For example, one may use a pipette with a disposable tip as a caddy to move liquids between wells/vials of the disposable palette.

The chemical transformation may be a synthesis and/or analysis of radiolabeled molecules. Such molecules can be used in nuclear medicine procedures such as PET scan, SPECT scan and/or therapeutic treatment using radionuclides. The system and device may also be used for quality control. An example of a synthesis (i.e., a synthesis procedure) of a radiolabeled compound, which may be performed by the present invention, is described in U.S. patent application Ser. No. 12/578,175, published on Apr. 15, 2010 as US2010/0093098 A1, and titled NONFLOW-THROUGH APPARATUS AND METHOD USING ENHANCED FLOW MECHANISMS, the entire content of which is incorporated by reference herein.

Other transformations may be needed for analysis of samples containing radiolabeled molecules.

The transformations may be performed in a microfluidic system, a macrofluidic system or a combination of both. In one embodiment, the transformation utilizes or produces liquids of one microliter or greater. In another embodiment, the transformation utilizes or produces liquids of 100 milliliters or less. In yet another embodiment, the transformation utilizes or produces liquids of more than 100 milliliters, for example, one liter or greater. In yet another embodiment, the transformation utilizes or produces liquids less than one microliter, for example, 900 nano-liters or less.

A system according to one or more embodiments of the present invention includes a set of disposable components for the transfer of materials (such as reagents or radiopharmaceuticals) from one location to another. At least one aforementioned disposable component is "simple", that is, made of only one piece of homogeneous material and at some point performs its function such that the material to be transferred inside this disposable component does not come into physical contact with other disposable components of the system (i.e., the fluid and/or solid inside one of the disposable components is isolated from other disposable components or the fluid or solid inside another one of the disposable components). The disposable components also have no direct liquid connection or electronic connection with the permanent parts of the instrument. For example, the system according to one or more embodiments of the present invention includes a palette-caddy system.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Expressions such as "at least one of," when preceding a list of elements, modify the entire list of elements and do not modify the individual elements of the list. Further, the use of "may" when describing embodiments of the present invention refers to "one or more embodiments of the present invention."

Palette-Caddy System

In one embodiment, the system and/or device may use a "Caddy" and "Palette" system, instead of traditional tubing, valves and a motive force for transferring materials.

A "caddy" is a disposable temporary container used to transfer by way of example a liquid such as chemicals between two locations, i.e., from one location to another. When a liquid needs to be transferred, it is "picked up" by being pulled into a caddy at one original location. The caddy is then moved to the new location and its contents are delivered and "dropped off". As such, a liquid sample is transferred via "pick-up" and "drop-off" mechanism via a caddy. The caddies are designed to be easily disposed of or exchanged after every transfer operation. Examples of a caddy include (but are not limited to) a movable vial, a pipette tip, a disposable syringe, a loop, a needle, or the like. The caddy is easily (and automatically) removable and/or exchangeable after each operation performed. This is for reducing or eliminating any chances of contaminating the reagents involved in different transformations. Various means of moving materials in and out of a caddy may be used such as evaporation of liquid by heating, condensation of a gas by cooling, gravitational or electrostatic transfer of solids and fluids, gravitational transfer of liquids, vacuum, pneumatic or hydraulic operation, etc. The volume of a caddy may be nano-liters to liters, for example, a caddy may be able to transfer samples of microliters, milliliters, or liters in size.

A "palette" is a device designed to include a plurality of by way of example liquid containers accessible via one or more caddies. When more than one caddies are utilized, each of the caddies may operate independent of the others and may access different containers on one palette at the same time, or according to any desired sequence. A palette is a structure (or device) suitable for containing multiple chemicals (solid, liquid, or gas) in fluidic isolation from one another. Here, the term "fluidic isolation" refers to a container without any connections to another container to allow the chemicals inside to flow out of its respective container. That is, the containers are not connected by any channels, tubing or valves to one another or another device. A palette may be designed to be disposable and may be used only for one production or analysis run. The container within the palette may be a well, a vial or other suitable means. For example, rather than having a physical wall that defines the boundaries of a container, the containers may be defined and separated by surface tension, electrostatic means or thermal control, such that materials deposited in one location of the palette are retained in that location and do not flow out of that location to mix with materials deposited in other locations. For example, the surface tension may be controlled by coating or depositing materials of different surface tensions in a desired pattern on a surface of the palette. For example, patches of high surface energy coating materials may be surrounded by a matrix of low surface energy coating materials.

The container may have a port accessible for the caddy. The port may be a septum to be punctured by a caddy or otherwise docked by an inlet or outlet of the caddy. The palette may include containers of various volumes. For example, the containers may have a volume of microliters, milliliters, or liters. Volume of the container may be adjusted, for example, may be reduced by using an insert of the appropriate volume. The container may be sealed, sealable, open, etc. One or more containers of a palette may be thermally isolated. Thermally isolated containers can be used to maintain low (or high) temperature inside the container or to prevent unwanted temperature fluctuations.

Examples of a palette include (but are not limited to) a multi-well plate, a rack of vials, or a custom piece of hardware designed to host one or more reagents (liquid, solid or gas) in a manner accessible to a caddy. The palette may be made of a single monolithic piece of material and have no movable parts. An example of such a palette can be a micro well plate. Alternatively, the palette may have movable parts providing flexibility to the palette. An example of such a palette may be a chain holding a container in its links. Yet another alternative can be a modular palette containing disposable and reusable parts, where materials held in the containers are only exposed to the disposable parts. An example of such a palette may include a holder and a set of disposable inserts such as a drum with holes in a portion of the drum, a tray with a grid of holes, or a set of smaller racks transported on a conveyor belt.

As disclosed above, according to some embodiments, a palette may not have any valves, tubing junctions, or moving parts and may have the following characteristics: any container on the palette may be accessible at any time to a user or a machine; all components on a palette are in fluidic isolation (fluidly isolated) from one another; processes conducted on a palette may happen in any order or in parallel, rather than follow a strict sequence; fluids may or may not be fully contained, for example, each container may or may not be completely filled up with a fluid; liquid losses are not dependent on the transfer distance, as the liquid is transferred through the movement of the caddy, and does not flow over any of the distance to be transferred; materials may be transferred from any one location to any other location in any volume; precise metering of specific amounts of liquid sample is enabled at any step in the process; fluid is not required to flow between 2 locations within a palette; each container has no electronic or fluidic connection with the instrument; and the topology of the container is fixed, no change of the shape is mechanically actuated by the instrument.

A difference between palettes and cassettes (used in other systems) is that the palettes need not contain channels, conduits and/or valves. They include liquid containers (either permanently fixed or removable, either sealed or open) may be in fluidic isolation (i.e., not in fluid communication) with one another. The palettes do not necessarily contain fluid paths. According to one or more embodiments of the present invention, fluids cannot directly flow from one location to another within the palette because palettes do not contain networks of channels, junctions or manifolds.

In one embodiment, palettes may be used in an optical measurement but without any flow of the liquids, unlike in an optical cells. An optical cell refers to a channel located between a source of light and an optical detector measuring signals arising from the liquid flowing through the said channel. Palettes are packaged with either solids or liquids or combinations of solids and liquids. This is another feature that makes them different from cassettes which may not be packaged or stored with liquids in them and require the addition of liquids to be done shortly before their use. This is because cassettes contain movable components which easily create leaking points.

It is to be noted that according to one or more embodiments of the present invention, palettes do not contain any components that may move relative to one another. No moving or movable parts are included within a palette. However, the present invention is not limited thereto. For example, one or more moving parts may be included within a palette.

All containers with liquids inside may be sealed individually and/or permanently within a palette. These reagents may be accessible by a caddy breaking a respective individual seal during the process.

Figure 2A:
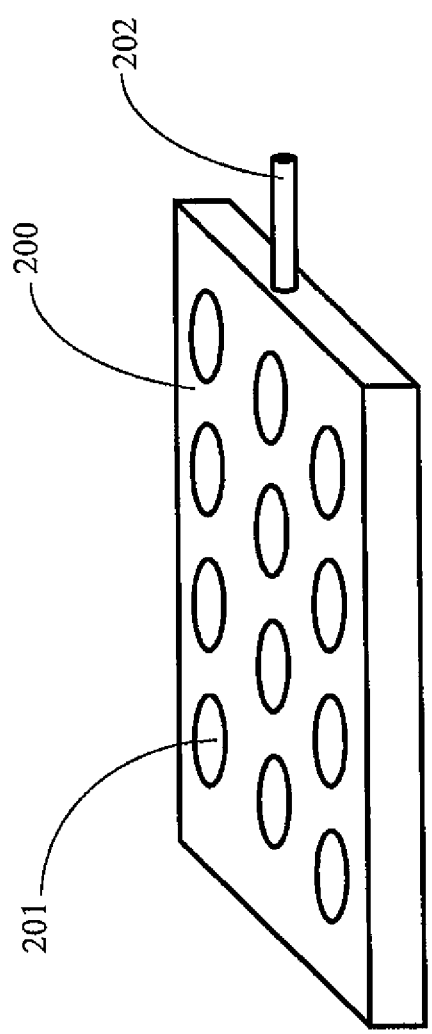

A palette may further include a gas blanket to provide a bio-safety environment and thereby eliminate the need to install the complete device (e.g., the palette, an analytical instrument, etc.) in a laminar flow hood or clean room. Examples of such palettes may be designed according to FIGS. 2(A)-2(H), which illustrates various designs to assure a bio-safety environment around each palette. According to one or more embodiments of the present invention, a palette with a bio-safety environment, such as those described in these figures, may be utilized for radiopharmaceutical applications, but not limited thereto. For example, such a palette may be utilized for non-radiopharmaceutical applications, such as Immunoassays, blood analysis, and other in vitro diagnostic applications. Referring to FIGS. 2(A)-2(H), the gas may be connected to the palette or to a manifold below the palette that enables flow of gas through the palette once it is in place within the instrument and forms a gas blanket (i.e., a layer of gas) over the surface of the palette. In this case, rather than control the entire system (such as the palette with the samples on it and analytical instruments) by placing instruments in laminar flow hoods, a laminar flow micro environment is created at a specific location (without spatial confinement). FIG. 2(A) is a schematic illustration of a palette 200 with a plurality of containers 201 and an inlet 202 for gas to flow through the palette and around the containers, but not through (at least some of) the inside of the containers 201.

Figure 2B:
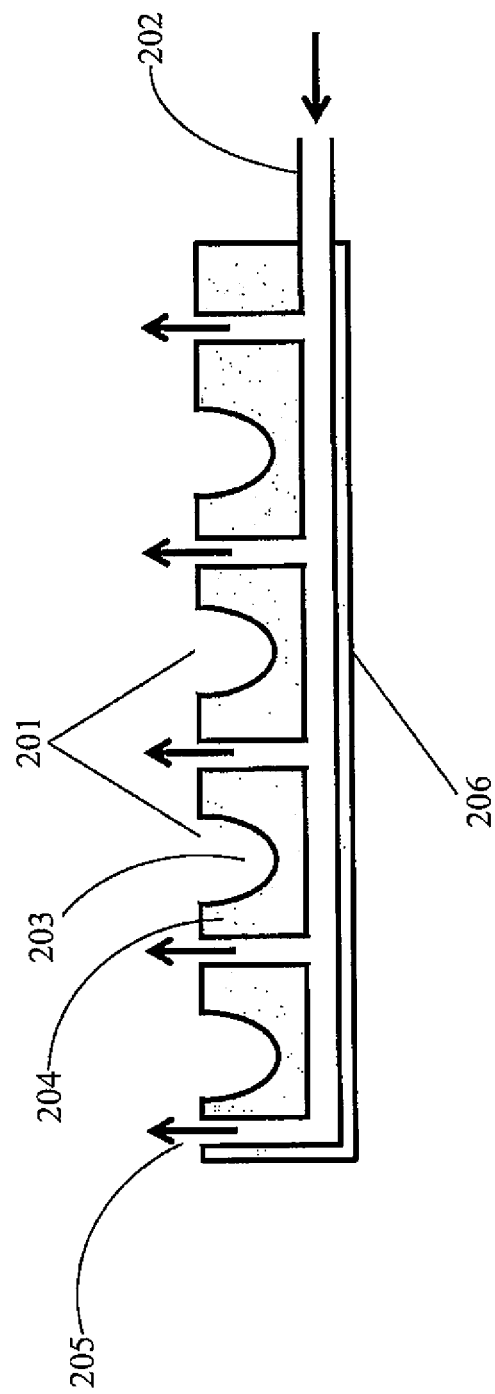

FIG. 2(B) is a cross-sectional view of the palette 200 of FIG. 2(A). Each container 201 has an internal space 203 for holding the reagents, surrounded by a wall 204. A gas channel 205 is formed between the walls 204 of neighboring containers 201 and/or between the containers 201 and the frame 206 of the palette.

Figure 2C:
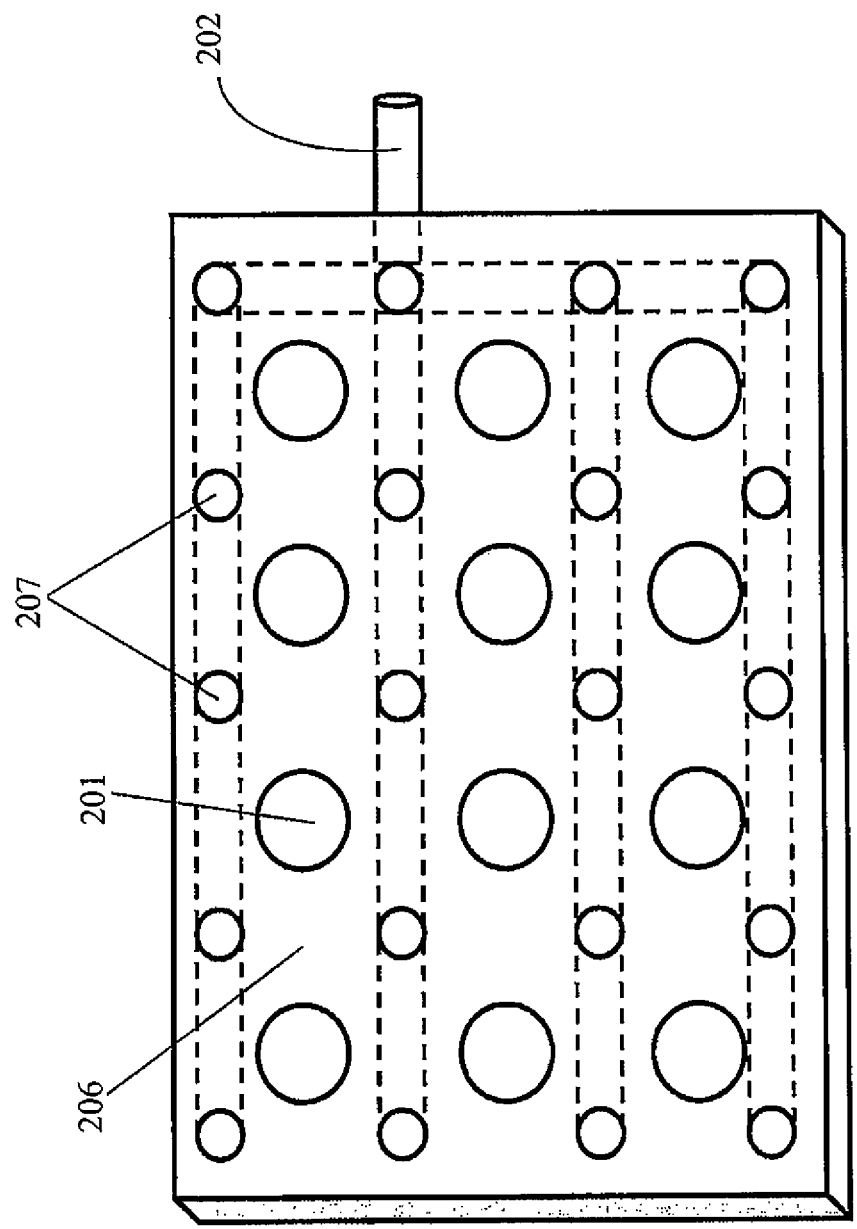
Figure 2F:
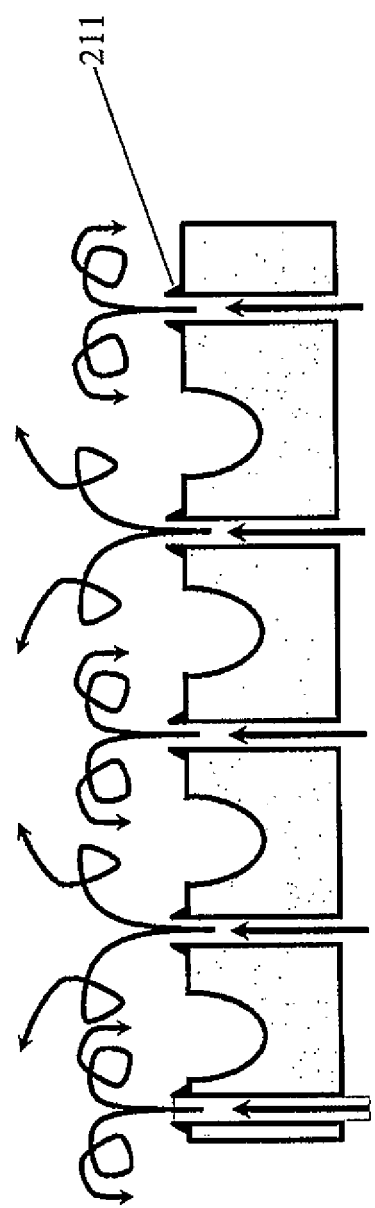
Figure 2H:
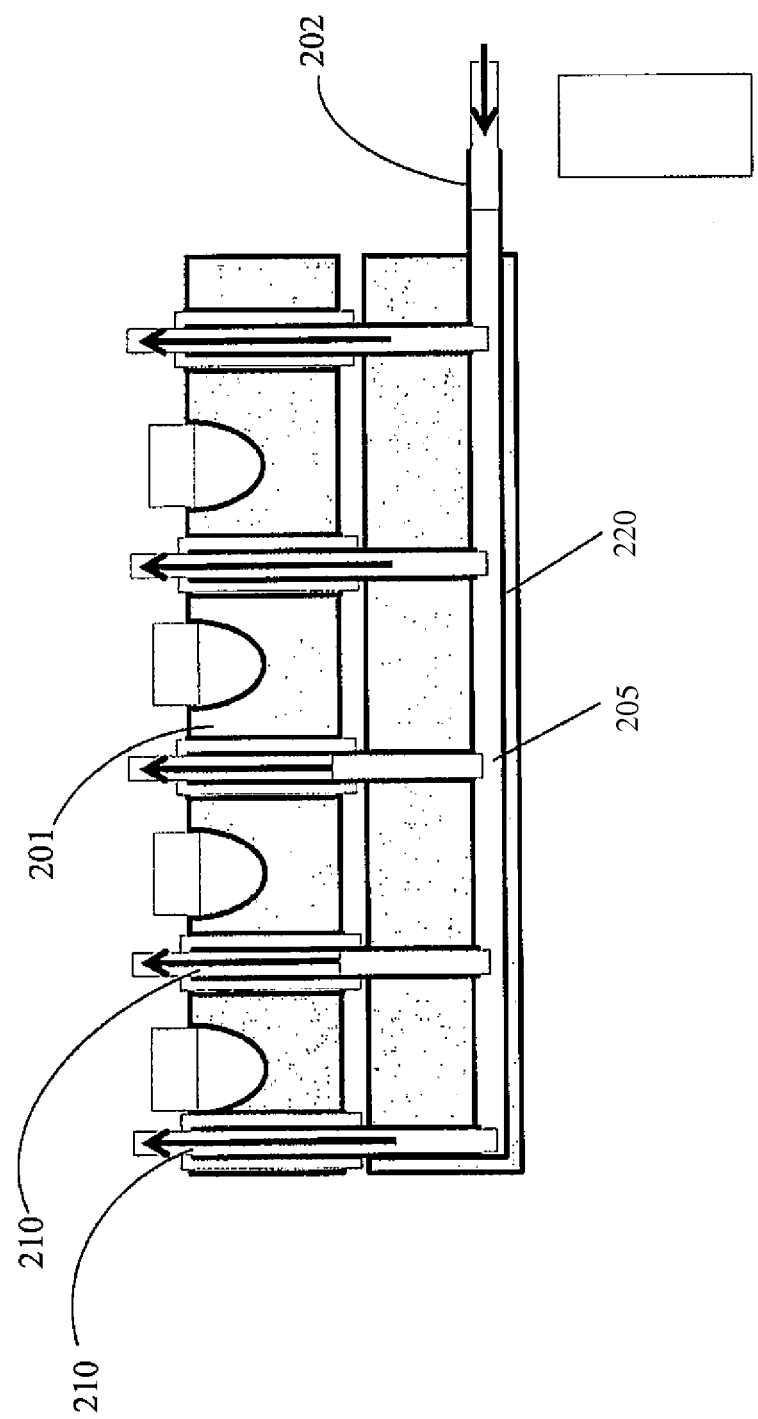

FIG. 2(C) is a top view of the palette 200 of FIG. 2(A). Each gas channel 205 may have a gas outlet 207 on the top surface of the palette. Referring to FIG. 2(D), the gas flow may be through vertical channels 205'. FIG. 2(E) illustrates an embodiment where the channels 205 within the palette 200 are connected to channels 208 of the permanent fixture 209 within the instrument to which the palette docks. Thus vertical gas flow through flow channels between adjacent containers 201 is a continuation of the gas flow and channels formed in the permanent instrument under the palette. Here, the gas may be introduced to the system through an inlet 210 located on the permanent instrument. The palette may be designed such that the openings where the gas leaves the palette are configured in such a way that they assure substantially laminar flow (as opposed to turbulent flow). For example, the shape of the flow channel, and/or the rate of the gas flow may be adjusted to ensure a laminar flow pattern. FIG. 2(F) illustrates a turbulent flow pattern, while FIG. 2(G) illustrates a laminar flow pattern. FIGS. 2(F) and 2(E) show some example features that may influence the flow pattern, but the features are not limited thereto and any suitable features to induce or enhance a laminar flow may be utilized. FIG. 2(H) shows a manifold with gas flow channel 205 and gas outlet 210 located on a permanent fixture 220 of the palette (such as the frame of the palette), to ensure laminar flow over the top of the containers.

Air routed to the palette may be passed through a high-efficiency particulate absorption (HEPA) filter to create an inert or sterile environment around the palette and in its contents. The gas may also be an inert gas.

In one embodiment as described earlier, a palette may have no walls or other vertical barriers to create wells or containers. The fluids and solids are confined to a location within a palette by means other than physical barriers. Such means may include (but are not limited to) surface tension, electrostatic means or thermal control. Surface tension, for example, may be controlled and not constant. Also materials may be moved along the palette by various means either involving caddies or not. Electrowetting techniques may be used as well.

Table 1 lists some features of a palette/caddy system described above that make it unique and distinct from other systems, for example, systems now used in production, analysis and dose dispensing of radiopharmaceuticals.

TABLE 1

Typical distinctive properties of the palette/caddy system any container on the palette may be accessible at any time
all components may be fluidly isolated from one another
processes may happen in any order or in parallel
fluids may or may not be fully contained
liquid losses are not dependent on the transfer distance
material may be transferred from any one location to any other location in any volume
precise metering of specific amounts of liquid sample may be enabled at any step in the process
fluid may not be required to flow in order to move between 2 locations within a palette
no electronic or fluidic connection with the instrument
the topology of the container is fixed, no change of the shape is mechanically actuated by the instrument
no valves, tubing junctions
no moving parts
in a 2-phase liquid-liquid mixture, any layer may be accessible at any time In one embodiment, the palette or its parts may be moved automatically providing for short and/or long-distance transfer of the palette. The long-distance transfer may be utilized in processes such as to deliver the palette behind shields attenuating ionizing radiation. The "movable palette" mechanism may be, for example, useful in injecting new palettes or ejecting used ones from the system. It is also useful in the analytical applications where the liquid transformations within the palette are carried out via caddies in one part of the system for synthesis (such as one part of an instrument), but the analysis of the palette yielding measurements is carried in another part of the system for synthesis (such as another part of the instrument), requiring the entire palette to be moved from one location to another.

The containers within the palette may be configured to house various volumes of liquid, solid or gaseous reagents, or a combination thereof. It will be understood that virtually any reagents may be used with the present system. They can be delivered to the system within the palette and manipulated in a number of ways. In order to reduce or minimize the reliance on precise manual handling, the reagents may be delivered to the system in excess and the system will meter precise amounts as necessary for specific chemical reactions or analyses instead of pre-loading the precise amounts.

The material delivered to the system may be in the form of a pure chemical compound, a mixture of compounds, a solution of a compound, or a solution of a mixture of compounds. The material may be a radioactive compound. It may also be in a form of a compound reversibly adsorbed onto an inert carrier, or reversibly chemically bound to a carrier.

The delivered materials may play any role in the synthesis, analysis and dispensing process, examples of which include: reagent (liquid, solid or gas), reactant, catalyst, phase-transfer reagent, emulsifier, pH buffer, indicator, intermediate, product, byproduct, waste, solvent or absorbent. Some examples may include: $K_2CO_3$; Kryptofix-2.2.2, acetonitrile (MeCN), Mannose Triflate, acids, bases, water or any other gases or liquids.

It will also be understood that the system may be run by an operator via a computer and in some embodiments, may be automated. The system may include a computer and a computer-readable media for storing a program configured to operate the system.

In order to transfer materials from one location to another (from one container on a palette to another container on the same or another palette), a caddy accesses a container on a palette and the material, or a fraction of thereof, is transferred into the caddy. The caddy then moves to the destination and the material in the caddy, or a fraction of thereof, is unloaded. According to one embodiment of the present invention, unlike methods relying on fixed plumbing, the direction of the transfer may be determined during designing of the specific operational program of the instrument, not during design of the instrument. That is, the direction of the transfer may be determined after the design of the instrument. The direction of the transfer may even be determined (or even reversed) in real time during the instrument operation, for instance to correct for minor errors. If a content of a container needs to be delivered to several locations, it does not run through manifolds or distribution valves, but is sequentially or simultaneously aspirated in caddies and delivered to the desired locations.

Further, in the caddy-palette design, the fluid path is fresh and disposable for each transfer, thus eliminating a need for interim cleaning, or other limitations, such as having to follow a specific sequence of the reagents passing through a particular channel. In addition, each transfer may use a caddy best suited for that specific transfer in terms of material compatibility and/or volume being transferred, unlike in other machines, tubes and valves are designed to be used with a set (e.g., a specific) volume and are permanently mounted on the instrument or on the disposable cartridge. The system according to embodiments of the present invention may operate a series of caddies, some used for smaller volumes, others used for larger volumes, thus reducing (e.g., dramatically reducing) losses during liquid transfer.

Using the palette-caddy approach, it is possible to move the material for greater distances than using the traditional tubes and valves. In the traditional machines the longer path is associated with the larger tubing surface the material is exposed to, embodiments of the present invention disclosed here provides for a constant surface area the transferred material is exposed to, thus constant and known losses of the material. Additionally, the surface-to-volume ratio is kept low (e.g., to a minimum).

Additionally, the caddy-palette system allows precise metering of a material during any transfer, as long as the metering is allowed by the system operating the caddies. Other systems, for example, in the field of radiopharmaceutical production, described up to date only allow precise metering for a limited subset of the transfers within the system.

The palette-caddy system may be utilized to perform synthesis of a product, analysis of a product, or dose-dispensing and/or packaging of a prepared product. Such product may be a radiopharmaceutical. Yet in another embodiment, the system is used for all these purposes or any combination thereof: synthesis, analysis and dispensing. The processes occurring in each container are independent and, with certain precaution, any possibility of cross-contamination can be eliminated. Individual conditions can be created with one palette or for several palettes processed at the same time. The part of the machine operating caddies may operate several caddies at the same time. These features may allow for parallel processing of several samples/performing several parallel syntheses, which is an enhancement over the fixed plumbing systems, which are only capable of performing one or very few processes at the same time. In another embodiment the system is configured to fill containers designated to deliver doses of product to specific patients at specific calibration times.

Existing instruments for the production, QC and dispensing of a radiopharmaceutical product do not provide for easy integration of all these functions, since that would require connecting them physically with fluid paths and operatively with a program code. Within a system according to embodiments of the present invention, distinct hardware components would enable the 3 different processes. The system described here may use the same set of stationary hardware to accomplish all 3 processes (potentially even within the same palette).

In all of the embodiments listed above the amount of waste generated during the operation can be reduced or minimized. The main source of waste generated by a radiochemistry instrument is the washing liquid used to clean a fluid path. As a liquid path does not need to be cleaned in the palette-caddy system, the chemical waste is limited to the reagents used in the synthesis/analysis. Thus the waste stays where it is generated and is disposed of together with the palettes and caddies.

The waste may be segregated according to the specific hazards, for instance radioactive waste and regular waste. Operational expenses may be reduced (e.g., significantly reduced) by reducing the amount of more hazardous waste generated.

One palette may support one or more complete processes (synthesis of one product, analysis of one product, and/or another complete process) or sub-processes (a process that contains one or more operations where more than one palette is used for a complete process) whereas a caddy may support one operation (such as moving reagent from one location to another) before it is disposed. The rest of the system may be permanent. The only components that are exposed to reagents/samples are palette and caddy (both of which may be disposable).

In one embodiment, the system using palettes and caddies is self-sufficient, that is, performs a complete synthesis or analysis.

In another embodiment, the system using palettes and caddies includes (or is integrated with) other machinery to complete the synthesis or analysis. This integration may be achieved via electronic data transfer and/or physical transfer of the material between the machine using palettes/caddies and other machines.

In embodiments where the system is used for chemical (or radiochemical) synthesis, a palette loaded with all reagents is inserted into the instrument. An auxiliary empty palette may also be loaded. Then via the use of caddies, the reagents are moved from one location to another in sequences and volumes predefined by a program being executed, in order to implement a series of chemical transformations.

In order to facilitate certain chemical transformations, temperature may be controlled in specific areas of the palette or the entire palette. This may be effected by a heating/cooling element embedded in the part of the permanent instrument in direct contact with the palette. Individual caddies can be temperature controlled too.

Separation of Chemical Compounds

Chemical transformations may include separation of chemical compounds. Separation (purification) of the chemical compounds in a palette-caddy system may be enabled through the utilization of filters, evaporation of liquids, liquid-liquid extractions, absorptions of selected molecules, and/or other suitable methods. For example, either the palettes or caddies may contain filters (or other forms of solid phase), operated in a way allowing the solution to be passed through a filter as it is pulled into the caddy or pushed into a new location on the palette.

Evaporations may be enabled via thermal control of specific locations within a palette and/or applying moving gas at a specific location to remove vapors.

Liquid-liquid extractions may be enabled by generating two liquid phases within one location on a palette or within one caddy. In the former case, a caddy can pull in only one of the two phases (either top or bottom layer), while in the latter it can dispense one phase at one location and the second phase at a different location.

Absorption of selected molecules from solutions can be performed using palette containers filled with sorbent or caddies containing sorbent. The sorbent may be an ion-exchange resin for absorption of fluoride anion, C-18 modified silica for extraction of the non-polar solutes, polar resins for extraction of the polar solutes, etc. Other phase separation methods may be used with the present invention.

In addition, a palette or a caddy may contain a chromatographic fixture designed to operate as high-performance liquid chromatography (HPLC), gas chromatography (GC), thin layer chromatography (TLC), electrophoresis or the like. However, the process is designed such that the purifications are enabled via simpler techniques (such as filtration or adsorption/desorption).

Radiosynthesis Application

Figure 6:
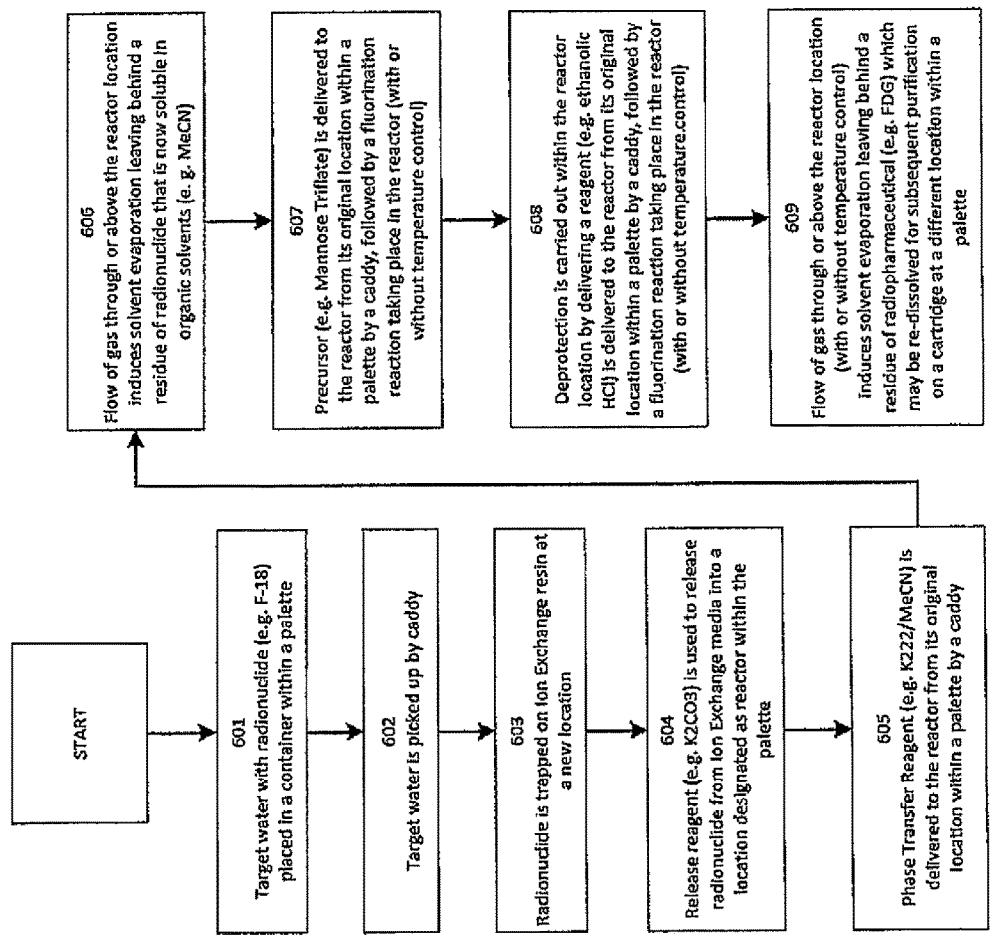
FIG. 6 is a flow chart showing a method of synthesizing a radiopharmaceutical according to one embodiment of the present invention.

As an example, the present system may be used to synthesize a radiopharmaceutical. FIG. 6 is a flow chart illustration such a synthesis process. First in act 601, a target water containing a radionuclide may be placed in a container within a palette. Then in act 602, the container with the target water is picked up into a caddy and delivered at a new location on the same palette, or a different palette. The target water may then be passed through a bed of ion exchange resin to separate the radionuclide out of a dilute solution in act 603. A suitable compound, such as $K_2CO_3$ may then be used to release the radionuclide as a concentrated solution into another container or a reactor within the palette in act 604. Next, a suitable compound, such as a K222/MeCN solution, may be delivered from its container (for example, a container on a palette) to the reaction location in act 605. After the reagents have been mixed, nitrogen may be delivered to induce solvent evaporation (with or without concurrent heating) leaving behind a residue containing a complex containing the radio-active atom, for example, an [F-18]KF/K222 complex in act 606. Next, a precursor (for example, mannose triflate) may be delivered to the reactor in act 607. Deprotection may then be carried out by delivering a suitable compound, such as ethanolic HCl, into the palette container used as the reactor in act 608. Here, the reaction mixture may be heated. Then in act 609, the solvents may be evaporated, leaving behind a residue including the radiopharmaceuticals, which may be re-dissolved in water for subsequent manipulations such as cartridge purification. Alternatively, instead of evaporation, the solution including the radiopharmaceuticals may be diluted with water. Subsequent purification of the radiopharmaceuticals may be carried out by passing the crude solution through a series of cartridges. While the above example of a process used to synthesize radiopharmaceuticals using a palette-caddy system has been described with a set of acts, such a process may not include all of the acts, and the acts may not need to be executed in the specific order as described. Instead, one or more of the acts may be omitted, and one of more of the acts may be combined.

For example, a palette-caddy system may be utilized for the synthesis of fludeoxyglucose (18F) (FDG). First, [F-18] fluoride-containing target water may be placed in a container within the palette. Then it is picked up into a caddy and when it is being delivered at a new location, it is passed through a bed of ion exchange resin to trap [F-18]fluoride out of a dilute solution. $K_2CO_3$ may then be used to release [F-18]fluoride as a concentrated solution into another container or a reactor within the palette. Next, a K222/MeCN solution may be delivered from its container to the reaction location. After the reagents have been mixed, nitrogen may be delivered to induce solvent evaporation (with or without concurrent heating) leaving behind a residue containing an [F-18]KF/K222 complex. Next, the precursor (mannose triflate) may be delivered to the reactor. In processes where the volume of $K_2CO_3$ solution is substantially small, no evaporation may be necessary allowing direct addition of the solution of precursor and phase transfer reagent in an organic solvent to the concentrated aqueous $K_2CO_3$/[F-18] KF solution followed by fluorination reaction. This is an enhancement because such scenario avoids the need for evaporation steps which take time and may lead to some decomposition products. A palette-caddy system enables this scenario by the absence of the need for using larger volumes of water (required for long-distance transfer through tubes in conventional systems).

Deprotection is then carried out by delivering ethanolic HCl into the palette container used as a reactor. Once again, the reaction mixture may be heated. Then, the solvents may be evaporated, leaving behind a residue of FDG which may be re-dissolved in water for subsequent manipulations such as cartridge purification. Alternatively, instead of evaporation, the FDG solution may be diluted with water. Subsequent purification of FDG may be carried out by passing the crude solution through a series of cartridges.

Using the palette-caddy system, microliter samples may be synthesized in each container and ready for transferring to a desired location. Alternatively, a large volume of samples may be synthesized in a container of the palette, and microliter sized samples may be picked up from the container and transferred and dropped off at a desired location utilizing a caddy.

Analytical (Quality Control) Application

As aspect according to embodiments of the present invention is directed toward a method for assessing one or more quality control (QC) parameters of a radiopharmaceutical. In one embodiment of the present invention, the one or more QC parameters is assessed with a palette being a multi-well plate. Yet in another embodiment of the present invention, the one or more QC parameters is assessed using a palette containing reagents on solid support. Yet in another one embodiment of the present invention, the one or more QC parameters is assessed with a palette being an assembly of individual containers.

In one embodiment a plurality of parameters being measured may include: sample color, turbidity, pH, a phase transfer reagent concentration, pyrogenicity, radio-isotope half-life, radioactivity concentration, organic solvent content, sterility or any combination or subset thereof. Yet another embodiment of the present invention is directed to the method described above wherein when the outcome of one or more measurements is accepted, the sample is accepted on the criteria of one or more parameters.

In an embodiment where the system is utilized for analysis, a palette is loaded with all the reagents necessary for multiple analytical procedures. An empty palette may also be loaded. Typically these are chemicals or materials whose interaction with the sample generates a signal that can be correlated to a specific chemical or physical property of that sample. The signal is an optical signal that is detected by a detector which is not in physical contact with the palette. In one embodiment, a light source and a spectrophotometer are used to generate and read optical signals. Using PET radiopharmaceuticals as an example, there are typically more than 10 parameters along which the product needs to be analyzed and the results accepted before the product may be used for human administration. In this case reagents that are contained at different locations within the palette are designed to yield signals corresponding to the required properties. The sample is the last material added to the palette before the latter is inserted into a stationary system, i.e., the analytical instrument. Alternatively, the sample may be distributed in specific amounts between different locations within the palette via the use of caddies after being inserted into the stationary system. In each of these locations a transformation takes place generating a signal that is correlated to a specific property. In some embodiments such signals are relayed to the stationary instrument without any part of the latter coming in contact with the sample or reagents. A separate set of locations on the same palette can be used for calibration purposes, ensuring the calibration is always performed using the same batch of reagents as for the analysis. That value is then assessed against a limit or a range in order to deem that property acceptable or not acceptable according to pre-defined criteria. At the end of the process a multi-parametric report is generated and the palette can be disposed. In one embodiment the invention allows an operator to run several iterations of a process in parallel to assure increased accuracy or validity of the resulting measurement.

In one embodiment of the present invention, the phase transfer reagent is being analyzed and the phase transfer reagent is Kryptofix2.2.2.

FIG. 1 is a flowchart of an operational process according to an embodiment of the present invention (for analysis applications). The sequence of operation may be stored on a suitable electronic storage medium, such as a computer-readable medium, which may be non-transitory, or RAM or ROM, or EEPROM or any other suitable electronic storage medium that can store electronic data. The operation may be object code, source code, or stored on a dedicated storage medium, either local to the user device or at a remote location and accessed as desired. Thus, the operation may be considered a module when stored and/or accessed and/or retrieved, regardless of the type of storage medium.

As shown in FIG. 1, the process may be directed to quality, control of a sample along three parameters: A, B and C. It is though understood that the number of parameters may be less (e.g., two) or greater. At the start of the process, the system recognizes the palette that is inserted into the instrument, and pulls from the palette information about the product that needs to be analyzed. That is, the system may access the sample and the information on which parameters the sample needs to be assessed. For example, a recipe for analysis along parameters A, B and C is pulled up. The material is then transferred within the palette according to the recipe, and the analysis is conducted in a plate reader. The parameter C is assessed via a test, which yields a numerical value that is correlated to some sample property. If the value is within acceptable range, the sample is considered acceptable by parameter C. The parameters A and B are assessed similarly using a respective test, correlating some sample property to a numerical value. If the numerical value for each test falls within a predefined range, the sample is considered acceptable by both parameters, A and B. If the value of any of parameters A, B or C is outside the specs, the sample is rejected.

It is also an embodiment of the present invention that disposable components may be identified and those components are discarded, or disposed of following the assessing of the sample (such as a radiopharmaceutical).

In one embodiment, a palette contains a receptacle configured to accept and hold a vial. This is valuable for easy addition of analyte sample to a palette with all the reagents already in it and without the need to dispense the analyte (which may be radioactive) by hand via a syringe. In yet another embodiment the palette contains a plurality of wells with or without reagents and one or more receptacles where vials may be inserted. Such vials may be empty or filled. They may be capped or open and may contain reagents or analyte. It is possible to package a palette with all the reagents and an empty sealed vial (which may also be sterile). The user would then open this package shortly before the analytical application of the palette. The empty sealed vial may then be removed from the palette and placed within radiation shield where it would be filled with analyte sample. Then the vial may be placed back into the palette and the palette may be inserted into the system that uses it to analyze the sample. The sample may then be taken out of the vial and distributed to other locations within the palette by caddies. A vial may need to form a tight fit with the receptacle so that it does not fall out or cannot be accidentally pulled out of the palette by a caddy.

It is also possible to locate the receptacle for the analyte vial within the permanent instrument in a location not associated with a palette.

In another embodiment, the palette is designed in such a way that the insertion of a container (vial) triggers other events. An example of an event may be breaking the well seal or mixing the reagents. Or potentially if the palette is installed in an instrument at the time of vial insertion, such insertion may trigger the start of the analytical process.

It should be noted that palettes containing both permanent containers (e.g. wells) and removable containers (e.g. vials) have not been used to date since their use is counterintuitive. The prior art relies on either plates with wells or racks with vials but not combinations thereof.

It is also possible to use a palette where one of the wells does not have a floor and is effectively an unrestricted see-through opening. This opening may be used to hold a vial or for other purposes.

In an analytical application that requires a plurality of reagents, not all the plurality of the reagents may be compatible with the same palette material. According to one embodiment of the present invention, a palette may have a plurality of regions and each of the regions may be made of different materials, each compatible with a set of reagents, to accommodate a diverse reagent set. The plurality of regions may be connected together through welding, gluing, one inserted into an opening or slot in the other, or any suitable connecting mechanisms. Other plates with reagents usually carry similar reagents which are all compatible with the material chosen for the specific plate. In one embodiment, a palette contains both organic and aqueous reagents. In another embodiment, the palette is made of a single material which is coated with a protective film (completely or partially) to protect the palette material from reagents which it is not compatible with.

In another embodiment a palette includes containers of different sizes and shapes. Size variability is dictated by the fact that different tests require different amounts of reagents. Whereas, shape differences may be necessary to optimize different detection methods used for different tests. Also, typically when multi-well plates are sealed, the seal covers the entire plate and seals all wells uniformly. In case of palettes, different locations may require different seals. Also some locations may be sealed while others are open. It is also possible to use a palette with standard/uniform well size but utilize inserts into wells that reduce the volume of different wells down to different final volume. Such inserts may be designed to hold a certain volume of liquid, solid, or gas or to displace a certain volume of liquid, solid, or gas.

In another embodiment, the palette may contain components necessary for chromatography, for example, an HPLC injection loop. The added HPLC injection loop onto the palette may be considered as one of the containers. It may or may not have valves. In one embodiment its use would be the following. The loop is filled by a caddy with analyte while the palette is in one location. Then the palette is moved to another location where the loop ends up being in-line with the HPLC stream. This would allow the contents of the loop to be injected onto an HPLC column (which may or may not be located within a palette).

In another embodiment, a palette contains a septum-piercing device. This device may be used to pierce seals of individual locations (or containers) within a palette. It may also be used to add sealed vials to the palette in a way that deposits their contents into a location within the palette.

In another embodiment, the palette may have caddies packaged together with it or a palette may contain caddies. Such palettes may or may not contain reagents. The palette packaged with caddies (either within containers or next to them, either in 1:1 ratio or in other ratios) allows the analysis to be performed faster and for the user to control the cleanliness of the caddies to a greater extent.

In yet another embodiment, the palette contains hardware that plays a role in optical detection. One embodiment of such hardware is a lens that modifies the optical signal. In another embodiment a light source or detection apparatus may be completely or partially contained within a palette. Such palettes may or may not be packaged with reagents. It is possible to use one type of palette to deliver the reagents and another type of palette to carry out the analysis.

In another embodiment, the palette includes a built-in mixer that effectively mixes 2 liquids or a liquid and a solid. Such mixers may or may not be activated by one or more caddies. The mixer may be activated pneumatically, optically, mechanically, thermally or electrically.

In another embodiment, a palette designed for radioactive applications contains some radiation shielding in it. Such shielding may be necessary to either protect the user or to separate signals from different parts of the palette from one another to reduce noise in the measurements or "cross-talk". Such shielding may be permanently included in a palette or it may be removable. It is also possible that the shielding configured to protect a palette or part of it stays permanently mounted within the instrument while the palettes (standard or custom) may be inserted and removed without moving the shield. In other embodiments the system is designed such that cross-talk between radioactive signals from locations within the same palette is eliminated without using any shielding, an example of which is to be explained in more detail later under the section about Radioactivity concentration (7).

In embodiments, the palettes are designed in such a way that they can receive the sample of analyte without a port of any kind. The sample may be added to the well or vial without port or tubes. The sample may also be delivered in a sealed vial. In contrast, other analytical systems require an injection port. It is also to be noted that any location within the palette may accept the analyte, whereas in traditional analytical instruments with ports there is only one specific location that may accept the sample (injection).

In one embodiment, a palette is packaged with reagents that, when mixed with the analyte, produce measurable optical signals. In another embodiment, palettes are also designed to carry reference standards, which are known materials to which the analyte is to be compared. Such reference standards may be used to perform calibrations of various components of the system. They may also be used to perform daily system suitability testing. For example, a reference sample may be injected into an HPLC sub-system prior to the analyte, resulting in a chromatogram. This chromatogram is then evaluated to validate proper performance of the instrument prior to analyzing the real sample.

In one embodiment, there is a system of recognition between the instrument that operates palettes and caddies and the palette. The instrument may uniquely recognize the palette. A palette carries not only reagents but also information. This may be information about both the method that the specific palette is intended to use in its operation and information about the product/analyte being analyzed, date, user serial number and other sample-, method-, user- or facility-related information (or any other information).

There may be a number of ways of carrying this information, while the palette is the carrier of both chemicals and information.

The methods of carrying information include but are not limited to: (a) bar-code, (b) electronic media, optical signals and other information-carrying methods.

One way of carrying information that is unique to palettes is that the configuration of filled and empty wells may be used as a record of information that is interpreted by the instrument. The instrument may sense this information in a plate reader or by caddy interaction. This way the palette contains no extra features other than chemicals, but whether the chemicals are placed or absent in one or more given location may have a meaning that may be interpreted as information (e.g. regarding method, analyte, etc.).

Other configurations of a system may have separate palettes for liquid and solid reagents. Alternatively, these may be components of one palette. One part of the palette gets filled/sealed with solids in one process, while the other is filled/sealed with liquids in another process. Afterward these two (or more) components are combined to form one palette.

In another embodiment, an analytical system relying on palettes/caddies is configured to accept a sample of analyte in a syringe.

There is a method of using the palette to analyze sample where some tests are performed immediately upon distribution of liquids/reagents while others are performed at a later time. During the time between liquid distribution and delayed reading, the palettes may be stored in a temperature and/or air controlled environment (e.g. an incubator).

Another method involves some of the tests to be performed on a palette within the instrument that distributes liquids while for other tests the palettes are sent to another facility which has different analytical equipment. But the results of the remote analysis are included in the complete report for a specific sample.

A method of using a palette system for quality analysis according to one embodiment of the present invention is described in more detail below.

It is to be noted that besides the enhancement of each individual test method described below, the palette technology uniquely enables further enhancements which include (but are not limited to): (a) multiple (replicated) readings for each test; and (b) replicated samples for each test, (c) reference standards, (d) calibration solutions for spectrophotometer, and (e) reference standards for HPLC, all pre-packaged on a palette. It is to be noted that methods according to embodiments of the present invention require no human judgment or subjectivity. The machine has a precise algorithm by which the sample is deemed acceptable or not even in borderline situations, which is not possible with subjective tests with human decision-makers.

Table 2 is a summary of the typical quality control tests for radiopharmaceuticals and the current existing method used. As shown in Table 2, all the tests use different test methods and require different devices and pieces of equipment in order to be carried out. Therefore, it is not possible to combine these tests in one system. In contrast, by utilizing a suitable reagent that reacts with the radiopharmaceuticals and generate an optically detectable signal that can be correlated with one or more of the quality control parameters, embodiments of the present invention enable two or more of the quality control tests to be conducted utilizing a plate reader. A system according to one or more embodiments of the present invention allows a number of the quality control tests to be conducted simply utilizing one palette and one plate reader.

Determination of the Radio-Pharmaceutical Sample as being Either "Colored" or "Colorless" (1)

Figures 13A, 13B, 13C:
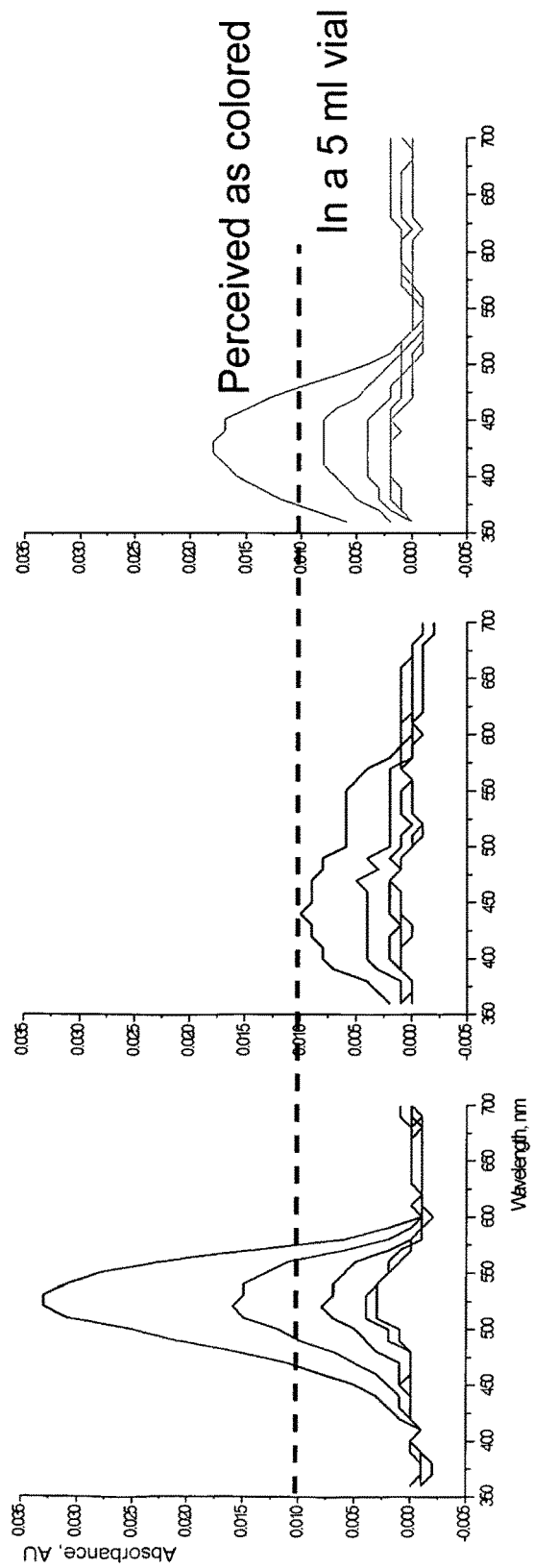
FIGS. 13(A), 13(B) and 13(C) each shows UV-Vis absorbance versus wavelength for a set of colored samples with various dilutions measured in a plate reader.

Determination of the radio-pharmaceutical sample as being either "colored" or "colorless" (1) is accomplished according to the current embodiment of the invention by filling one (or more) of the locations within a palette with pure undiluted sample of analyte and passing visible light through that well within a spectrophotometer measuring the absorbance of light by the sample at different wavelengths of the visible light spectrum between 360 and 700 nm. In contrast, current colored/colorless determination is being performed by visual inspection with a human eye. It has been determined experimentally that a human eye cannot detect color if a liquid sample with the thickness of 3 cm with optical density below 0.01 AU/cm (absorption units) at any of the visible wavelengths is presented against a white background. Therefore if the sample does not absorb more than 0.01 AU/cm at any wavelength it will be classified as colorless. Meanwhile, if absorption above 0.01 AU/cm is detected at any wavelength, the sample will be classified as colored and will fail the color test. It is to be noted that this test according to this embodiment of the present invention includes all wavelengths of visible light and not a selected few as in other techniques. Therefore the reliability of this method is better (e.g., superior) to other techniques. Unlike a human eye, this method yields a quantitative traceable result that has no variability between users. It is to be noted that while the assessment by human eye may detect the presence of color, it cannot quantify it. The method described here allows wavelengths and intensity of color absorption to be recorded. FIGS. 13(A), 13(B) and 13(C) each shows UV-Vis absorbance versus wavelength for a set of colored samples with various dilutions measured in a plate reader using Synergy plate reader from Biotek. Here, the set of colored samples was diluted until no color could be detected by two observers. The samples were contained

TABLE 2

| | Parameter | Current Test | Specification | Typical result | Current Method |
|---|---|---|---|---|---|
| 1 | Color | Appearance test: color | visually colorless | visually colorless | Manual |
| 2 | Clarity | Appearance test: particulate | visually clear | visually clear | |
| 3 | pH | pH paper test | 5.0-7.5 | 6.4 | |
| 4 | Kryptofix 2.2.2 concentration | K222 Iodine vapor spot test | <50 µg/mL | <50 µg/mL | |
| 5 | Radionuclidic purity | Half-life measurement | 105-115 min | 108 min | |
| 6 | Radioactivity concentration | Rad signal/volume ratio | 1-50 mCi/mL | 46.8 mCi/mL | |
| 7 | Pyrogen concentration | Charles River endotoxin test | <22 EU/mL | <1 EU/mL | Endosafe reader |
| 8 | Radiochemical Identity | HPLC % RSD of Standard | <10% | 1.70% | HPLC |
| 9 | Radiochemical purity | Radio-HPLC AUC | >95% | 100% | |
| 10 | Specific activity | HPLC UV/Rad AUC measurement | >0.4 Ci/µmol | 13.4 Ci/µmol | |
| 11 | Organic solvents | GC analysis (% v/v) | EtOH: 4.0-10.0% Acetonitrile: <0.04% | 8.70% 0.00% | GC |
| 12 | Sterility | 14-day post-injection culture test | no visible growth | no visible growth | Manual |
| | | Sterile filter membrane integrity test (% pressure drop) | <40% | 18% | |

Conducting the quality control tests utilizing a palette-caddy system according to embodiments of the present invention are as following.

in a PS flat bottom 96-well plate with 275 mkl (microliters) of liquid in each well. Similar results were obtained using a PS flat bottom 384-well plate with 100 mkl of samples in each well.

Determination of the Radio-Pharmaceutical Sample as being Either "Clear" or "Turbid" (2)

Determination of the radio-pharmaceutical sample as being either "clear" or "turbid" (2) is accomplished by filling one (or more) of the wells within a palette with pure undiluted sample of analyte and passing visible light through that well within a spectrophotometer measuring the absorbance of light by the sample at different wavelengths. These measurements are then compared to a series of turbidity standards with known concentrations of insoluble materials. It has been determined experimentally that a human eye cannot detect turbidity in a liquid sample below 0.1 AU (absorption units) at any of the visible wavelengths. Therefore if the sample does not absorb more than 0.1 AU at any wavelength it will be classified as clear. More to that, its absorbance measurement will be compared to standards with borderline concentrations of insoluble materials (just below and just above the threshold). All samples below the threshold will be classified as clear and pass the clarity test. While all samples with measurements above the threshold will fail the test. However, this test will provide more than pass/fail information. It will yield a measurement of insoluble materials and quantify it. This will allow the users to see trends in sample measurements and determine how close or far they are from the pass/fail threshold. Unlike a human eye, this method yields a quantitative traceable result that has no variability between users. It does not just distinguish clear samples from turbid, but provide a quantitative measurement of turbidity.

In another embodiment the color and clarity tests are combined. Traditional approach to evaluation of liquid sample appearance relies on separate assessment of color and clarity. Color might be quantified via light absorption; clarity is normally detected via light scattering. These two measurements require two distinctly different optical schemes, one requiring detector in line with the light source (absorption) and another using detector at an angle to the light source (scattering).

Inventors of the present application noted that the amount of light coming to the detector in line with the light source would be diminished in case of not colored, but scattering sample. In effect, an absorption measuring system will find absorption in colorless but scattering liquid. Based on this observation it is possible to reject QC samples not conforming to the appearance standards, although this experiment alone will not determine whether color or clarity had failed.

Further investigation of the absorption spectra might reveal if it indeed was colored or only turbid. Apparent absorption spectrum of a turbid liquid has a shape of exponential decay, while colored spectrum inevitably has more features, corresponding to the preferentially absorbed wavelength. Simple fitting of absorption spectra with exponential function will result in good fit (chi2~1) in case of scattering sample. In case of the colored sample the fit will be poor (chi2<<1). A threshold for the fit quality can be set to determine if the sample is only turbid, or it is also colored.

Figure 7:
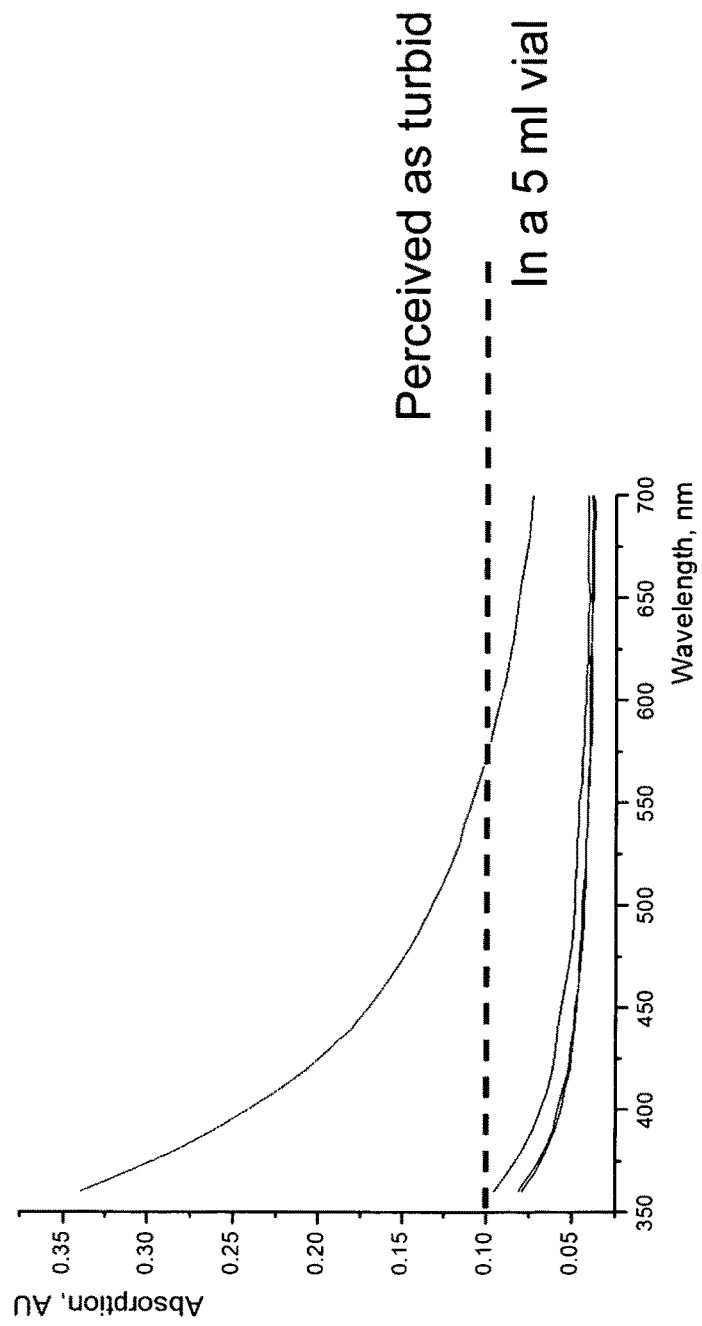
FIG. 7 shows UV-Vis absorbance versus wavelength for a turbidity standard sample with various dilutions measured in a plate reader.

When the total absorption of light by a sample is measured across all wavelengths, it is possible to set a threshold, for example, 0.10 AU, below which the sample may be considered both colorless and clear and one test will replace two. FIG. 7 shows UV-Vis absorbance versus wavelength for a turbidity standard sample with various dilutions measured in a plate reader using Synergy plate reader from Biotek. Here, the turbidity standards were diluted until solution was perceived as clear by two observers. The samples were contained in a PS flat bottom 96-well plate with 275 mkl of liquid in each well. Similar results were obtained using a PS flat bottom 384-well plate with 100 mkl of samples in each well.

Determination of the pH (3)

Figure 8B:
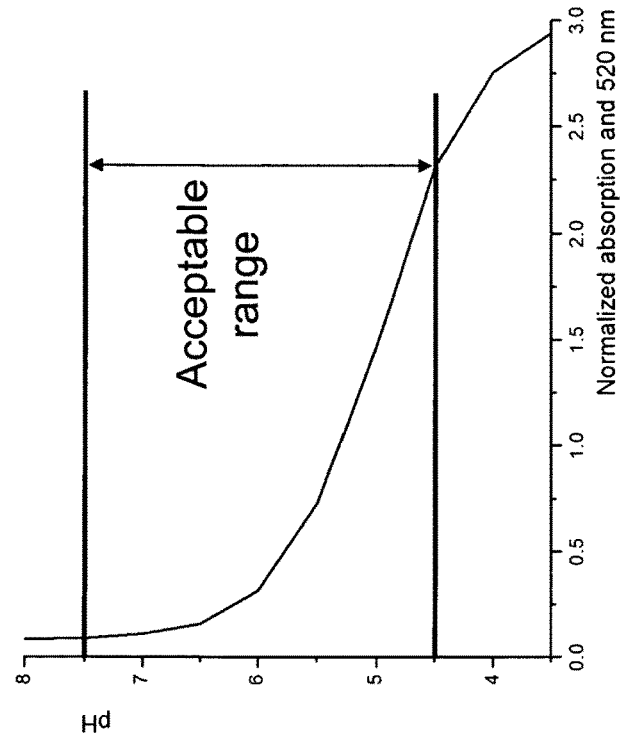
FIG. 8(B) shows the pH value of a sample with Methyl Red pH indicator versus normalized absorption at 520 nm.
Figure 8A:
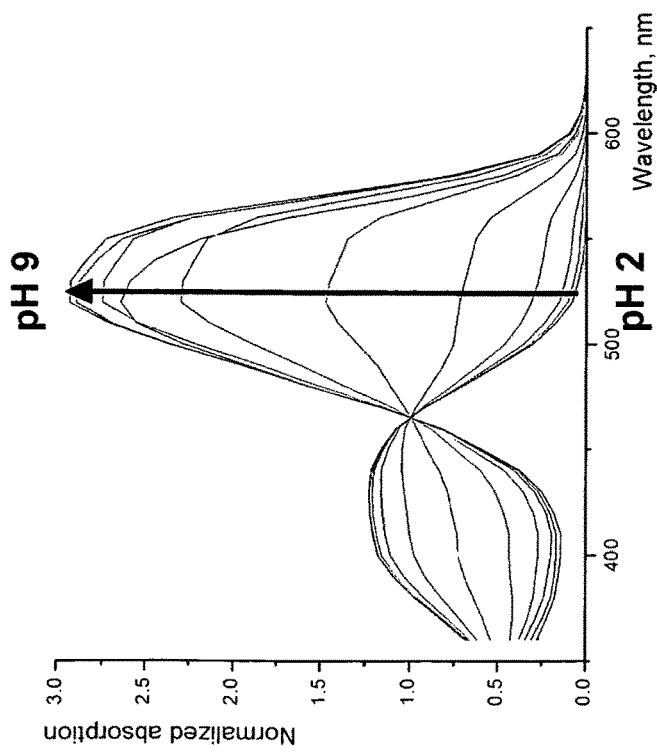
FIG. 8(A) shows normalized UV-Vis absorption versus pH value of a sample with Methyl Red pH indicator.

Determination of the pH of the sample (3) is carried out by mixing the sample in one of the wells of a palette with a pH indicator such as (but not limited to) Methyl Red. The acceptable pH range for a radiopharmaceutical sample is between 4.5 and 7.5. Typically, this is determined by manually spotting an uncontrolled amount of sample on a pH strip and comparing it to a reference visually (eye-balling). In an embodiment of the current invention a set (e.g., a specific) amount of sample is mixed with a set (e.g., a specific) amount of indicator and the resulting color is measured on a palette by a spectrophotometer with light passing through the well and absorbance being measured. The intensity of the resulting absorbance, measured at a set (e.g., a specific) wavelength (e.g. 525 nm) is correlated with a precise pH of the sample. As in the other tests, this measurement is precise, subjective, traceable and user-independent. FIG. 8(A) shows normalized UV-Vis absorption versus pH value of a 200 mkl sample with Methyl Red pH indicator; and FIG. 8(B) shows the pH value of a 200 mkl sample with Methyl Red pH indicator (25 mkl) versus normalized absorption at 520 nm. As shown in FIG. 8(A), the normalized absorbance changes as the pH values changes from 2 to 9. As further shown in FIG. 8(B), the pH value of a sample can be obtained based on the normalized absorption at 520 nm. Spectramax from Molecular Devices was utilized and the samples were put in a PS flat bottom 96-well plate. Similar result was obtained using Synergy plate reader from Bioteck on a PS flat bottom 384-well plate with 5 mkl indicator and 90 mkl sample.

Kryptofix Quantification (4)

Kryptofix (2.2.2-cryptand) is used as a phase transfer catalyst in the production of most fluorinated radiopharmaceuticals, including 18F-FDG. It is, however a toxic compound, and FDA mandates testing of each batch for potential residual kryptofix. The upper QC limit is 50 mg/L, approx $1.3 \times 10^{-4}$ mol/L.

Current method for kryptofix quantification is poorly amenable for automation. It relies on a reaction between kryptofix absorbed on a solid support (TLC plate) and iodine vapor or other source of iodine. The method critically relies on a "revelation plate". A blue solid compound is formed and then an operator checks this color against positive and negative controls. As such, it is not possible to use such method for a solution-based measurement, for example, it is not possible to use the "indicator" (i.e., the blue solid compound) for a solution based measurement. The volume of samples is not controlled, the time or uniformity of Iodine exposure is not controlled and the comparison is subjective. This method is difficult to automate due to the problems associated with measuring spectrum of reflected light, unstable color produced in the reaction and complex automation of the sample application to the solid support, unstable reading over time, confounding factors influencing spot intensity, and reflectance reading complicated by scattering and nature of support. Also, the current method is not really a method for determination of kryptofix. Rather, it is a method for determination of tertiary amines with no selectivity to a particular amine.

An embodiment of the present invention uses a solution-based color test to circumvent the problems associated with the above referenced current method. The test is based on a competition for metal ion between kryptofix and another chelator. If the competing chelator changes its spectral properties upon chelation, this will constitute the basis of analysis. The ratio between the free chelator and chelator-metal complex will define the absorption spectra of the solution. In the presence of kryptofix, metal ions will partially bind to kryptofix, increasing relative concentration of the free indicator. This will produce spectral shift detectable by the plate reader in the absorbance mode.

Kryptofix is known to bind three different types of metals: potassium; strontium/barium/calcium; and heavy metals such as Pb and Hg. All these metals can be detected colorimetrically and the respective indicators are commercially available.

Kryptofix was specifically designed to bind potassium preferentially over other alkali metals. One embodiment of the present invention utilizes this feature to design a kryptofix detection system that includes eriochrome black T, a color indicator for potassium, and potassium chloride. The analysis may be performed, for example, in a mixture of water with organic solvent such as ethanol or DMF, to stabilize eriochrome T in the solution.

In another embodiment, Xylenol orange may be used in combination with Ba and/or Sr cations. An added enhancement of this approach would be the absence of these cations in the original QC sample. An alternative approach might be using fluorescent indicators for Ca, such as FLURA-2 or INDO-1. This will require a plate reader capable of fluorescent measurement, a common feature of the plate readers equipped with luminescent detector. Ca-fluorescent approach would offer a high (an extremely high) sensitivity and low background.

Figure 9:
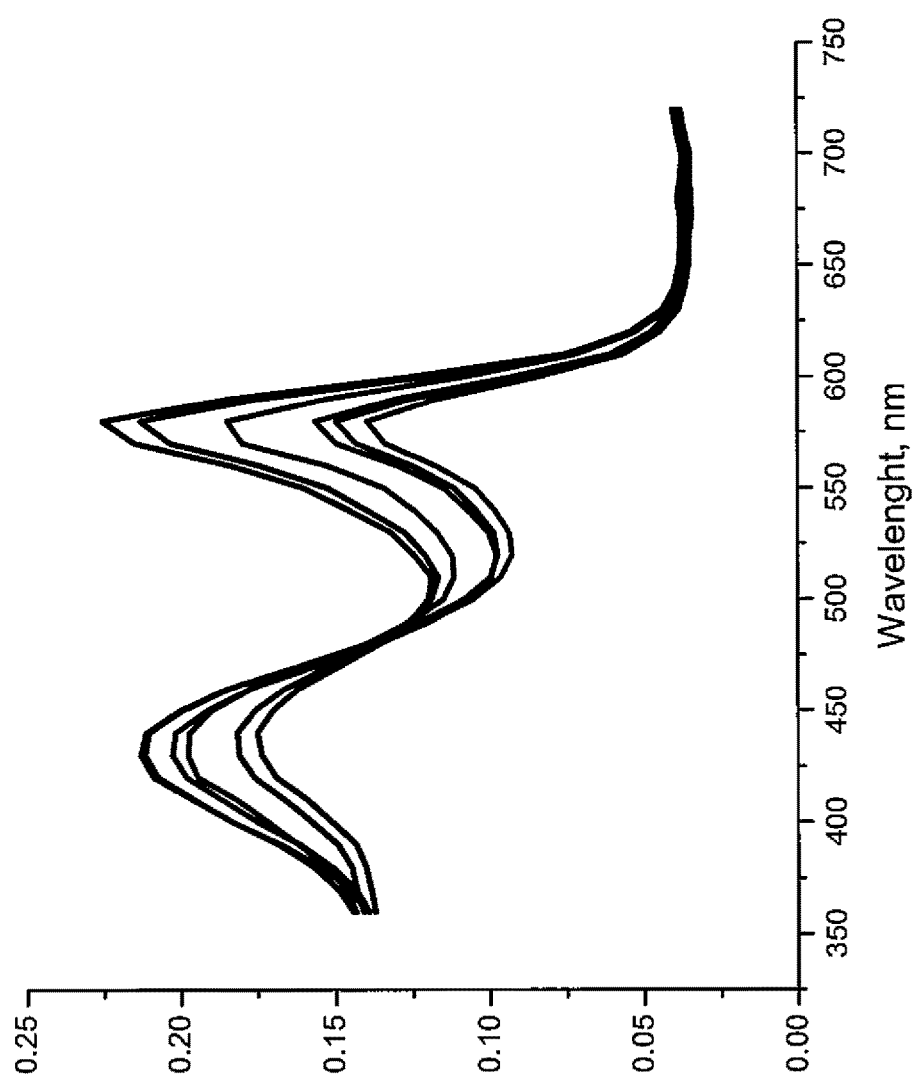
FIG. 9 shows UV-Vis absorbance versus wavelength for various concentrations of Kryptofix.

In an embodiment of the current invention, a set or specific amount of sample is mixed with a set or specific amount of metal salt and the respective metal indicator and the resulting color is measured on a palette by a spectrophotometer with light passing through the well and the absorbance being measured. The intensity of the resulting absorbance, measured at a set or specific wavelength (e.g. 540 nm) is correlated with a precise K222 concentration in the sample. As in the other tests, this measurement is precise, objective, traceable and user-independent. It has been validated experimentally and demonstrated reproducible results in the range of K222 concentrations between 0 and 5000 mg/L. The method is capable of determining exact concentration of K222 and perform pass/fail assessments in the borderline cases with concentrations very close to 50 mg/L. FIG. 9 shows UV-Vis absorbance versus wavelength for various concentrations of Kryptofix. In FIG. 9, series of absorption spectra of (Ba2+/Xylenol orange) mixture in the presence of various concentrations of K222, from 0 mg/ml to 1000 mg/ml were shown. As the concentration of K222 increases, the absorbance (vertical axis) at 425 nm decreases, while the absorbance at 575 nm increases. The absorbance at 475 nm is an isosbestic point. It can be observed that Kryptofix concentration is proportionate (not linearly) to absorption at 575 nm, when normalized by the absorption at 475. Spectromax from Molecular Devices was used and the samples were held in a PS flat bottom 384-well plate with 12 mkl indicator and 100 mkl sample in each well.

Suitable metal ions may include, but not limited to, Li+(lithium), Na+(sodium), K+(potassium), Rb+(rubidium), Cs+(cesium), Ag+(silver), Mg2+(magnesium), Ca2+(calcium), Sr2+(strontium), Ba2+(barium), Zn2+(zinc), Cd2+(cadmium), Al3+(aluminum), Bi3+(bismuth), Cr2+(chromium(II)), Cr3+(chromium(III)), Co2+(cobalt(II)), Co3+(cobalt(III)), Cu+(copper(I)), Cu2+(copper(II)), Fe2+(iron(II)), Fe3+(iron(III)), Pb2+(lead(II)), Pb4+(lead(IV)), Mn2+(manganese(II)), Mn3+(manganese(III)), Mn4+(manganese(IV)), Hg+(mercury(I)), Hg2+(mercury(II)), Sn2+(tin(II)) and Sn4+(tin(IV)).

Suitable indicators may include, but not limited to, Arsenazo III, 1H-Benzotriazole, Bismuthiol I, Calcein, Calconcarboxylic acid, Calmagite, Chromeazurol S, o-Cresolphthalein Complexone, Diamine green B, 3,3'-Dimethylnaphthidine, 2,9-Dimethyl-5-picrylamino-o-phenanthroline, 1,5-Diphenylcarbazide, Diphenylcarbazone, Dithizone puriss, Eriochrome® Black T, Eriochrome® Cyanine, Glycine Cresol Red, Glyoxal-bis(2-hydroxyanil), Hematoxylin, Hydroxynaphthol blue, 3-Hydroxy-4-nitroso-2,7-naphthalenedisulfonic acid disodium salt, 3-(3-Hydroxy-4-nitroso-N-propylanilino)propanesulfonic acid, 2-Mercaptobenzothiazole, Methylthymol Blue, Morin hydrate, Murexide, Naphthol Green B, 4-Nitroaniline, 4-(4-Nitrophenylazo)-1-naphthol, N-Phenylanthranilic acid, N-Phenyl-α-(4-nitrophenyl)nitrone, Purpurin, 1-(2-Pyridylazo)-2-naphthol, 4-(2-Pyridylazo)resorcinol, Pyrocatechol Violet, Pyrogallol Red, 8-Quinolinol, Sodium rhodizonate, Thorin, Thymolphthalexon, Tiron, o-Tolidine, Xylenol Orange tetrasodium salt, Xylidyl blue I, and Zincon monosodium.

Pyrogens (5)

Figure 10:
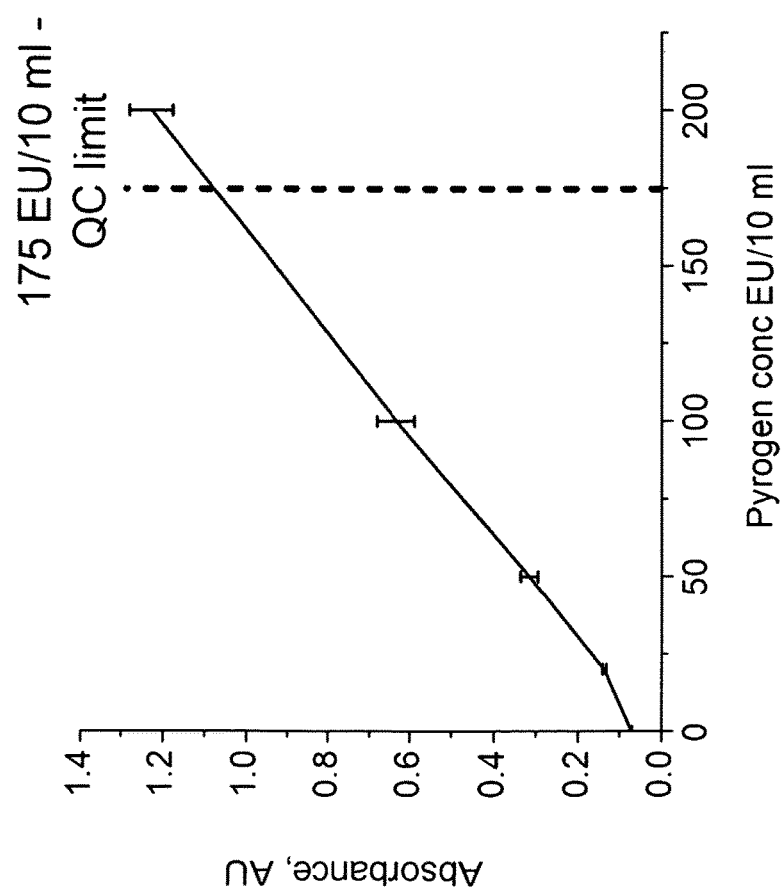
FIG. 10 shows the change of UV-Vis absorbance versus Pyrogen concentration.

Pyrogens (5) are byproducts of bacterial activity that may cause a fever in humans or other mammals. It may be understood that pyrogens may be present in a sample that has no live bacteria and may not be detected by sterility tests. Pyrogenicity is a measure of the presence/concentration of pyrogens in a sample. There are 2 main existing methods for determining it, both relying on a reaction of an enzyme (LAL) with a pyrogen, yielding a visible change in the sample. The acceptance criteria for the pyrogen test are that the entire dose administered to a patient has less than 175 Endotoxin units (EU). The acceptance criteria for a batch of product depend on the size of the batch and volume of each dose. One conventional method relies on a visual signal in a test tube assessed by human eye. Another conventional method relies on an assessment done in a microfluidic chip with a spectrophotometer (PTS reader). The method according to embodiments of the present invention is different from both. As the rest of the methods described herein, it is done on a palette. The analyte sample is mixed with the LAL reagents in a well of a palette and the resulting color or rate of color change is detected by a spectrophotometer. The difference of the method according to embodiments of the present invention from PTS method is that the latter requires a chip and relies on motion of liquids through channels in the chip while the method according to embodiments of the present invention relies on a standard micro titer plate and does not require liquids flowing through the plate. Another distinction is that the PTS chip is so specific that it can only be used for endotoxin testing while the palette in the method according to embodiments of the present invention contains one or more other tests in addition to endotoxin. The latter is an enhancement since no current technology has been able to combine an endotoxin test with other tests. The reason is because all channels have been eliminated in a palette system and it does not require liquid flow. If liquids flow through channels to get to the endotoxin testing site, one would have to assure absence of endotoxins in all channels upstream of the test site, which is not practical. Also, adding other tests to a PTS reader is not practical because of the flow-based detection method. The method according to embodiments of the present invention of pyrogenicity assessment has been validated in the range of 0-200 EU/microliter. FIG. 10 shows the change of UV-Vis absorbance versus Pyrogen concentration using a Synergy plate reader from Biotech. The samples were held in a PS flat bottom 96-well plate with 50 mkl sample and 200 mkl other reagents.

Radionuclidic Purity (6)

Two QC parameters require quantification of the radioactive isotope in the sample: radioactivity concentration and radionuclidic purity. Radioactivity concentration can be calculated from the radiation intensity measured for a sample aliquot. Radionuclidic purity is typically established via measurement of apparent half-life, calculated from two consecutive measurements of the radiation intensity in the same sample. Due to the inherently high variability of determination of exponent lifetime based on just two close data points, QC limit for this parameter is set widely: 105-115 min in case of $^{18}$F (t½=109.7 min).

The common approach is measurement of the half-life of radioactive decay of the sample and comparing it to the known half-life of the desired radio-isotope. The common way of calculating half-life is by measuring the level of radiation emitted by the same sample at two (or more) points in time and correlating the change with the rate of decay. Current standard practice has a person performing two measurements 10 minutes apart using a dose-calibrator and then calculating half-life manually.

By definition, positron emitting isotopes produce positrons during the decay. A method according to embodiments of the present invention utilizes scintillating liquid to convert energy of the emitted positron to the light detectable by a plate reader in luminescence mode.

Figure 18:
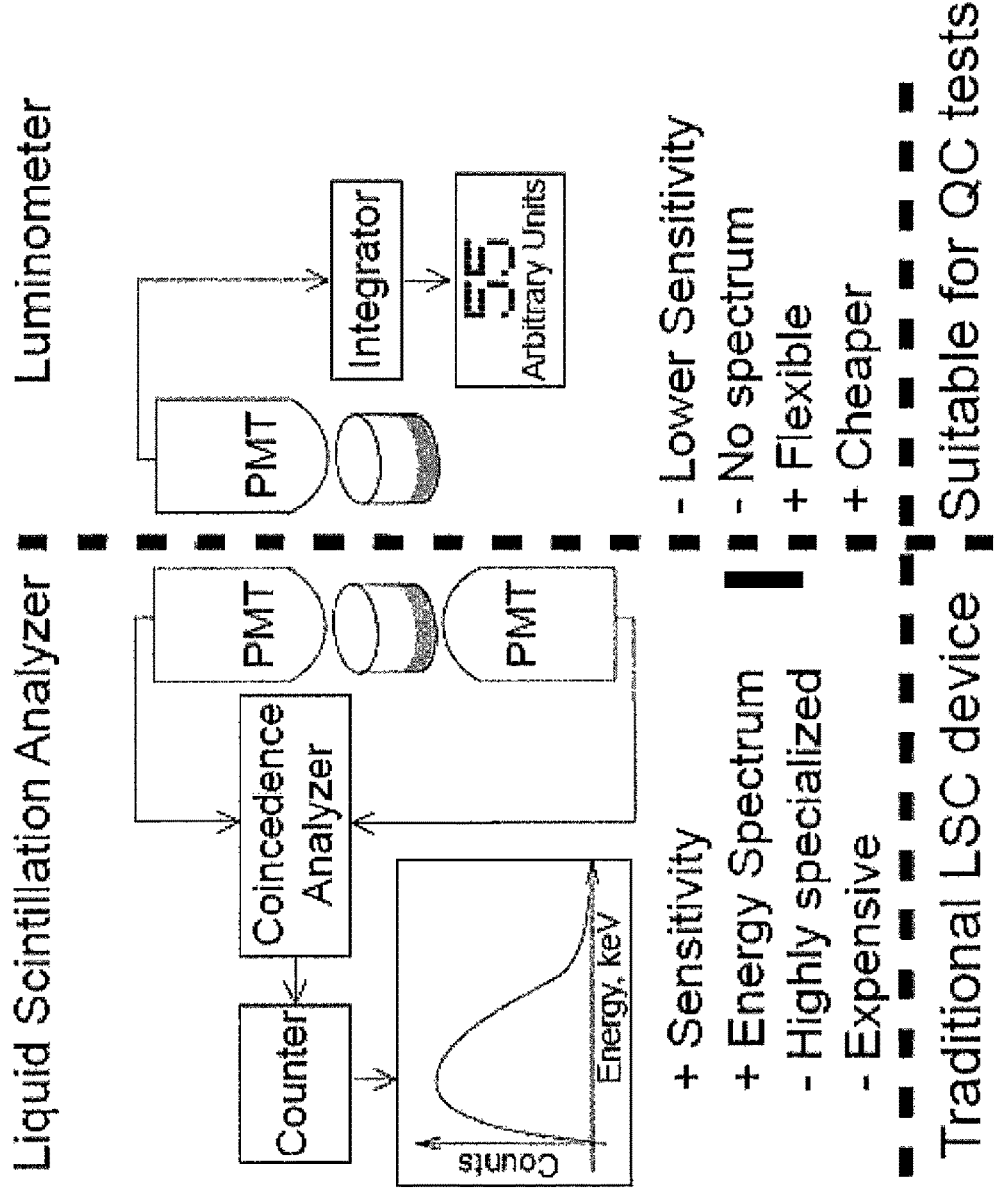
FIG. 18 shows a comparison between a traditional Liquid Scintillation Counting (LSC) device and a QC test utilizing a luminometer according to one embodiment of the present invention.

Typically, a special instrument called Liquid Scintillation Analyzer (LSA) is used to determine the intensity of radiation associated with positron emitting isotopes. FIG. 18 shows a comparison between a traditional Liquid Scintillation Counting (LSC) device and a QC test utilizing a luminometer according to one embodiment of the present invention. As shown in FIG. 18, LSA is a complex instrument designed to detect faint scintillations originating from weak beta emitters such a 3H (0.018 MeV). To discriminate true nuclear events from background noise, these instruments have two light detectors working in sync or one detector. As a result LSA is a highly specialized instrument not capable of other measurements required for QC of radiopharmaceuticals. Instruments combining LSC mode and absorbance mode are also available ("Plate Chameleon" by Hydex from Turku, Finland). However, their extreme sensitivity and spectral capability increase the price of the instrument.

Luminometers, or plate readers with luminescence reading capability, are typically equipped with only one light detector, operating in the integral mode. As opposed to LSA, measuring individual bursts of light, these machines continuously measure light coming out of the sample.

According to one or more embodiments of the present invention, a plate reader in luminescence mode is utilized to detect the light originating from the sample. High energy of positrons originating from 18F and high activity typically used for medical imaging result in strong signal. Therefore, extreme sensitivity of LSA will not be needed for QC of radiopharmaceuticals.

According to one embodiment of the present invention, positron emitting isotopes can be quantified by liquid scintillating counting using specialized counters. More to that, at the levels of activity typical for QC samples of FDG (5 mCi/ml in one embodiment), high sensitivity detector of a liquid scintillation counting (LSC) was clearly saturated, indicating very strong signal. Conventional plate readers lack the high (extreme) sensitivity and spectral resolution of the specialized instruments. However, high intensity of the signal associated with the typical concentration of QC sample, will allow for sufficient signal-to-noise ratio. Here, one or more radiation measurements on positron-emitting radionuclides (required for different parameters) are achieved by luminescence measurement of the total light output from a location where a radioactive sample is interacting with a scintillating reagent. All prior applications with scintillating liquids require scintillation counting by a photomultiplier tube whereas according to embodiments of the present invention, photons of light (luminescence) are measured with a spectrophotometer and the total luminescence signal is correlated with the amount of (positron-emitting) radioisotope in the location of the palette being analyzed.

This measurement is precise, does not rely on subjective timing or the position of a sample within a dose calibrator. Also, this method allows collection of a continuous reading of the light emission, which means a precise signature of the decay rather than sampling it at only two data points. The half-life is also calculated automatically based on the decay monitoring.

Examples of radio-isotopes that may be analyzed according to embodiments of the present invention include, but not limited to, F-18, C-11, N-13, Rb-82, O-15, Tc-99m, I-123, _ 131, In-111, Ga-68. Table 4 summarizes the measurement result of the half-life of sample FDG. In the measurement, 100 mkl of sample FDG dose were mixed with 200 mkl of scintillating liquid. The first measurement was taken at time=0, and the second measurement was taken at time=9.2 minutes. A Synergy plate reader from Bioteck was used in luminescence mode. The samples were held in a PS flat bottom 384-well plate.

TABLE 4

| Sample # | I (t = 0) | I (t = 9.2) | $T_{1/2}$, min |
| --- | --- | --- | --- |
| 1 | 7830 | 7402 | 113 |
| 2 | 8039 | 7582 | 108 |
| 3 | 7744 | 7290 | 105 |
| 4 | 7139 | 6732 | 108 |

Radioactivity Concentration (7)

Figure 11:
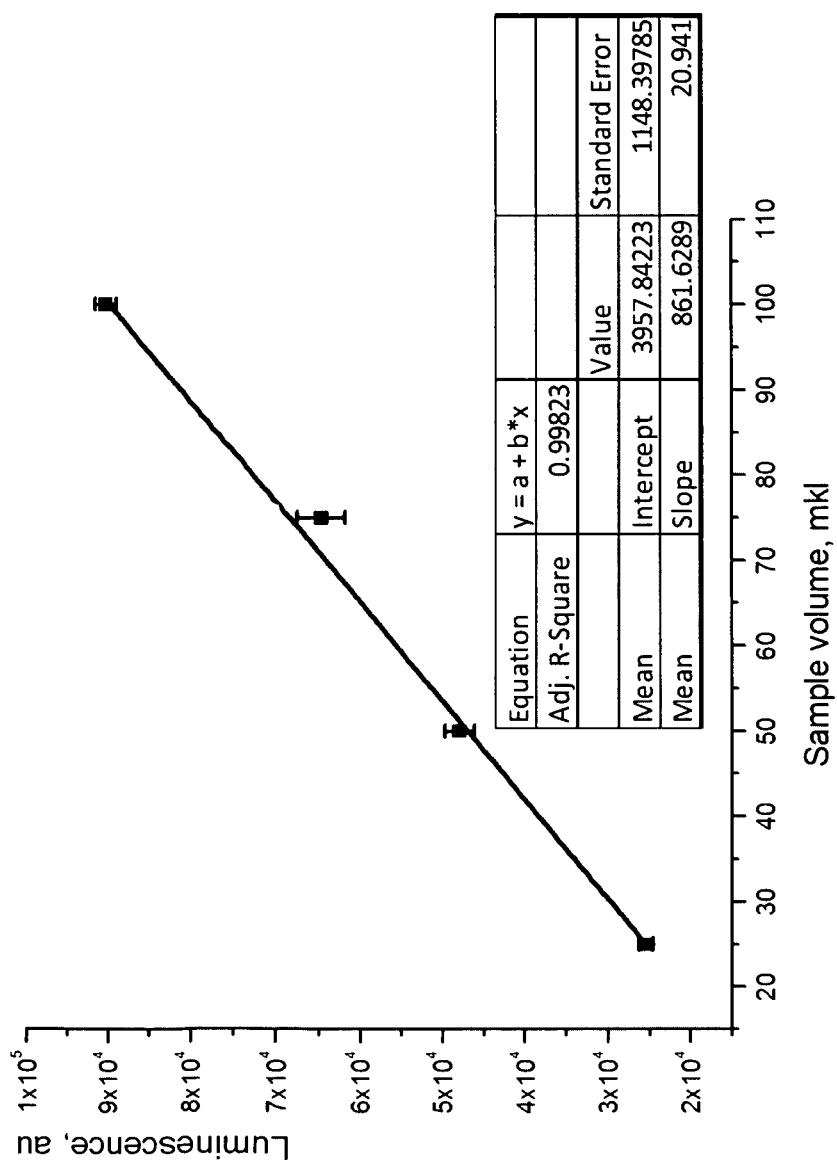
FIG. 11 shows the luminescence of a sample observed as a measure of radioactivity in that sample (optical signal is produced by the response of the scintillating liquid to the radioactive material)

Radioactivity concentration (7) is a measure of the amount of radiation (or radioactive material) per unit volume. The radiation measurement is performed the same way as in the half-life assessment. But instead of correlating the readings with time, it is correlated with the volume of the sample (which may be metered with high precision by a caddy delivering a pre-determined amount of sample to an empty location within a palette). FIG. 11 shows the luminescence of a sample versus the sample volume, where the luminescence intensity roughly depends on the radioactivity concentration in a linear relationship. Here, the samples were contained in a PS flat bottom plate with 384-wells and analyzed utilizing Synergy plate reader from Biotek. Table 5 is a summary of radioactivity concentration measured on a 384-well plate, where radioactive samples were placed in the wells according to the following scheme: Wells E1, E5, E9, E13, E17—100 microliters of sample+900 microliters of scintillating liquid; Wells I1, I5, I9, I13, I17—75 microliters of sample+925 microliters of scintillating liquid; Wells M1, M5, M9, M13, M17—500 microliters of sample+950 microliters of scintillating liquid; Wells P1, P5, P9, P13, P17—25 microliters of sample+975 microliters of scintillating liquid. The rest of the wells were left empty. One batch of radioactive material was used for the whole experiment while different amounts of it were mixed with the scintillating liquid as indicated by the ratios on the left side of the first column. Wells of the same shade have the same amount of radioactive material. Wells of different shades differ in the ratio of the amount of radioactive material with the amount of the scintillating liquid. The numbers in the wells represent the luminescence readings. As can observed from Table 5, the readings from the filled wells are 3 orders of magnitude higher than readings from the adjacent wells, confirming that no cross-talk between wells and no interference between different radioactive samples even in the absence of any radiation shielding.

Figure 12A:
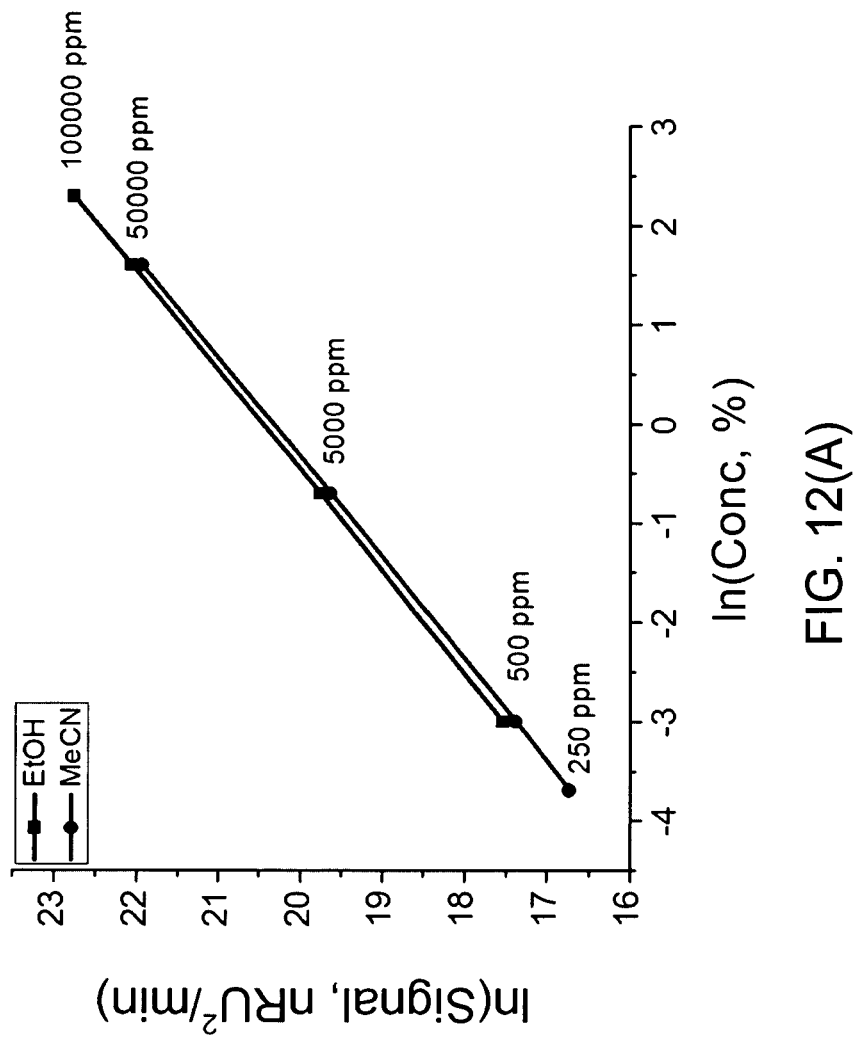
FIG. 12(A) shows the result measured using a Refractive Index detector versus the concentration of ethanol and acetonitrile.
Figure 12B:
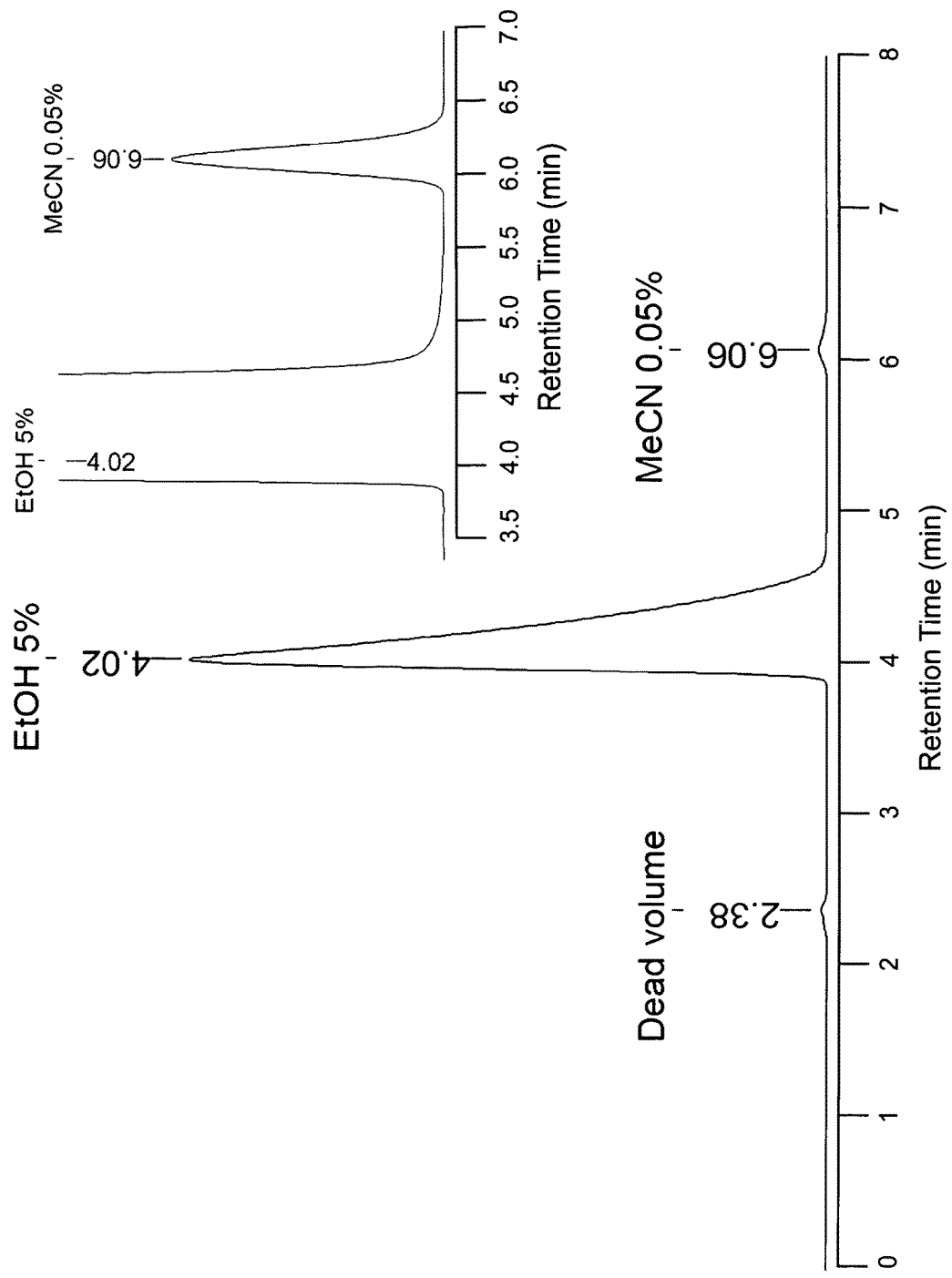
FIG. 12(B) shows an HPLC peak versus retention time for ethanol and acetonitrile.

HPLC, simultaneously triggering the start of a chromatogram. FIG. 12(A) shows the result measured using a Refractive Index detector versus the concentration of ethanol and acetonitrile; and FIG. 12(B) shows an HPLC chromatograph versus retention time for ethanol and acetonitrile. As can be observed in FIG. 12(A), the result of the RI detector has excellent sensitivity and linearity over the entire range of concentrations tested. As can be observed in FIG. 12(B), the polymeric columns using Hamilton PRP-1 and DI water as the mobile phase have excellent separation efficiency over the entire range of concentrations.

TABLE 5

|   | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|----|----|----|----|----|----|----|----|
| E | 89672 | 136 | 27 | 188 | 92568 | 123 | 23 | 143 | 88993 | 122 | 18 | 141 | 90574 | 130 | 21 | 121 | 90759 |
| F | 130 | 45 | 15 | 42 | 135 | 45 | 16 | 46 | 130 | 45 | 12 | 39 | 152 | 45 | 17 | 43 | 152 |
| G | 17 | 16 | 13 | 16 | 16 | 20 | 14 | 35 | 16 | 13 | 21 | 11 | 16 | 13 | 10 | 10 | 18 |
| H | 71 | 30 | 14 | 39 | 99 | 46 | 17 | 36 | 94 | 31 | 13 | 42 | 103 | 49 | 11 | 28 | 84 |
| I | 60029 | 69 | 16 | 100 | 66541 | 93 | 17 | 117 | 65807 | 85 | 17 | 110 | 67069 | 94 | 23 | 104 | 64603 |
| J | 85 | 24 | 15 | 45 | 107 | 42 | 22 | 29 | 114 | 40 | 15 | 40 | 122 | 41 | 13 | 34 | 114 |
| K | 14 | 10 | 11 | 15 | 15 | 17 | 11 | 21 | 12 | 19 | 8 | 12 | 11 | 10 | 10 | 9 | 13 |
| L | 55 | 24 | 14 | 31 | 66 | 23 | 10 | 39 | 55 | 26 | 13 | 27 | 81 | 34 | 14 | 24 | 75 |
| M | 45029 | 59 | 13 | 70 | 49138 | 73 | 23 | 73 | 47779 | 64 | 28 | 74 | 49541 | 74 | 17 | 79 | 48462 |
| N | 79 | 22 | 13 | 26 | 87 | 28 | 16 | 29 | 99 | 25 | 8 | 24 | 99 | 24 | 11 | 30 | 89 |
| O | 38 | 12 | 12 | 15 | 37 | 20 | 11 | 21 | 42 | 22 | 12 | 19 | 61 | 18 | 19 | 19 | 47 |
| P | 24268 | 40 | 8 | 54 | 25129 | 30 | 9 | 45 | 25958 | 49 | 11 | 55 | 26071 | 43 | 14 | 46 | 25943 |

Organic Solvents (8)

Organic solvents (8). It is important to measure the concentration of organic solvents in the sample because they are toxic (above a certain concentration). Organic solvents such as acetonitrile (MeCN) may originate from the synthesis procedures. Meanwhile, ethanol (EtOH) is used to formulate the sample for injection, but it too cannot exceed a certain limit. Traditionally concentrations of these solvents are measured with a gas chromatograph (GC) which is an expensive multi-purpose instrument requiring sophisticated maintenance and extreme precision of sample injection (which is frequently done manually). A method according to an embodiment of the present invention eliminates the need for GC and may rely on one of several options, two of which are described below.

Option 1—spectrophotometric detection with an indicator. A suitable indicators may react with each specific organic solvent (starting with MeCN and EtOH) and result in an optically-detectable change that can be correlated with the concentration of that specific solvent in the sample being tested. In one embodiment a set or specific amount of sample is mixed with a set or specific amount of indicator and the resulting color is measured on a palette by a spectrophotometer with light passing through the well and the absorbance being measured. The intensity of the resulting absorbance, measured at a set or specific wavelength is correlated with a (precise) solvent concentration in the sample. As in the other tests, this measurement is precise, subjective, traceable and user-independent.

Option 2—HPLC. A method according to another embodiment of the present invention relies on separating solvents on an HPLC column and detecting them upon exit from the column using a refractive index detector. Each solvent will have a known retention time and the Analytical Ultracentrifugation (AUC) in a chromatogram can be correlated with the concentration of that specific solvent. This method relying on palette and caddies allows high precision of injection volume and time while eliminating any need for manual handling or analysis of results. A caddy picks up a known volume of sample from a palette and injects it into Radiochemical (9) and Chemical (10) and Radiochemical Identity (11)

Radiochemical (9) and chemical (10) purity and radiochemical identity (11) is a measure of contamination of the radioactively-labeled product by radioactive and non-radioactive contaminants and confirmation that the main product is indeed the desired product by comparing it to a non-radioactive standard. Traditionally it is performed by TLC or HPLC. The conventional method requires daily preparation of standards that cannot be stored in solution and require extreme precision, which is difficult to achieve manually with small sample size. Then multiple standards are injected and multiple chromatograms are acquired and analyzed by a person. A method according to embodiments of the present invention allows for this assessment using HPLC with UV-Vis and radiation detectors. While the chromatography component is similar to current methods, the infrastructure around it is different. First, the injection in the method according to embodiments of the present invention is automated and delivers precise volume of sample picked up by a caddy from the palette and injected at a precise time concurrently or simultaneously triggering the start of a chromatogram. Also this method allows for the inclusion of the results of this test in the complete over-arching report on all QC parameters. In all current methods HPLC is run independently of all other tests. In addition, the difference and benefit is in the daily system suitability testing and calibration. Currently, the latter processes require preparation of multiple standard samples followed by their individual injections into HPLC, generation of multiple chromatograms and their analysis (with a lot of manual handling). The method according to embodiments of the present invention allows all standards and reference samples to be pre-packaged on a palette in precise amounts, which are stored dry as powders. Solvents may be stored in different locations on a palette. As the process starts, the solutions may be made automatically with high precision using caddies and injected automatically. For example, an automatic injector may take samples directly from a palette. Or a caddy may be utilized to transfer samples from the palette to the HPLC injection port. Further, the method according to embodiments of the present invention allows chromatographic programs and analysis algorithms to be programmed into the instrument. So all the user has to do is to insert the palette and start the program. The instrument will then execute a sequence of calibrating/suitability chromatograms, analyze their respective reports and signal that system is ready for the injection of the analyte sample without any user interaction (which now requires hours of work every day and has very poor traceability or reference standard amounts, concentrations, injection times and other data in the conventional method).

There is an alternative to HPLC for the assessment of chemical and radiochemical purity. It keeps all testing within a palette but requires palette customization. A bed of chromatographic stationary phase is deposited within a palette having a substantial length. This may be a TLC plate coated with mobile phase or a small column packed with stationary phase. The sample is administered on one end of the plate/column and moves to the other end. In case of TLC it may move via absorption of the solvent. In case of a small column it may be pressurized or pulled by a vacuum. Once the first components of the sample have traveled the full length of the stationary phase, an assessment is performed on the components of the mixture separated along the stationary phase based on their affinity for the latter. The assessment may be performed by shining UV light onto the stationary phase and measuring its absorption on different locations (indicative of the type and amount of material deposited at that location and yielding a chromatogram). This chromatogram may be obtained on a plate reader. It may be digital (reading above each of the wells covered by the chromatographic bed) or continuous (measurements at all locations). Similar approach may be taken for the radioactive trace with scintillating liquid deposited underneath or in close proximity to the stationary phase such that the radioactive emission from the various radioactive components deposited on the stationary phase triggers signals from the scintillating liquid at the corresponding locations. It is to be noted that such assessment is not reflective of a single point being monitored upon separation of mobile phase from solid phase. Instead it allows to observe live separation on the solid phase while it is in progress.

Yet another embodiment requires no chromatographic separation for the assessment of chemical purity. It requires a known absorbance spectrum of the 100% pure product as a reference. Such spectrum may be obtained on a plate reader from a single well/position within a palette without moving the sample or separating it on stationary phase. For example this may be a UV absorbance spectrum, with absorbance measured at each wavelength of the spectrum. Once this complex pattern is obtained for a product with 100% purity, the spectra obtained from analyte absorption measurements within the same spectrum may be compared to this reference. If the difference between the standard and analyte absorption spectra reaches a certain percentage at any one wavelength, the analyte may be classified as impure. However, if the analyte spectrum falls within pre-defined error bars around the standard spectrum, the analyte will be considered to be of acceptable purity. The width of error bars should be determined experimentally for each product. The width of error bars may be uniform or may vary between different wavelengths. The absorbance spectrum may be measured within any range of detectable wavelengths. Visible, UV, and IR ranges are just examples and are not meant to limit the application of this invention.

In some cases, the analyte may have poor absorbance in all ranges of the spectrum. In such a situation, the analyte may be combined with a reagent that enhances its signal and allows to quantify the amount/concentration of the analyte.

A method according to another embodiment of the present invention utilizes palette-based method to assess radiochemical purity. Typically small radioactive contaminants have no absorption in any spectral ranges (they are below the detection limit). Thus to determine the presence of radioactive impurities that have no optical signal, one may either rely on the TLC-type method above or filter an analyte sample through a plug of stationary phase that is designed to trap either the impurities or the desired product. By comparing the radioactivity measurement in the plug to that in the liquid that came through it, one can assess the ratio of desired product to impurities.

Specific activity may also be assessed using absorption spectrum from a single well and comparing it to the radioactive measurement from a single well using scintillating liquid. This allows specific activity determination without any chromatographic methods.

Sterility (12)

Sterility (12) is the final parameter in quality control. It is the confirmation of the absence of any living organisms (bacteria) in the sample. However, there are no other tests available that can yield a result within a time-frame compatible with the decay of the radionuclides used in PET. A typical sterility test involves providing a culture in which bacteria may grow and replicate to the point when colonies become visible—a process that takes 14 days. Meanwhile a typical radionuclide used in PET (F-18) has a half-life of 110 minutes and F-18-labeled products have a maximum shelf-life of 6 hours. Therefore the currently acceptable test relies on having the results of 14-day sterility test after the product has been administered to patients and assuring sterility on the front end by passing the entire volume of product through a sterilizing filter, followed by confirmation that the filter is still intact after the filtration procedure. So there are really 2 tests required for sterility (1) 14-day culture test with post-injection results and (2) pre-injection filter integrity test. A method according to embodiments of the present invention offers 2 options for sterility assessment:

Option 1: traditional culture test performed with a palette system would require smaller volume of reagents, shorter time for culture to develop and an exact measure of bacterial activity (versus presence/absence confirmation). In an embodiment of the current invention a set or specific amount of sample is mixed with a set or specific amount of growth culture and placed into an incubator (e.g. at 37 degrees). Periodically, the palette containing mixed sample and culture is taken out of the incubator and assessed optically in a plate reader (spectrophotometer) to monitor changes in the optical properties of the wells of interest. This method allows detection of bacterial colonies at a much smaller size (and therefore earlier time point) than current method relying on visual assessment by human eye after 14 days. It also allows measurement of the density of colonies and their growth rate. The results are available earlier than 14 days, human interaction and error is reduced or eliminated and measurements are quantitative. In embodiments where this data is available after administration of product to patients the filter test will still be required. For the latter, a subsystem of the synthesis/analysis system will be placed inside the radiation shielding where the filter is located. The filter will be connected to a pressure line and the instrument will monitor a pressure drop across the filter which can be correlated with its integrity. The way this method differs from the current manual assessment is that it allows to measure (measure exactly) what pressure the filter may hold and how close it may be to break-through point. Current method relies on a visual assessment and does not yield a quantitative result.

Option 2: Instantaneous assessment of sterility in a palette with a spectrophotometer. This method does not rely on the growth of colonies and therefore does not require the time necessary for such growth. It allows detection of live cells (with a limit of detection being 1 cell) in a sample. It relies on reagents that react with cell membranes yielding an optically detectable signal allowing to quantify the number of live cells present in the sample. Since the results of this test will be available prior to administering products to patients, the need for the filter test will be eliminated. The intensity of signal arising from the well is proportional to the number of live cells in that well (and the speed of the test does not rely on the speed of formation of bacterial colonies).

Option 3: rapid test within the palette requiring no reactions but relying on flow. It requires a custom palette with a channel between two wells and a pair of electrodes placed across the channel. The diameter of the channel is comparable in scale to the size of live bacterial cells. The electrodes measuring resistance (or any other signal) across the channel produce different signals in the presence of pure solution versus having a cell (pass) between these electrodes. Once the entire sample volume is passed through this channel from one well to the other, the number of spikes (or signal changes) detected by the electrode corresponds to the number of live cells in the sample. In order to make this method fast and practical, a number of channels may connect the two wells instead of one with electrodes on each channel. This way a volume of the sample that is on a much larger scale than the cross section of a channel may be processed within a short time period. The number of channels may range from 1 to several million, limited only by the maximum channel density allowed by manufacturing techniques.

In another embodiment, a combination of the two above methods is used to determine sterility. One or more channels connect two locations fluidically. Each channel has a physical trap for living cells at a specific location. The trap may be a filter or a constriction in the channel. In case of a filter, once the cell is trapped, the liquid keeps flowing around it. In case of a constriction once the cell is trapped, the channel is plugged and the flow stops. These traps may be used to detect live cells by different means. In one embodiment the cells are labeled with materials that bind to their membranes and produce optical signals. These signals may be detected by a spectrophotometer monitoring a specific location (or locations in the embodiment with multiple channels). The enhancement of this method over the one with cells in a well is that the cells become immobilized, which allows attenuation of the optical signal.

In another embodiment, the flow is measured in all channels. The channels that have cells trapped in them will have reduced flow. Thus the change in flow in a given channel or the number of channels with reduced flow may be correlated with the number of live cells in the initial analyte sample. Constrictions and filters are only examples of cell traps. Other embodiments are possible. It is also possible to carry out this method without a trap. If the optical detector placed above the channel is sensitive enough to recognize moving cells, than the trap is not necessary.

It is to be noted that cell trapping and analysis described above may be achieved with no valves. It is also to be noted that certain embodiments of the above invention may operate with forced flow while others without forced flow. It is also possible to realize this invention with or without palettes and caddies. In one embodiment of the present invention, the sterility-testing system according to embodiments of the present invention is packaged as a stand-alone device not including any other tests described above. Such device may or may not have disposable components.

In another embodiment the sterility measurement based on detection of individual cells assures such detection by labeling live cells with radioactive markers, which are much easier to detect than optical signals.

In another embodiment the liquid may be pulled through channels by a vacuum. In yet another embodiment the liquid may be pushed into a channel towards the end of the channel or another reservoir that is closed by a gas-permeable liquid-impermeable membrane. It is also possible to assemble such a device from materials that have hydrophilic surfaces that pull the aqueous sample from the source to the sink without any extra motive force. It is possible to have the liquid move by capillary force.

In another embodiment it is possible to use the above methods for sterility detection not only to detect and quantify all live cells, but to distinguish between the types of cells. (For example (but not limited to) detecting bacteria in whole blood.)

In the live-cell-detection systems described above the number of sources and sinks is not limited. It may be 1:1 or 1 to many or many to 1. The source may have the same volume as the combined volume of all channels. Thus the channels themselves become the sink. The source may be a container in the center of a device with channels radiating like wheel spokes away from it, while the sink is a tube along the circumference where all the spoke channels lead to. These are just examples and may other embodiments may be either possible or more practical.

While a palette may include containers for each of the above described test methods, a palette may not necessarily have all of them. For example, a palette may include containers for only two of the above described test methods. According to one embodiment of the present invention, a palette may include at least one container for a reagent that requires sterile environment and at least one reagent that does not require a sterile environment. For example, a palette may include a container for detection of LAL reagents and a container for one of the other reagents, such as pH indicators, and both being packaged in a sterile environment. In an existing system, the LAL reagents are not combined with the pH indicators in the same environment, because while LAL reagents require a sterile environment, a pH reagent does not.

Integrated Devices and Methods for Production of Imaging Tracers

An aspect according to embodiments of the present invention is directed toward a system that may receive raw radioactive isotope (for example directly from accelerator) and perform radio-synthesis, quality control and dose dispensing without any user interaction. According to embodiments of the present invention, one system performs all 3 tasks and does not rely on the integration of 3 separate systems into one.

Figure 3:
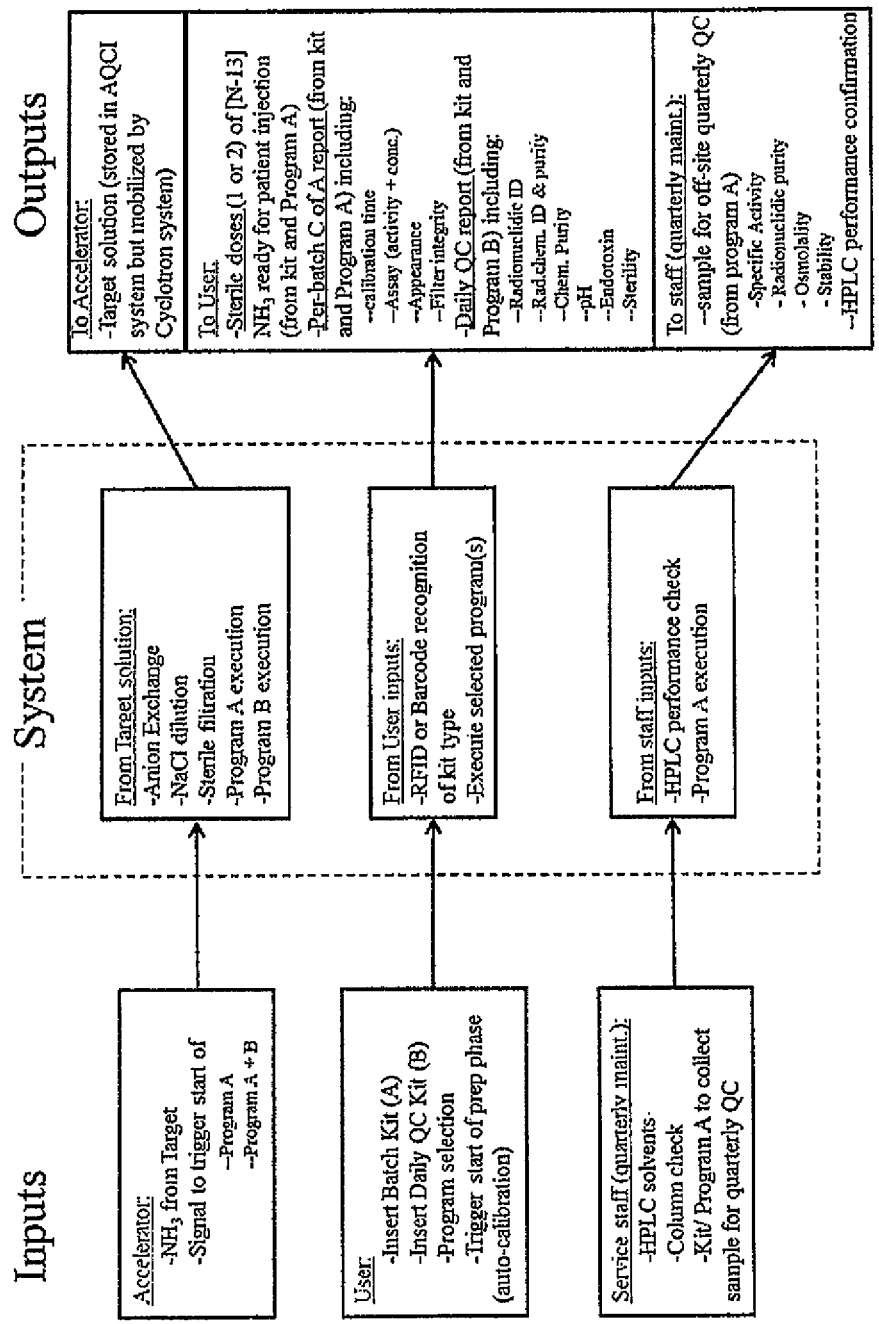
FIG. 3 is a schematic illustration of the inputs and outputs of [N-13] synthesis, QC, and dose-dispensing system according to one embodiment of the present invention.
Figure 4:
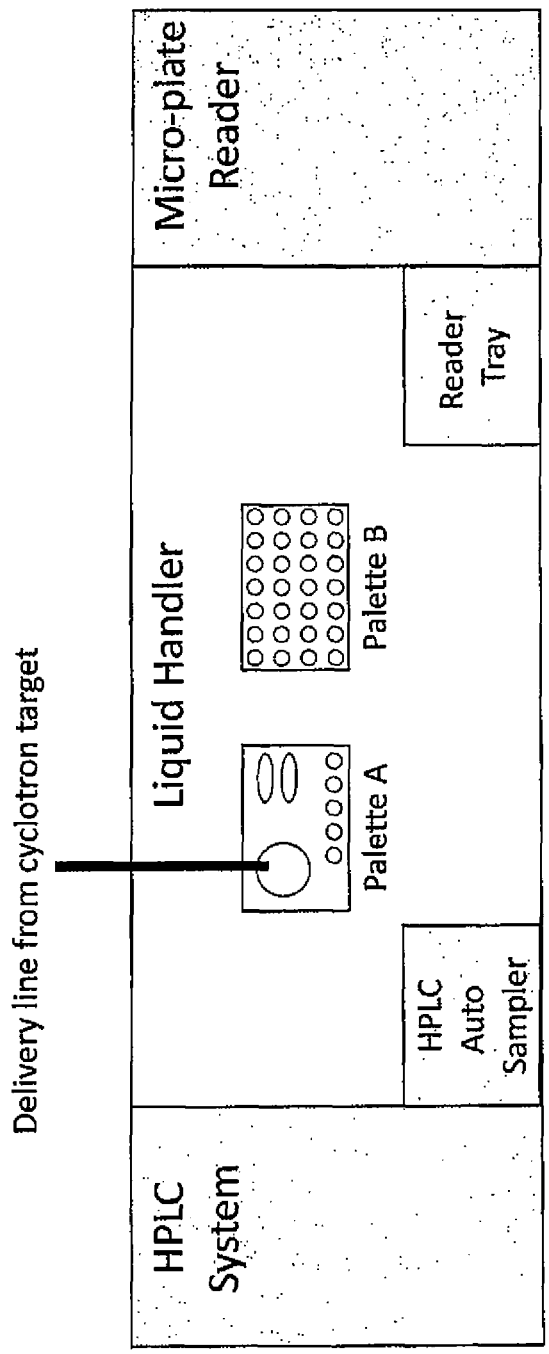
FIG. 4 is a schematic illustration of a system according to one embodiment of the present invention.

The system described herein is designed to receive raw isotopes form the accelerator, carry out synthesis, QC and dose dispensing and yield radioactive imaging tracers in the form suitable for IV administration to patients. FIG. 3 illustrates the concept of an all-in-one system. Meanwhile, FIG. 4 represents one of the embodiments of such a system that is designed for the production of 13N-ammonia, which is a PET tracer used in cardiology.

In the latter embodiment the system is designed to carry out all functions of synthesis, dose preparation, quality control and dose dispensing while relying on (a) a stationary instrument including combination of a liquid handler, a plate reader and/or an HPLC interconnected with one another; and (b) single-use palettes (referred to as Kit A and B). Kit A is designed to enable all of the following: dose production, dispensing and per-dose quality control. Meanwhile, Kit B enables periodic (daily) quality control, which does not need to be performed for every dose. Therefore, the frequency of use of Kits A and B may be different. All reagents and standards are included within the kits. The user only needs to supply an HPLC solvent specified.

For example, Kit A (FIG. 4) is designed to receive raw 13N-ammonia directly from the accelerator target. It has an on-board filter 431 that assures sterility and can be tested after filtration for its integrity without being removed from the system. Kit A also contains other synthesis components such as Ion-exchange column 432 and chemicals such as saline. It also has optical detection compartments 435 which enable analysis in a plate reader (such as in a palette-caddy systems). It also has a container 433 that can be removed from the kit with final product in it and can be used for patient IV administration. Finally, Kit A has a feature 434 that makes the product accessible via a caddy, which can take a product sample to other locations within Kit A as well as to Kit B (when needed).

In one embodiment of Kit B, it receives a sample via a caddy and performs quality control tests such as described in previous embodiments. Table 3 lists all testes required for 13N-ammonia along with their frequency and outlines the enablement of these QC tests by Kits A and B.

TABLE 3

| | Measurment | Frequency of measurement | Handling |
| --- | --- | --- | --- |
| 1 | Appearance | Every dose | Kit A |
| 2 | Assay (radioactivity yield and concentration) | | |
| 3 | Membrane filter integrity | | |
| 4 | Radionuclidic identity | Every day | Kit B |
| 5 | Radiochemical identity & purity | | |
| 6 | Chemical purity | | |
| 7 | Acidity (pH) | | |
| 8 | Bacterial endotoxin | | |
| 9 | Sterility | | |
| 10 | Radionuclidic purity | Periodic (quarterly) | Off-site |
| 11 | Osmolality | | |
| 12 | Specific activity | | |
| 13 | Stability | | |

It is to be noted that although 13N-ammonia is used as an example, the system is not limited for the production of this tracer. It is suitable for other PET and SPECT tracers as well as for an extended range of applications including non-radioactive products.

The other system aspects/embodiments are summarized below:

The system may be integrated (e.g., completely integrated) with accelerator and operate as one instrument with a single user interface. The system may need accelerator to send a signal that indicates isotope delivery. The system may require the user (hospital staff) to insert a combination of Kits A and B for the first (analytical) production run of the day and only kit A for each subsequent (dose) production run. The system may require the user to select a program (from menu) for either the analytical run or the dose run. The system may deliver to the user individually packaged sterile doses (using [N-13]ammonia as an example).

The system may perform (a) synthesis, (b) per-dose QC, (c) aseptic daily QC, (d) dose labeling, and (e) dose dispensing functions. The system may provide a daily QC report from analytical production run (first run of each day), a Certificate of Analysis for each dose run (every batch), and individually packaged sterile doses of 13N-ammonia ready for patient administration (1 or 2 per production dose run).

User Interface

In one embodiment of the present invention, there are two main modes in which the host institution personnel will interact with the system: (1) quality control mode and (2) clinical mode. A third mode—(3) maintenance mode—may only be available to service personnel. It may require single-use kits (palettes) and executable programs "B" for mode (1) and executable programs "A" for mode (2).

The following description illustrates one example synthesis process for manufacturing 13N-ammonia.

Figure 5:
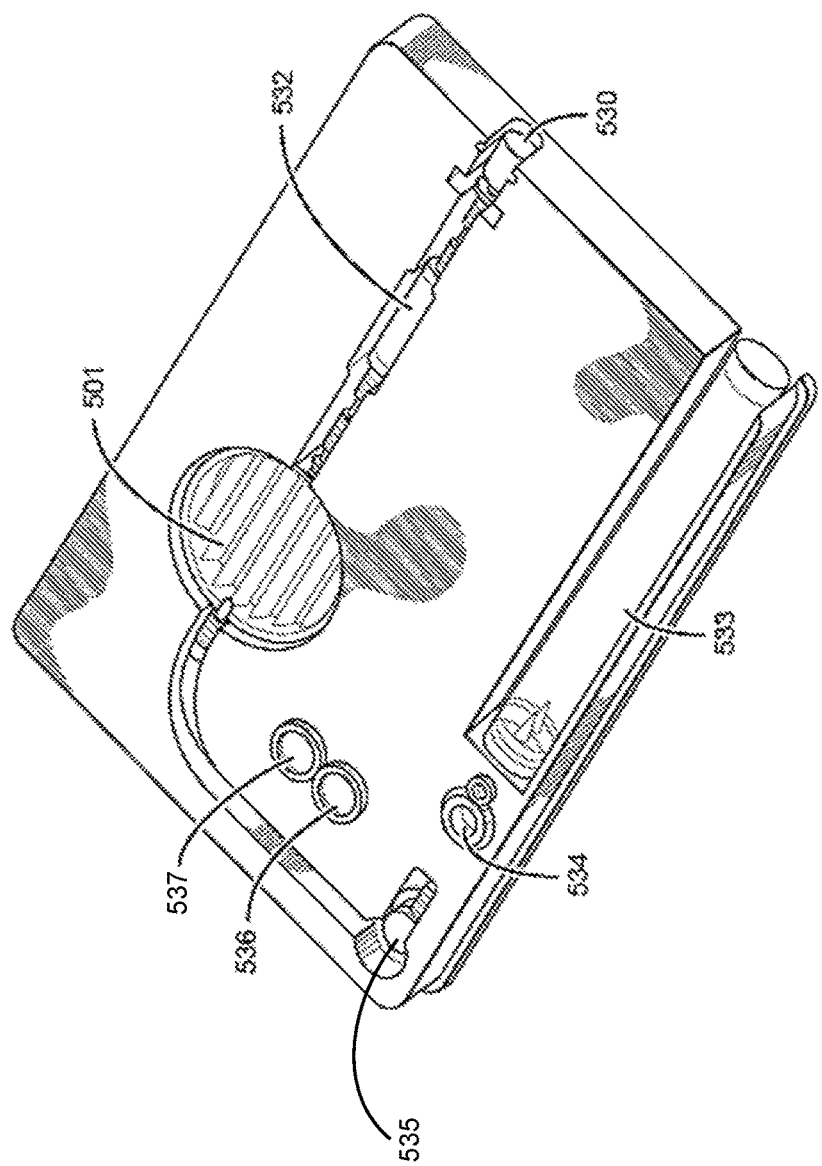
FIG. 5 is a more detailed illustration of a kit A of FIG. 4.

13N-ammonia is produced in the target, so the synthesis system is fairly simple and includes mainly of filtering and dilution steps accomplished within the system:

Referring to FIG. 5, the irradiated water delivered from an accelerator is introduced to kit A through an entry port 530 and passes through an anion exchange column 532 located within kit A; the irradiated water is mixed with water and sodium chloride supplied via Kit A; the mixture is passed through the filter (biological membrane) 501 located within kit A.

Dose Production and Clinical Mode

Kit A (FIG. 4) is placed within the liquid Handler. A liquid handler may be any suitable device that may perform the function of injecting, aspirating, or moving a liquid sample from one container or location to another container or location. For example, a liquid handler may include an automated pipette with exchangeable pipette tips (that function as caddies), connected with a source container of a liquid sample, to inject a given amount of the sample into the wells of micro titer plates that function as palettes. The liquid handler may further include a sample platform for moving the palettes from one location to another location, and/or moving the pipette to fill the sample in desired locations on a palette. Delivery line from cyclotron is connected to Kit A. According to one embodiment of the present invention, the system first performs a self-check and reports "ready to receive raw product from target" status. The target is then unloaded by accelerator pushing raw unfiltered product to Kit A within the system through the delivery line. The accelerator then gives a 30 second pulse of 50 psi gas pressure into the delivery line. During the delivery the following processes happen within Kit A. Raw product is passed through an anion exchange resin 532. Resulting solution is passed through the sterile filter 501, installed downstream from the ion exchange cartridge. Filtered product is added into the saline stored within the syringe cartridge 533. Upon delivery, the dose preparation and analysis begins. An auto sampler pipette tip aspirates 200 ul of the filtered product through a duck-bill valve 534 installed in the fluid path. Auto-sampler then dispenses this product into two wells within the Kit A: assay well 536 and clarity well 537 with 100 ul in each well. The shaker installed on the liquid handler deck shakes Kit A to mix the saline with the dose delivered. According to embodiments of the present invention, the system further includes a gripper that can move the entire palette from one location to another.

Here, the liquid handler gripper transfers the palette to a plate reader for analysis. The plate reader reads optical parameters in three locations: assay well 536, clarity well 537 and optical cell 535 downstream of filter. Assay well is read for luminescence, clarity well is read for absorption and scattering, presence of bubbles in optical cells is determined based on the light refraction.

The readings are translated into numerical values for color, clarity and radioactivity yield and concentration. Filter integrity is reported as pass/fail value. A Certificate of Analysis (CoA) report is populated along with acceptable ranges and pass/fail results.

Kit A is then moved back to the Liquid Handler deck. Once the measurement results are available and acceptable, the user may remove syringe(s) from Kit A and use them to administer doses of [N-13]ammonia to the patient.

Daily Quality Control Mode

Kit B is placed within the liquid Handler alongside with Kit A for the first production run of the day (sacrificial QC run). QC program is started including HPLC equilibration and standard injection. Once the preparation of HPLC is completed, the system is ready to accept raw product from the target.

All operations described in the Clinical Mode are carried out within Kit A, but the sample taken for analysis is also added to a specified location in Kit B.

Kit B is moved to HPLC auto sampler where the HPLC injection takes place. The HPLC runs autonomously yielding integrated chromatograms that provide the results of radiochemical identity, radiochemical purity and chemical purity (along with acceptable ranges and pass/fail results)

After the start of the HPLC analysis, the liquid handler takes samples of the product and mixes them with various reagents in different wells: for example, pH indicator(s) for pH measurement; LAL reagents for bacterial Endotoxin; and Growth media for sterility. The plate is moved to the plate reader to perform optical measurements.

Once measurements have been performed, the plate is sealed and placed within the 37-degeree incubator. Once all results except sterility are available and acceptable, the Certificate of Analysis is officially completed and the system may start producing clinical doses.

The plates stored in the incubator will be taken out (automatically) once a day for 14 days (or less) and assessed in the plate reader.

After 14 days of data have been collected, it is evaluated to conclude whether the sample was sterile. The results are then added to the original CoA report. If the sample fails the sterility test, the system generates an alarm.

User Interface

Software is provided by having the level of access that allows process modifications by the developer. The end user will have a level of access that allows them to choose a program and collect the CoA report.

User Perspective

In Clinical Mode, the run time is about 20 min from cyclotron to packaged product. The consumables include Custom Kit A (custom developed hardware and reagents) including ion exchange column filter, dose syringe, and analytical cells (for appearance and assay). Tasks performed include sterile filtration, per-dose tests (appearance, assay, filter integrity), dose dispensing into final container (syringe or part of syringe) and dose acceptability report (CoA).

The skill level needed is that of a technician. The software is integrated with accelerator software.

In Daily QC mode, the run time is about 40 min from sample to report. All results are in one report including pass/fail information. The consumables include Kit A (custom) and B (standard HW, proprietary chemicals), and HPLC solvents. The passing criteria for clinical doses of 13N—NH3 include:

Radionuclidic ID: Half-life between 9.5-10.5 min;
Radiochemical ID: Retention time within 10% of standard;
Radiochemical purity: Product rad. peak AUC>90% of total;
Chemical purity: Product conductivity peak AUC>90% of total;
Specific activity: >10 Ci/mmol;
pH: between 4.5 and 7.0;
Bacterial Endotoxin: <175 EU/dose;
Sterility: TBD.

The skill level needed is that of a technician.

Embodiments of the present invention include an integrated system includes a Liquid handler, a Plate reader and an HPLC, operated by a single control interface. Two types of disposable kits (palettes) designed to support the system operation: "Kit A" for Clinical mode: enables per-dose QC tests and dispensing of the dose into an injection container (syringe); and "Kit B" used together with "Kit A" for QC mode: enables daily QC tests. Methods enabled using Kit A include: Ion Exchange; Sterile filtration; Formulation; Appearance test; Assay test; Filter integrity test; and Dose packaging into syringe. Methods enabled using Kit B include: Radionuclidic identity test; Radiochemical Identity and purity test; Chemical purity test; pH test; Bacterial Endotoxin test; and Sterility test.

The consumables include Kit A (FIG. 5) and Kit B.

Kit A yields doses suitable for clinical administration, and yields test results for all per-dose QC tests; Kit B (used in conjunction with Kit A) yields test results for all daily QC tests.

In this embodiment, Kits A and B encapsulate all supplies for production and QC except for HPLC solvents and pipette tips (packaged separately).

The system also includes an injector accepting an injection container (syringe) of Kit A and enabling IV injection.

A system (and method) capable of accepting radioactive isotope directly from accelerator target and yielding clinically-acceptable radioactive tracer ready for human administration has been described. The system may include palettes and caddies. All reagents may be pre-packaged in a palette. The consumable contains a filter and a final product container. The filter within the disposable kit may be tested for its integrity automatically after it has been used.

While embodiments of a consumable system within which all actions of synthesis, formulation, QC and dose dispensing can be carried out (within one consumable device) has been described, the present invention is not limited thereto and various modifications may be made. According to some embodiments, a palette-caddy system supporting any combinations of radiosynthesis, quality control and radiopharmaceutical dose dispensing may be enabled by a combination of a liquid handler and a plate reader. According to another embodiment where the system for carrying out any one or combination of radiosysnthesis, quality control and dispensing of a radiopharmaceutical product relies only on a combination of the above described liquid handler, plate reader and a liquid chromatograph interconnected with one another (and does not require traditional chemistry modules or individual analytical equipment).

According to another embodiment, QC and dose dispensing processes are inter-related in a system. An example of the latter is the determination of radioactivity concentration in the QC process is dictating the parameters of drawing individual patient doses automatically. The user requests desired doses (as amount of radioactivity at a specific time) and the system draws the volume necessary based-on the concentration that it (the system) determines without the user interaction. An inter-linkage between synthesis and QC is the filter test where the same hardware used for the filtration of the product is used for the assessment of filter integrity.

Dose Dispensing

In dose dispensing applications, parallel drawing of multiple doses of radiopharmaceutical product, for example, where the doses differ from one another, may be realized according to embodiments of the present invention. For example, a container with the radiopharmaceutical product may be accessible simultaneously by two or more, five or more, or ten or more individual dose containers (which may or may not be syringes).

Figure 15:
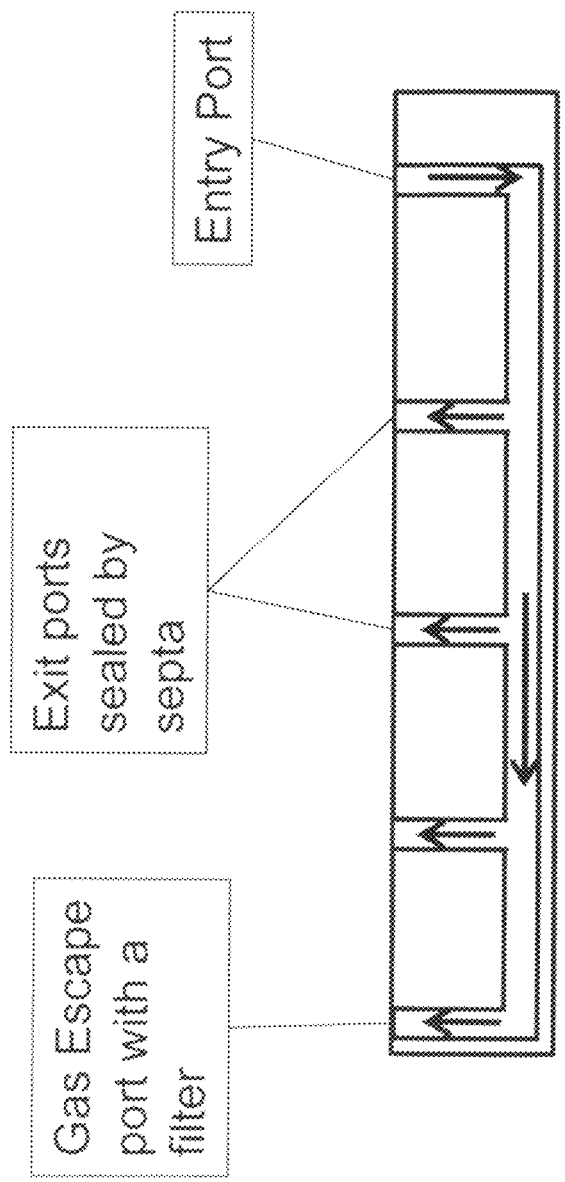
FIG. 15 illustrates an example system for parallel multiple dose dispensing according to one embodiment of the present invention.
Figure 16:
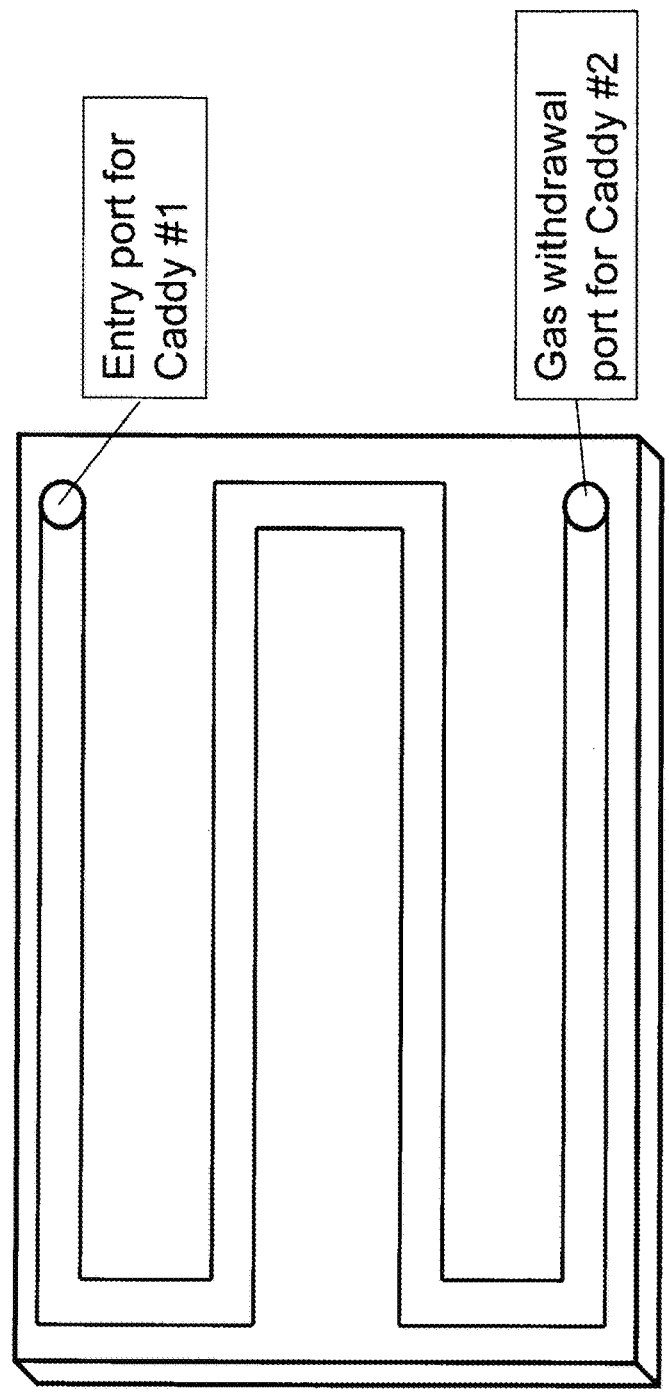
FIG. 16 illustrates an example system for parallel multiple dose dispensing according to another embodiment of the present invention.
Figure 17:
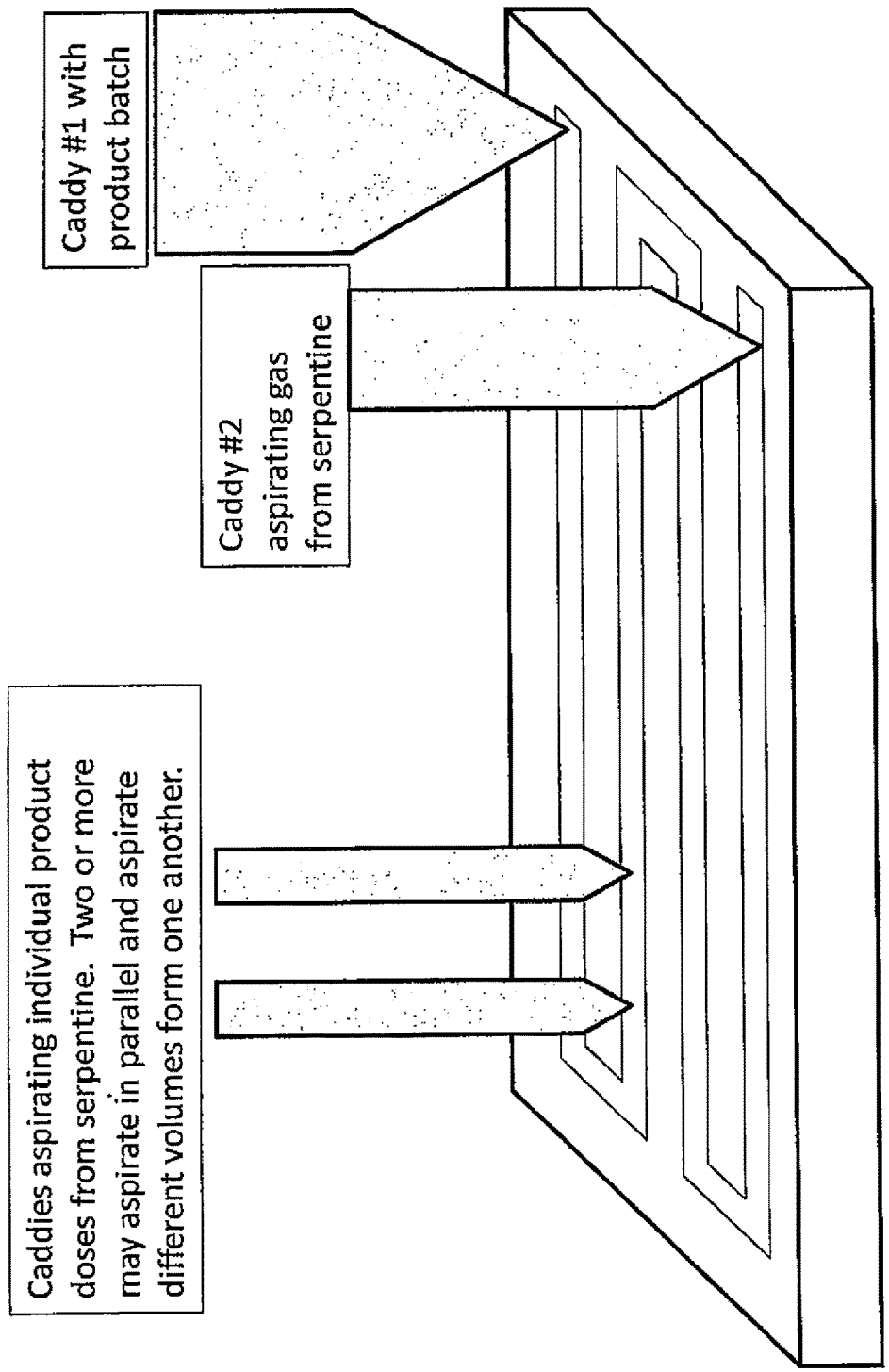
FIG. 17 illustrates an example system for parallel multiple dose dispensing according to one embodiment of the present invention.

FIG. 14 illustrates an example system for parallel multiple dose dispensing according to one embodiment of the present invention; FIG. 15 illustrates an example system for parallel multiple dose dispensing according to one embodiment of the present invention; FIG. 16 illustrates an example system for parallel multiple dose dispensing according to another embodiment of the present invention; and FIG. 17 illustrates an example system for parallel multiple dose dispensing according to one embodiment of the present invention.

According to one embodiment of the present invention, a liquid handler may include removable syringes used as caddies instead of pipette tips. Prior to dose dispensing, individual dose parameters are entered in a graphical user interface (GUI). Then that data is translated into the volume each syringe needs to draw. The syringes just need to access the source container all at the same time. The latter has not been possible so far in the existing systems because the source container is a vial accessible through a septum by one syringe at a time. Embodiments of the present invention allow filling a flat palette with the volume of product that may be accessible to multiple syringes at the same time through a sealed horizontal surface. In one embodiment, referring to FIG. 14, the palette contains a serpentine channel of small total volume that is filled with product pressurized from a larger container or one of the caddies (which may or may not be a syringe). The larger container or one of the caddies may transfer the entire volume of product including multiple patient doses of radiopharmaceutical product by piercing a septum at the entry port of the palette. All syringes pierce the serpentine at different locations at the same time. As they pull the liquid in, the serpentine is refilled by pressurized product from the larger container/caddy. This way the total volume of the product aspirated by all syringes is much larger than that of the serpentine. The serpentine may be fully enclosed within the palette with only specific locations accessible through pierce-able septa to aspirating caddies (exit ports) as shown in FIG. 15, or the serpentine may be formed without a ceiling within a palette (like a maze or labyrinth) and then sealed on the top at once with a flat sheet, as shown in FIG. 16. Here, the palette may include an entry port for a large container or caddy with the product, and a gas withdrawal port for another caddy to aspirate gas that is trapped in the serpentine, thereby filling the serpentine with products that flows unrestricted from the caddy at the entry port. For example, caddy #1 may dock at one location at the start of the serpentine and pierce the seal. Meanwhile caddy #2 may pierce the serpentine at its end and aspirate precisely the volume of gas that is trapped in the serpentine, therefore filling it with product that flows unrestricted from caddy #1. The aspirating caddies may pierce the top seal at other locations and draw doses. Two or more caddies may aspirate in parallel and aspirate different volumes from one another.

Alternatively, the final product container may be a pierceable bag. As multiple syringes pierce it concurrently or simultaneously at multiple locations and start aspirating liquid, the bag shrinks or flattens. The volumes drawn by each syringe may be determined on the go automatically after concentration data is available from QC. Two options exist for sample dilution if needed. Either the entire product batch is diluted and syringes draw from the diluted batch container; or the syringes draw concentrated product followed or preceded by aspiration of saline from a different source. In contrast, all prior art and conventional wisdom suggest sequential dose aspiration because everyone aspirates from vials with a septa. Also, dose dispensing refers to not only drawing patient doses into syringes, but also placing syringes into individual shielded containers (commonly known as "pigs" in the radiopharmaceutical industry). So overall the user just enters what doses they want to get out of the process in the graphical user interface and receives doses in syringes inside pigs ready for shipment. The system may also label both syringes and pigs with unique identifiers referring to specific patient doses. The label may include barcodes and RFID tags for sample tracking. Embodiments described above with regard to dose dispensing may be part of the system that combines synthesis, QC and dose dispensing together, or may be a system alone just for dose dispensing, or a system that combines dose dispensing with one of synthesis and QC.

In addition, the following embodiments are all included in the scope of the present invention.

All surfaces touched by a sample after its delivery form the target and until final dose package in a system are single-use and disposable. The sample does not touch any multi-used cleanable surfaces. One or more kits may be enabled by palettes and caddies.

One consumable contains components needed for synthesis, formulation, QC and dose dispensing. One or multiple consumables in combination cover all aspects of synthesis, formulation, QC and dose dispensing. System may include on-board air handling and/or on-board radiation shielding. The system allows assurance of sterility of the final dispensed product. The system may deliver sterile product starting with non-sterile isotope delivered from the accelerator target. The reagents are pre-packaged in a disposable kit. The analytical reference standards may be pre-packaged in a disposable kit. Both reagents and analytical standards may be pre-packaged in one disposable kit.

Disposable kits designed for one or more or any combination of: formulation, QC, dose dispensing, and synthesis have been described. The system may be mobile. System may produce a product and generates a batch record. The system may also include the accelerator and may start the process with non-radioactive substances leading to a radioactive product ready for patient administration.

A system may use target pressure to drive parts of the synthesis, formulation, QC, dose dispensing or the entire process. The sterile filter may be attached to the final dose container/integrated with it.

One kit, package, cartridge or palette including filter, final dose container and analytical functions has been described. The system may also carry reagents and/or standards. The system may or may not have on-board electronics.

Embodiments of this system include but are not limited to systems for the production or PET and SPECT tracers, method and system where the consumable (or choice of consumable kit) determines the process parameters.

The consumable is the carrier of part or all of information that determines the process to be executed (including accelerator, synthesis, formulation, QC and dispensing).

In the system according to embodiments of the present invention, all the user needs to do is turn it on and select a consumable kit to insert into the system and the rest is done automatically yielding an injectable product at a known time.

The consumable that has all components necessary for the generation of the product is also the carrier of the recipe or triggers a choice of recipe within the system that recognizes this consumable automatically.

Potentially a system may include a storage sub-system with multiple types of consumables on board. So the user only has to input what product needs to be delivered and when, and the system does the rest including starting the accelerator at the right time and choosing the right consumable to be used.

Consumables may be stored in a controlled (air and temperature) environment within the system.

The system may include input means, such as buttons, for selecting the tracers, such as [F-18]FDG, [F-18]FLT, [C-11] Choline, [N-13] ammonia, [F-18]NaF, [F-18]Florbetapir (Amyvid) etc., leaving the user just to input the time when the product is needed.

A system where sterility of the sample is assessed without direct contact between sample and the detector has been described.

A system according to the present embodiment may have a continuous fluid path between the sterile filter and final dose container. The dose dispensing palette has at least one quality control function/feature.

Separate Pharmacy from the Manufacturing Site of Radiopharmaceuticals

Traditionally, facilities that produce PET tracers also operate as pharmacies that fill the prescription for each patient. One of the main reasons for such an arrangement is that the quality assessment on the final product relies on physical inspection by the pharmacist, who cannot fill the prescription unless he/she personally verified the product as suitability for human use.

Automated instruments that can assess all parameters of quality of a radiopharmaceutical with quantitative measurements and without human input according embodiments of the present invention, offer a unique opportunity to separate the manufacturing of PET tracers from the pharmacy and allow various combinations and ratios between pharmacies and manufacturing sites.

In one embodiment, a PET tracer (or another radiopharmaceutical) is subjected to automated multi-parametric analysis. The results of such analysis are captured and stored electronically. These results may also be viewed remotely allowing a pharmacist to review the test results without being co-located with the sample of the product. The pharmacist who reviews product quality remotely may then also release it for patient delivery remotely using secure electronic signature. Once such an arrangement is enabled, one pharmacist may be able to support multiple production facilities.

In one embodiment, the workflow could proceed as following. PET tracer is produced at a manufacturing facility. A sample of the product is drawn by a technician at that facility and injected into an automated QC instrument (located on-site). Once the instrument processes the sample and yields the results on all QC parameters, a report is sent securely to the pharmacist at a remote location. The pharmacist reviews the report and if all results are acceptable, releases the product for patient use via secure electronic approval/signature. The Technician on-site may then package and ship product (PET Tracer) to the imaging center where it will be administered to a patient.

According to one embodiment of the present invention, a single pharmacy offers its services to multiple production facilities at different locations (using automated instruments). This pharmacy will employ one or more pharmacists and eliminate the need for having a licensed pharmacist physically present at each production facility.

There are arrangements where production and dose dispensing are separated. The remote pharmacist will get the report from the production facility and then send his/her approval to the dose dispensing facility. This way both of those types of facilities do not need to have a pharmacist on their staff.

Having thus described in detail various embodiments of the present invention, it is to be understood that the invention defined by the above paragraphs is not to be limited to particular details set forth in the above description as many apparent variations thereof are possible without departing from the spirit or scope of the present invention.

At least the following embodiments have been described. A palette system is configured to hold one or more vials. The palette may have permanent fixtures for holding liquids, solids or gases. The palette may have a plurality of wells and one of the wells does not have a floor and is effectively an unrestricted see-through opening.

A method includes insertion of a container (vial) into the palette or instrument and the insertion of a container (vial) into the palette or instrument triggers other events. The palette may be made of more than one kind of materials. The palette may have some (permanent or removable) liquid containers that are made of one material and others of another material. The palette may contain both organic and aqueous reagents. The palette may contain non-compatible reagents. The palette may be coated with a protective film (completely or partially). The palette may have different size containers placed in a regular arrangement or randomly. The palette may have containers of various shapes. The palette may be sealed by one type of seal in some locations and by a different type of seal (and/or some unsealed) in other locations. The container volume may be reduced via an insert. The palette may have inserts that hold fluid/solid/gas. The palette may have inserts that displace liquid/solid/gas. The palette may contain chromatographic components. The palette may include stationary phase. The palette may include mobile phase. The palette may include TLC components. The palette may allow motion of liquid. The palette may allow motion of mobile phase along solid phase; The palette may include valves. The palette may include channels. The palette may include an injection loop. The palette may include a septum. The palette may include a septum-piercing device. The palette may include one or more caddies in presence or in absence of other features. The palette may include containers with or without reagents and/or seals. The palette may include optical features. The palette may include features that modify light. The palette may include sources of light. The palette may be utilized with devices that detect and/or quantify light or other optical signals. The palette may include a built-in mixer that effectively mixes 2 liquids or a liquid and a solid. The mixer may or may not be activated by one or more caddies. The mixer may be activated pneumatically, optically, mechanically or electrically. The palette may include radiation shielding. The shielding may protect the user or protect one signal from another or signal from noise. The palette may include a removable or permanent shielding. The shielding may be within a caddy. The palette may have no port. The palette may be configured to receive a sample without a port. The palette may be configured in such a way that any container may receive the analyte or any container is accessible at all times. The palette may include no channels and or valves. The palette may have all containers isolated from one another. The palette may have no fluid path(s). The palette may have no optical cells. The palette may be packaged with a combination of 2 or more of liquids/solids/gases. Each container within a palette may be sealed individually with different seals broken at different times in the process. The seals may be broken in any order (not in a rigidly defined sequence). The containers within a palette may be accessed in any order (once or more than once). The palette may have no movable components.

The palette may include reference materials to which the analyte may be compared along one or more properties. The palette may include all materials necessary for performing daily system suitability tests of an instrument (automatically). There may be a recognition system between the instrument and palettes (and/or caddies). The palette may include reagents and/or information (about reagents, methods, analytes or other aspects). The palette where the pattern of filled and empty (or variably filled) containers may be used to convey information. The palette may be made of two components that are filled/sealed individually.

A method where analyte is delivered to a palette in a syringe has been described. A palette and/or caddy system configured to draw/package doses for individual patients has been described. Some tests may be performed within a palette immediately after receipt of analyte while other tests may be delayed. Methods may require incubation of the palette prior to reading optical signals from it. The palette may be configured for performance of one or more tests in one instrument and another set of one or more tests in another instrument (or another facility). The results from one palette tested in different instruments may be combined into one report for the same analyte.

The palette may have gas flow enabled through it. The palette may have laminar gas flow through it. The palette may have a bio safety environment around it. The palette may have such environment only around the palette but not within the rest of the instrument. The palette may have part of it under the laminar flow or bio-safety system. The palette may have no walls. Fluids/solids/gases may be confined by methods other than physical barriers. Palettes may have designs represented in the figures and methods of using them. The palette may have inert or sterile atmosphere created just above the palette and protecting only its contents. The palette may have permanent fixture under the palette that assures inert environment above or around the palette. The fixture above may or may not penetrate the palette. Air routed to palette may pass through a HEPA filter. The HEPA filter may be built into the palette. Caddies may create an inert/sterile environment around and within the palette.

A device may be capable of assessing two or more quality control parameters from a single injection of sample into a palette. A palette may have reagents for one or more tests required for quality control. The quality control may be performed for a radiopharmaceutical. The device may include a liquid handler. The device may include a spectrophotometer. The device may include a plate reader. The device may include an HPLC. The device may include a spectrophotometer and an HPLC. The device may be capable of accepting a palette with reagents and a single well with analyte and distributing analyte between test locations within palette. The device may be capable of assessing optical signals corresponding to chemical properties resulting from reactions within a palette. The device may be capable of routing a fraction of analyte to HPLC. The routing may be performed via a caddy.

A method of assessing quality control parameters of analyte may be by reacting the analyte with various reagents and the reactions producing an optically detectable signal. The signal may be correlated with a specific measurement of a chemical, physical or nuclear property. A method of determining whether the sample is colored or colorless may utilize continuous spectrum absorption measurement and a threshold that is preset for a specific range of wavelengths. The wavelengths are in the visible range of the spectrum (360-700 nm.)

A method of measuring exact K222 concentration in a sample may be via an absorption measurement at one or more wavelengths of light being passed through the mixture of sample and indicator in a palette. The indicator may include a transition metal salt and a colorimetric indicator for measuring of this metal. Whether the sample is of acceptable quality may be determined by comparing the measurement against a preset value or range of values.

A method of measuring exact pH of a sample may be via absorption measurement at one or more wavelengths of light being passed through the mixture of sample and indicator in a palette. Whether the sample is of acceptable pH may be determined by comparing the measurement against a preset range of values.

A device and a method for Pyrogen testing without the requirement of liquid flowing through a channel have been described. The device for Pyrogen testing may be in combination with other tests. The device may be a palette. The Pyrogen testing may be conducted in a device combined with other tests. The Pyrogen testing may be conducted in parallel with other assessments.

A method of assessment of radioactive sample half-life and radionuclidic purity without a dose calibrator has been described. A method of continuous measurement of radioactive decay for determination of half-life and radionuclidic purity has been described. A method of determination of half-life and radionuclidic purity without shielding the sample from other sources of radiation or other samples has been described. A method of assessment of radioactivity concentration may be conducted without a dose calibrator. A method for determination of the radioactivity concentration may be conducted without shielding the sample from other sources of radiation or other samples.

A method of measuring exact solvent concentration in a sample may be via an absorption measurement at one or more wavelengths of light being passed through the mixture of sample and indicator in a palette. A method of determining whether the sample has acceptable solvent concentration may be conducted by comparing the measurement against a preset value or range of values.

A method of performing chromatography within a palette has been described. A device capable of performing chromatography within a palette has been described. A device for Radio-TLC or radio HPLC within a palette has been described. A method for Radio-TLC or radio HPLC within a palette has been described. A device for TLC assessment in combination with scintillating liquid has been described.

A method for TLC assessment may be in combination with scintillating liquid. A method using scintillating liquid for chromatography has been described.

A device and method for delivery of sample to analytical HPLC via a palette/caddy system have been described. A device/method where an HPLC sample is yielded by a caddy on a palette have been described. A method for HPLC injection and results integrated with sampling and reporting for other QC tests has been described.

A device may have all calibration samples required to be processed prior to analyte pre-packaged on a palette. A device and a system that perform system suitability testing and sample analysis in one process and using the same package. The package is a pre-loaded palette. A method where a single injection into HPLC allows analysis of chemical and radiochemical purity as well as organic solvent concentration or any other combination of these tests has been described. The palette may contain chromatographic media. The media may be a TLC plate. The media may be a packed column. The device may be utilized for separating chemical mixtures. The components of a separated mixture may be detected. The components may be identified. The amounts of components may be quantified. The radioactive components may be detected by their radioactive signal. A method may utilize a scintillating liquid. The scintillating liquid may be in very close proximity to the stationary phase but not touching it. The scintillating liquid may be a component of the mobile phase.

A device and a method for performing chromatography using a stationary phase and mobile phase where mobile phase contains scintillating material have been described. A device for performing chromatography using a stationary phase and mobile phase where stationary phase contains scintillating material has been described. A device for Sterility assessment with a spectrophotometer has been described. A method for Sterility assessment may include a spectrophotometer. A method of Sterility assessment may be conducted in a palette (with all options for it). A quantitative sterility assessment may be conducted according to the rate of colony growth. A method of filter test with data/results feeding directly into an overall QC report automatically, and leaves no room for human judgment.

At least the following embodiments of a method have been described:

A method of sterility testing based on labeling live cells with reagents that allow quantification of the number of cells by optical detection in a palette; a device where optical signal from labeled live cells can be detected and translated into the number of live cells in the sample; a device for sterility assessment comprising a channel; the channel has one or more electrodes; the channel is connected to a reservoir; the channel is connected to two or more reservoirs; the cross-section of the channel is comparable to the size of a living cell; the electrodes perform a measurement; the signal is different in presence and in absence of live cells in proximity to electrode(s); the signal may be used to count live cells; more than one channel may be included; all channels run in parallel; all channels have the same originating container; all channels have the same final container; a palette containing any combination of the following reagents: pH indicator, K222 indicator, scintillating liquid, and LAL reagents; a palette containing both solids and liquids; a palette containing solids in the 0.1 mg range; a plate containing solids and solvents that from mixtures that are unstable for prolonged periods of time (such as LAL reagents); a method of using a palette for the assessment of a gamma spectrum (MCA); a method of using palettes for QC or radiopharmaceuticals; the palette is a standard microtiter plate; the palette sealed with reagents; the palette may contain HPLC references and standards either in solid or liquid form; a method of performing self-calibration of HPLC using only the contents of one palette; a method for radiation detection using a spectrophotometer; a method for radiation detection using a plate reader; a device for radiation detection comprising a palette and a plate reader; the device including a sub-system capable of chemical synthesis; the device enabling radiosynthesis or a radiopharmaceutical; the device including a sub-system capable of dispensing product; the product may be dispensed as single patient doses; a device and method for optical detection of any of the following or any combination thereof: color, clarity, pH, K222 concentration, endotoxin concentration, radioactivity concentration, radionuclidic identity, radiochemical identity, radiochemical purity, concentrations of organic solvents, sterility.

A method of using palettes where solute includes a radionuclide; a device and method for Optical detection using a palette; a device and method where LC injection is performed form a palette; the palette may be placed in an optical path between the source of an optical signal and detector; the device and method may include and utilizing a plate reader; a method of assessing all QC parameters of a radiopharmaceutical using a palette but without flowing any liquids from one location on the palette to another at any time; a method of assessing all QC parameters of a radiopharmaceutical using a palette allowing flow of liquids from one location on the palette to another; a method of QC assessment relying on measurement of an optical property; a method of QC assessment relying on measurement of a change in optical property; a method of QC assessment relying on measurement of a rate of change in optical property; a method and device for full assessment of QC or radiopharmaceuticals without running any liquids through any channels; a method and device for full assessment of QC or radiopharmaceuticals without running any liquids through any valves; a method and device for full assessment of QC or radiopharmaceuticals required for administering product to a human patient; a method and device for partial assessment of QC or radiopharmaceuticals without running any liquids through any channels; a method and device for partial assessment of QC or radiopharmaceuticals without running any liquids through any valves; a device and method for QC assessment of radiopharmaceutical having no injection port; a device and method for QC assessment of radiopharmaceutical having no network of channels and/or valves; a device and method for QC assessment of radiopharmaceutical having internal or external radiation shielding; a device and method for QC assessment of radiopharmaceutical where all results are quantitative; a device and method for QC assessment of radiopharmaceutical where all results are quantitative and compiled in a single report produced automatically; a method of measuring exact turbidity of a sample using continuous spectrum absorption measurement; a method for determining whether the sample is of acceptable turbidity by comparing the measurement against a preset threshold; a device and method where all materials necessary for full QC assessment are packaged on a palette; the device and method may include HPLC solvents; a device/method with a combination of transition metal and transition metal-sensitive indicator for detection/quantification of K222 in a sample; the device may have two or more reagents mixed with each other (pre-packaged palette contains these reagents as a mixture prior to use.); a palette containing only solids (solvents may be stored as stock within the instrument or come separately); a method relying on two palettes where one has all the reagents and the other is used for detection; a method where the reagents are pre-packaged on a palette in excess, but are metered by the caddy in specific amounts for use in the tests; a method of performing QC of a radiopharmaceutical having a "cold phase" (prior to injection of radioactive analyte) and a "hot phase" after the injection of the latter (with optimization concentrating on minimizing the latter phase and moving as many manipulations as possible from hot phase to cold); a method and device for Assessment of radioactive signals arising from different wells within a palette without shielding those wells from one another; a method where the distinction between colored sample and a turbid sample is made based on the fitting of the absorption spectrum with a mathematical equation; such equation may be an exponential function; the fitting with chi2 above certain threshold deemed a signal for the sample being colorless; a device for organic solvent concentration assessment with HPLC; HPLC injection driven by a system of caddies and palettes without human interference; full report on all QC parameters generated automatically from 1 injection of analyte without user interaction with the instrument; chemical purity assessment without chromatography; chemical purity assessment by comparing an absorption spectrum to a reference absorption spectrum at multiple wavelengths; specific activity assessment without chromatography; sterility assessment by counting cells in a channel between two electrodes; sterility assessment device having two wells connected by multiple channels and electrodes measuring an electrical signal across each channel; a method of using the devise described above to assess sterility or presence of live cells; devices for electrode or absorption-based sterility measurements that are either completely based on palettes and caddies or do not involve them at all.

The following are additional embodiments of the invention:

A system for performing manipulations with radioactive materials, relying for the transfer of materials on the palettes and caddies; An integrated system that includes a part that relies on palettes and caddies and another part that utilizes other means for the material transfer; A system where the manipulations are used to assess quality control parameters of a radiopharmaceutical sample; A system where the chemical manipulations are used in the synthesis of radiolabeled molecules; A system where the transfer of materials is performed as a part of dispensing, that is preparation of existing material for shipping and use by an end-user; A system where the aforementioned chemical manipulations are used in any combination of synthesis, analysis and/or dispensing of radioactive materials; An aforementioned system designed to manipulate the amount of radioactive material not requiring special radiation shielding; An aforementioned designed to manipulate radioactivity in such a manner that 2 inch lead shielding or its equivalent is sufficient for safe operations; An aforementioned system that collects all liquid waste material within palettes and caddies; A system for manipulation of radioactive material where the material only comes in contact with the disposable surfaces, that is surfaces only used for one operation (with examples including but not limited to synthesis/analysis/transfer/mixing/extraction); A system where the same palette is shared between the processes performed in the system: synthesis, analysis, dispensing or any combination of thereof; A system where each process uses a designated palette; A system that may be portable, that is sufficiently small to be moved from one location to another and only rely on external power supply for its operation; A system which provides for temperature control for the entire palette of a portion thereof; An aforementioned integrated system that uses caddies to transfer material form the palette-caddy part of the system to the parts of the system operating based on different principles, such as chromatographic equipment;

Palette, that is disposable components used in the radiochemical synthesis, analysis or dispensing, includes plurality of containers not interconnected with each other used in synthesis, analysis or dispensing of radioactive materials; Palettes made out of single piece of homogeneous material; Palettes made out of multiple pieces of material and linked to each other, inserted in each other or otherwise mechanically connected; Such combinations may include combinations of disposable and re-usable components; Palettes where containers may be moved within a palette; A palette that incorporates radiation shielding;

Caddy, that is a disposable component used as a temporary container to transfer material between containers of a palette or from a palette outside of the system; Caddies designed to deliver material (final product, analyte sample or other) to the end user and used directly, without further transfer of material enclosed; Caddies designed to be docked to hardware other than the palette; A caddy that incorporates radioactive shielding; Palettes and caddies that contains silica, modified silica, ion exchange resin or any other sorbent in one or more containers;

A radiochemistry system designed to perform periodic sampling of the reaction mixture and analysis of the samples (obtained at different time-points throughout the synthesis process and not limited to sampling the end-product) within the same system;

A system of that is designed to automatically receive the palettes from a storage location and automatically eject used palettes and caddies into a receptacle (potentially a shielded one in some embodiments), thus permitting continuous operation with no human interference;

A system that performs quality control of a radiopharmaceutical along a plurality of parameters, including, but not limited to clarity, pH, a phase transfer reagent concentration, pyrogenicity, radio-isotope half-life and radioactivity concentration;

The aforementioned system that measures several parameters in one test and reports several parameters to meet specifications if the test results are satisfactory;

The methods relying on the aforementioned systems and components are also embodiments of the invention; Such as An automated method for separation and/or purification of radiopharmaceuticals relying on liquid-liquid extraction performed by means of palettes and caddies;

A method for performing quality control of radiopharmaceuticals that relies on use of palettes and caddies;

In one embodiment, the system is configured to synthesize, analyze or dispense chemicals used in diagnostic imaging, such as PET; These chemicals comprise at least one radionuclide, which may be selected from the group consisting of 11C, 13N, 15O, 18F, 61Cu, 62Cu, 64Cu, 67Cu, 68Ga, 124I, 125I, 131I, 99Tc, 75Br, 153Gd and 32P;

A system for performing manipulations with radioactive materials, relying for the transfer of materials on the palettes and caddies;

An integrated system that consists of a part that relies on palettes and caddies and another part that utilizes other means for the material transfer;

Systems where the transformations are used to assess quality control parameters

Systems where the chemical transformations are used in the synthesis of radiolabeled molecules;

Systems where the transfer of materials is performed in order to prepare an existing material for shipping and use by an end-user;

A system including a combination of the afore mentioned systems or a subset of thereof;

A system for performing of manipulation of radioactive material where the material only comes in contact with the disposable surfaces, that is surfaces only used for one operation, including but not limited to synthesis/analysis/transfer;

A system where the manipulations are directed toward synthesis, analysis, dispensing of radiopharmaceuticals or combination of these processes or subset of these processes;

A system where the same palette is shared between the processes performed in the system: synthesis, analysis, dispensing or any combination of thereof;

A system where each process uses a designated palette;

Disposable components comprised of plurality of containers with not interconnected with each other (palettes) used in synthesis, analysis or dispensing of radioactive materials;

Palettes made out of single piece of homogeneous material;

Palettes made out of multiple pieces of material and linked to each other, inserted in each other or otherwise mechanically connected;

Palettes where containers may be moved within a palette

Disposable component used as a temporary container to transfer material between containers of the palette;

Disposable component used as a temporary container to transfer material outside of the system;

Disposable component designed to be used by the end user;

Disposable component where the content of the caddy is a radiopharmaceutical ready for injection;

Disposable component designed to be docked to hardware other than the palette;

A system designed to manipulate the amount of radioactive material not requiring special radiation shielding;

A system designed to manipulate radioactivity in such a manner that 2 inch lead shielding or its equivalent is sufficient for safe operations;

A palette that incorporates radiation shielding;

A caddy that incorporates radioactive shielding;

A system that collects all liquid waste material within pallets and caddies;

A system that may be portable, that is sufficiently small to be moved from one location to another and only rely on external power supply for its operation A system which provides for temperature control for the entire palette of a portion of thereof;

A system that uses caddies to transfer material form the palette-caddy part of the system to the parts of the system operating based on different principles, such as chromatographic equipment;

Disposable component that contains silica, modified silica, ion exchange resin or any other sorbent in on or more containers;

Disposable components that contain silica, modified silica, ion exchange resin or any other sorbent;

An automated method for separation and/or purification of radiopharmaceuticals relying on liquid-liquid extraction performed by means of palettes and caddies;

A radiochemistry system designed to perform periodic sampling of the reaction mixture and analysis of the samples within the same system;

A system that is designed to automatically receive the palettes from a storage location (inside or outside the system) and automatically eject used palettes an caddies into a receptacle, thus permitting continuous operation with no human interference;

A system that performs quality control of a radiopharmaceutical along a plurality of parameters, including, but not limited to clarity, pH, a phase transfer reagent concentration, pyrogenicity, radio-isotope half-life and radioactivity concentration;

A system that measures several parameters in one test;

A system that reports several parameters to meet the specifications if the result of this one test is acceptable;

A system that relies on a palette with solid support or absorbent embedded in one or more containers of a caddy;

A machine that allows complete assessment of the quality of a radiopharmaceutical without any part of the analysis relying on human senses;

An device that generates a report that can be reviewed remotely

An device that allows quality assessment of a sample without the reviewer of results being co-located with the sample;

A system where the reviewer of the report can review such reports from multiple production facilities and release products at multiple locations for human administration;

Business model where a pharmacy offers its services to multiple radiopharmaceutical production facilities Such pharmacy may or may not be affiliated with an individual production site;

Whereas particular embodiments of the present disclosure have been described above for purposes of illustration, it will be understood by those skilled in the art that numerous variations of the details of the present disclosure may be made without departing from the invention as defined in the appended claims, and equivalents thereof.

Although various embodiments of the present disclosure have been described in terms of "comprising" or "including," embodiments "consisting essentially of" or "consisting of" are also within the scope of the present disclosure.

As used herein, unless otherwise expressly specified, all numbers such as those expressing values, ranges, amounts or percentages may be read as if prefaced by the word "about," even if the term does not expressly appear. Further, use of the word "about" reflects the penumbra of variation associated with measurement, significant figures, and interchangeability, all as understood by a person having ordinary skill in the art to which this disclosure pertains. Any numerical range recited herein is intended to include all sub-ranges subsumed therein. Plural encompasses singular and vice versa. When ranges are given, any endpoints of those ranges and/or numbers within those ranges can be combined within the scope of the present disclosure. Notwithstanding that the numerical ranges and parameters set forth herein may be approximations, numerical values set forth in the specific examples are reported as precisely as is practical. Any numerical value, however, inherently contains certain errors necessarily resulting from the standard variation found in their respective testing measurements.

The term "comprising" and variations thereof as used in this description and in the claims do not limit the disclosure to exclude any variants or additions. The terms "including" and like terms mean "including but not limited to."

The present invention has been described with reference to example embodiments and aspects, but is not limited thereto. Persons of ordinary skill in the art will appreciate that other modifications and applications can be made without meaningfully departing from the invention. Accordingly, the foregoing description should not be read as limited to the precise embodiments and aspects described, but should be read consistent with and as support for the following claims, which are to have their fullest and fairest scope.

What is claimed is:

1. A system for evaluating a quality of a radiopharmaceutical product, comprising:
a first container and a second container in fluidic isolation from one another, the first container including a first quality control reagent and the second container including a second quality control reagent other than the first quality control reagent;
a palette including a third container and a fourth container;
a liquid handler adapted to withdraw the first quality control reagent from the first container and deliver the first quality control reagent to the third container, the liquid handler adapted to withdraw the second quality control reagent from the second container and deliver the second quality control reagent to the fourth container;
a palette moving mechanism adapted to move the palette between a first position and a second position; and
a plate reader disposed at the second position and including a light detector, wherein at least one of the first quality control reagent and the second quality control reagent produces an optically detectable signal when contacted with the radiopharmaceutical product, wherein the light detector is operable to output a signal indicative of the quality of the radiopharmaceutical product based on the optically detectable signal, the third container and the fourth container being positioned proximate the light detector when the palette is disposed at the second position.

2. The system of claim 1, wherein the first quality control reagent comprises a scintillating material, the scintillating material positioned in proximity with the radiopharmaceutical product to convert positrons emitted from the decaying radiopharmaceutical product into light detectable by the plate reader.

3. The system of claim 1, wherein the other of the at least one first quality control reagent and the second quality control reagent reacts with the radiopharmaceutical product to generate an optically detectable signal that is correlated with a quality control parameter.

4. The system of claim 1, wherein the palette includes a chromatographic component on which the radiopharmaceutical product components may be separated.

5. The system of claim 4, wherein the chromatographic component is an ion exchange column.

6. The system of claim 4, wherein the chromatographic component is a thin layer chromatography (TLC) plate.

7. The system of claim 1, wherein the first quality control reagent comprises a colorimetric reagent responsive to a phase transfer reagent, wherein the phase transfer reagent is Kryptofix, and the colorimetric reagent comprises a metal compound.

8. The system of claim 1, wherein the palette includes one or more containers configured to carry a chemical in solid form that is unstable in solution form; and
one or more containers configured to carry a solvent, wherein the chemical in solid form and the solvent are selected to solvate the chemical in solid form to generate a solution form of the chemical.

9. A system for evaluating a quality of a radiopharmaceutical product, comprising:
a first palette including a first container and a second container in fluidic isolation from one another, the first container including a first quality control reagent and the second container including a second quality control reagent other than the first quality control reagent;
a second palette including a third container and a fourth container in fluid isolation from one another;
a liquid handler adapted to transfer the first quality control reagent from the first container to the third container, the liquid handler adapted to transfer the second quality control reagent from the second container to the fourth container, the liquid handler adapted to transfer the radiopharmaceutical product to the third container and the fourth container;
a palette moving mechanism adapted to move the palette between a first position and a second position; and
a plate reader including a light detector, the third and fourth containers being positioned proximate the light detector when the palette is at the second position, wherein at least one of the first quality control reagent and the second quality control reagent produces an optically detectable signal when contacted with the radiopharmaceutical product, wherein the light detector is operable to output a signal indicative of the quality of the radiopharmaceutical product based on the optically detectable signal.

10. The system of claim 9, wherein the first quality control reagent comprises a scintillating material, the scintillating material positioned in proximity with the radiopharmaceutical product to convert positrons emitted from the decaying radiopharmaceutical product into light detectable by the plate reader.

11. The system of claim 9, wherein the other of the at least one first quality control reagent and the second quality control reagent reacts with the radiopharmaceutical product to generate an optically detectable signal that is correlated with a quality control parameter.

12. The system of claim 9, wherein the palette includes a chromatographic component on which the radiopharmaceutical product components may be separated.

13. The system of claim 12, wherein the chromatographic component is an ion exchange column.

14. The system of claim 12, wherein the chromatographic component is a thin layer chromatography (TLC) plate.

15. The system of claim 9, wherein the first quality control reagent comprises a colorimetric reagent responsive to a phase transfer reagent, wherein the phase transfer reagent is Kryptofix, and the colorimetric reagent comprises a metal compound.

16. The system of claim 9, wherein the palette includes one or more containers configured to carry a chemical in solid form that is unstable in solution form; and
one or more containers configured to carry a solvent, wherein the chemical in solid form and the solvent are selected to solvate the chemical in solid form to generate a solution form of the chemical.

* * * * *

UNITED STATES PATENT AND TRADEMARK OFFICE
CERTIFICATE OF CORRECTION

PATENT NO.        : 10,309,947 B2
APPLICATION NO.   : 14/191293
DATED             : June 4, 2019
INVENTOR(S)       : Arkadij Elizarov et al.

Page 1 of 1

It is certified that error appears in the above-identified patent and that said Letters Patent is hereby corrected as shown below:

On the Title Page

Item (60) Related U.S. Application Data and in the Specification Column 1, Line 9:
Delete: "Provisional application No. 61/888,477, filed on Oct. 8, 2013, provisional application No. 61/886,607, filed on Oct. 3, 2013, provisional application No. 61/769,750, filed on Feb. 27, 2013, provisional application No. 61/834,354, filed on Jun. 12, 2013."
Insert: --Provisional application No. 61/888,477, filed on Oct. 8, 2013, provisional application No. 61/886,607, filed on Oct. 3, 2013.--

Signed and Sealed this
Twenty-fourth Day of September, 2019

Andrei Iancu
*Director of the United States Patent and Trademark Office*